US012201361B2

(12) United States Patent
Samadani et al.

(10) Patent No.: US 12,201,361 B2
(45) Date of Patent: Jan. 21, 2025

(54) METHODS AND KITS FOR ASSESSING CENTRAL NERVOUS SYSTEM INTEGRITY

(71) Applicants: NEW YORK UNIVERSITY, New York, NY (US); THE UNITED STATES GOVERNMENT AS REPRESENTED BY THE DEPARTMENT OF VETERAN AFFAIRS, Washington, DC (US)

(72) Inventors: Uzma Samadani, New York, NY (US); Shani Offen, New York, NY (US); Marisa Carrasco-Queijeiro, New York, NY (US); David Heeger, New York, NY (US)

(73) Assignees: NEW YORK UNIVERSITY, New York, NY (US); THE UNITED STATES GOVERNMENT AS REPRESENTED BY THE DEPARTMENT OF VETERAN AFFAIRS, Washington, DC (US)

( * ) Notice: Subject to any disclaimer, the term of this patent is extended or adjusted under 35 U.S.C. 154(b) by 182 days.

(21) Appl. No.: 17/697,860

(22) Filed: Mar. 17, 2022

(65) Prior Publication Data

US 2022/0202289 A1 Jun. 30, 2022

Related U.S. Application Data

(60) Division of application No. 16/260,379, filed on Jan. 29, 2019, now Pat. No. 11,304,601, which is a continuation of application No. 15/429,413, filed on Feb. 10, 2017, now Pat. No. 10,219,694, and a continuation of application No. 14/387,892, filed as
(Continued)

(51) Int. Cl.
| | | |
|---|---|---|
| A61B 3/113 | (2006.01) | |
| A61B 3/00 | (2006.01) | |
| A61B 5/00 | (2006.01) | |
| A61B 5/03 | (2006.01) | |
| A61B 3/024 | (2006.01) | |

(52) U.S. Cl.
CPC ............ *A61B 3/113* (2013.01); *A61B 3/0025* (2013.01); *A61B 5/031* (2013.01); *A61B 5/4064* (2013.01); *A61B 5/4076* (2013.01); *A61B 5/7246* (2013.01); *A61B 5/7264* (2013.01); *A61B 3/024* (2013.01); *A61B 5/7275* (2013.01)

(58) Field of Classification Search
CPC ..... A61B 3/113; A61B 3/0025; A61B 5/4064; A61B 5/4076
See application file for complete search history.

(56) References Cited

U.S. PATENT DOCUMENTS

| | | | |
|---|---|---|---|
| 2002/0169364 A1* | 11/2002 | Baumzweiger | A61B 5/00 600/300 |
| 2010/0100001 A1* | 4/2010 | Aguilar | A61B 5/378 600/595 |
| 2010/0238405 A1* | 9/2010 | Newman | A61B 5/0066 351/200 |

\* cited by examiner

*Primary Examiner* — Daniel L Cerioni
(74) *Attorney, Agent, or Firm* — SLEMAN & LUND LLP

(57) ABSTRACT

A system includes an eye tracker having a camera, the eye tracker being configured and arranged to track an eye movement of a subject, and a processor in communication with the eye tracker, the processor being configured and arranged to create a dataset of the eye movement, generate a plot of the dataset, the plot reflecting a timecourse of eye position versus time, and identify one or more streaking vertical lines in the plot to indicate a deficit in cranial nerve II function.

4 Claims, 52 Drawing Sheets

80 year old male with a history of ocular histoplasmosis

Left Eye Counts fingers

Right Eye 20/200

Central optic nerve atrophy = streaking vertical lines

Related U.S. Application Data application No. PCT/US2013/033672 on Mar. 25, 2013, now Pat. No. 9,642,522.

(60) Provisional application No. 61/710,213, filed on Oct. 5, 2012, provisional application No. 61/615,463, filed on Mar. 26, 2012.

February 15, 2012

February 23, 2012

March 05, 2012

Cranial nerves III, IV and VI move the eyes in a square

Eye movement tracking of the left eye in a patient with a VIth with nerve palsy from remote trauma, no elevated intracranial pressure Comparison of fluctuation and sustained neural pressure perturbations on axonal transport processes in the optic merve Length of exposure to subarachnoid space:
IV – 33 mm
III – 26 mm
II – 5 to 16 mm
VI – 11 mm FIG. 7
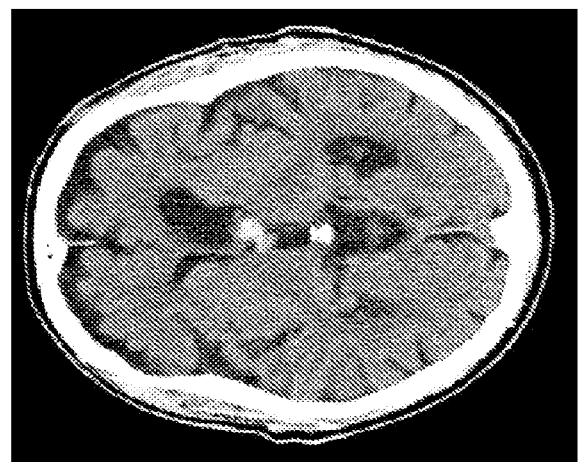
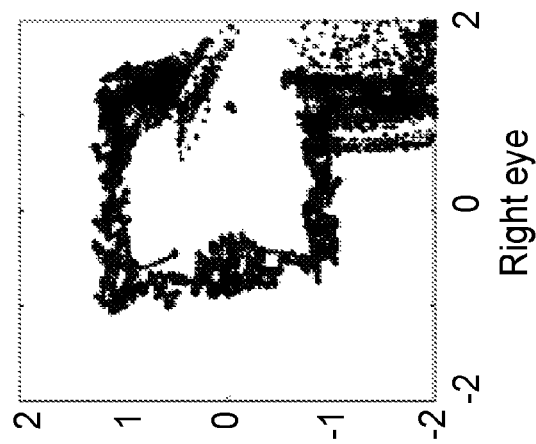
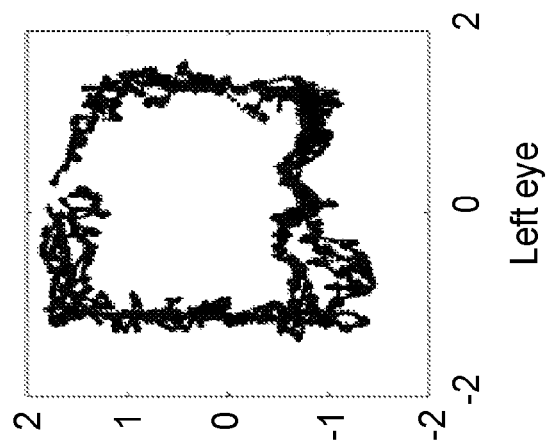

FIG. 8
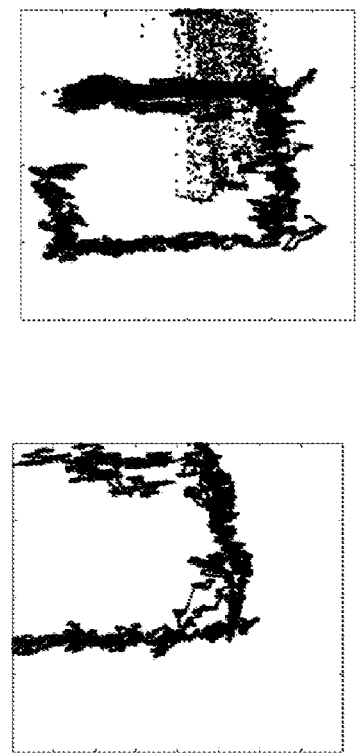
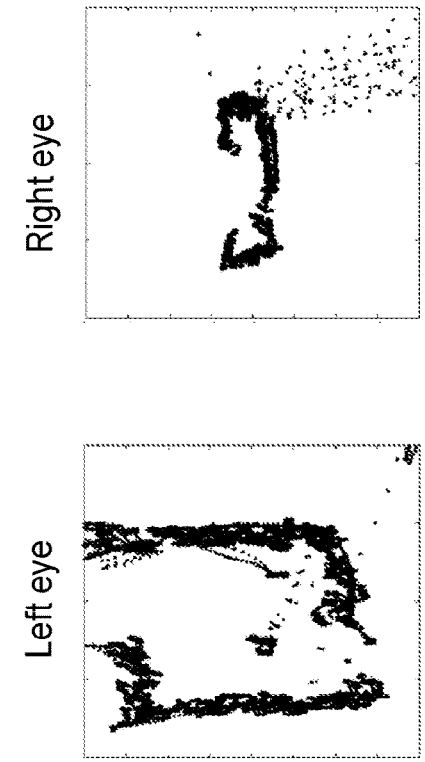
86 year old male presented 6 wks after a fall with headache
L III, IV from high ICP
Right eye
Left eye
L III>> R IV
8 days later, still neurologically intact on exam
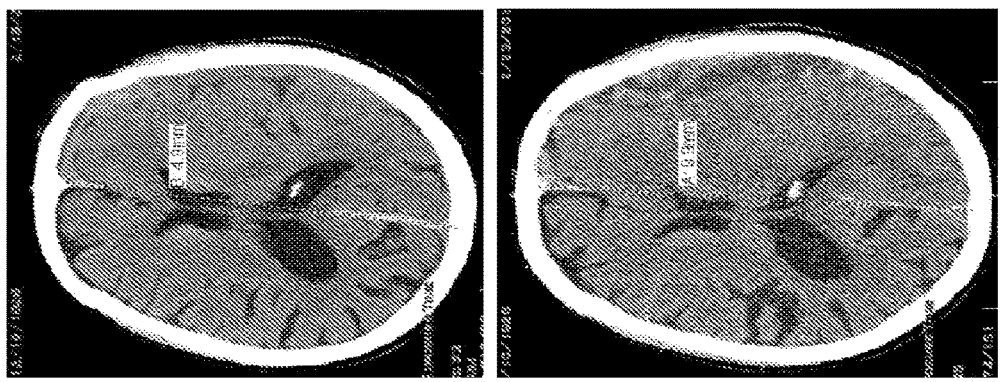

FIG. 9
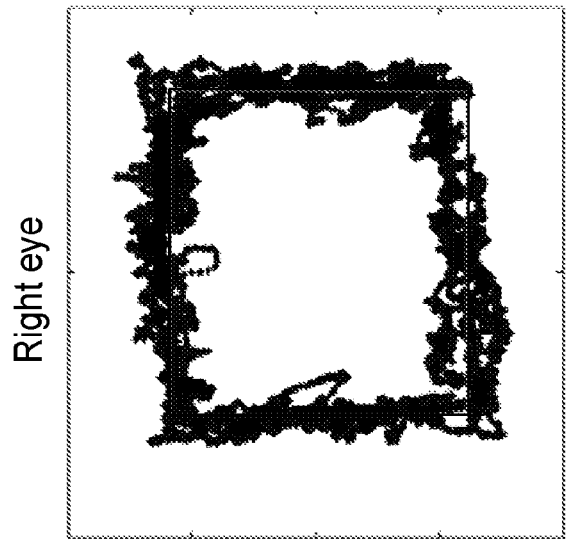
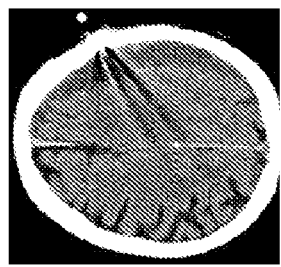
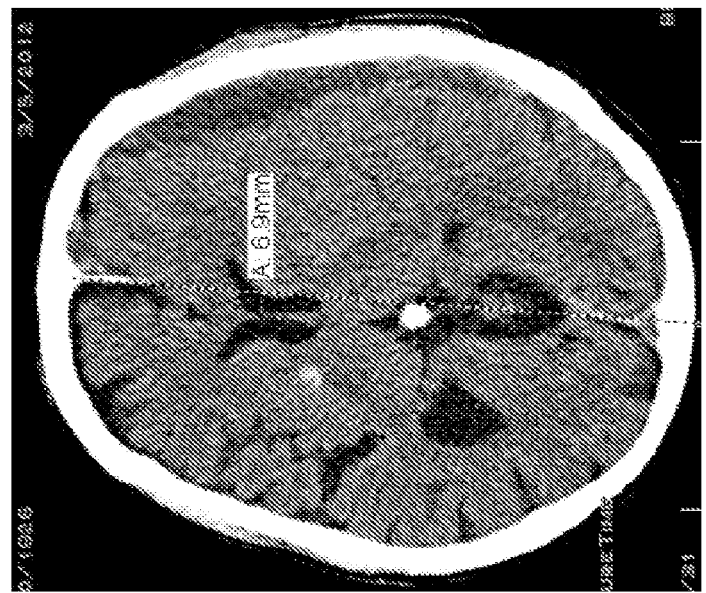

FIG. 10
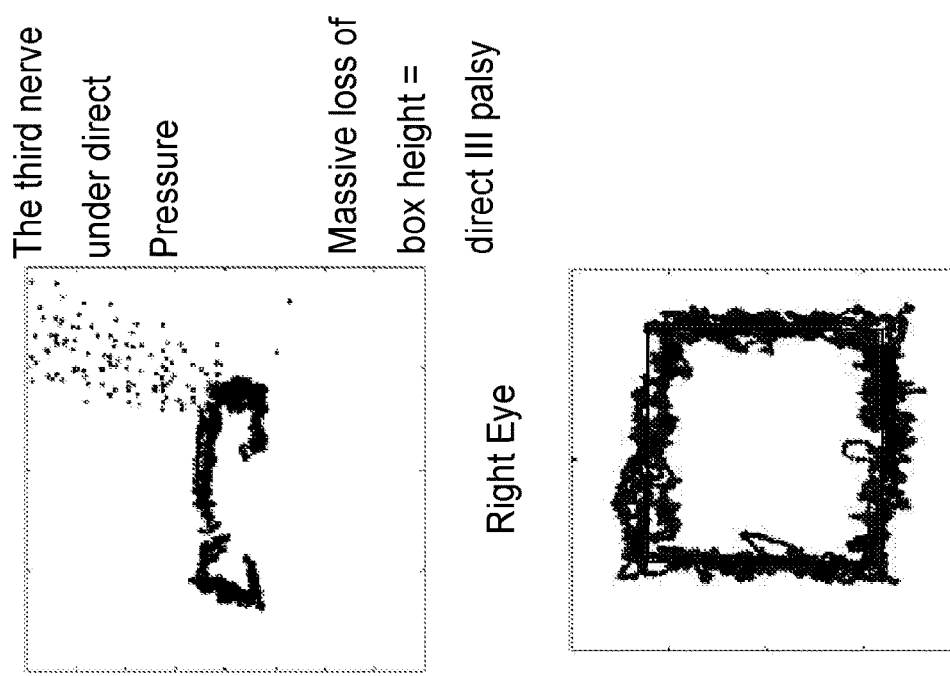
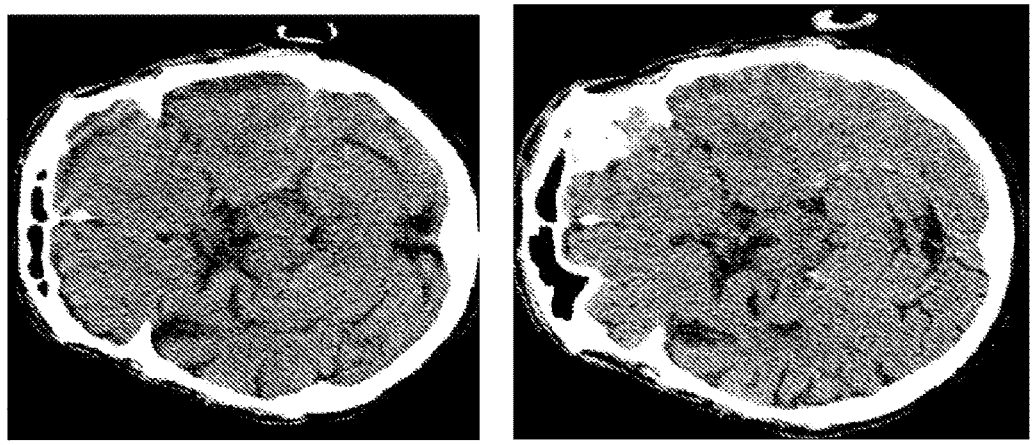

Hydrocephalic Patient: 62 yo male s/p resection, chemo and XRT of a thoracic ependymoma in 2002 at an OSH; resultant paraplegia. Came to our clinic with recurrence in 2010; declined surgical intervention until developing worsening UE function and decreased spontaneous speech in December 2011:

Head CT Dec 2011;

Head CT May 2010; after a fall

Underwent re-resection of ependymoma, and placement of ventriculostomy. Mental status returned to baseline; ventriculostomy was weaned. Re-presented with paucity of spontaneous speech; hydrocephalus necessitating a shunt. (Complicated by ARDS/pneumonia/ESRD/sepsis)

Eye movement tracking in an aphasic patient

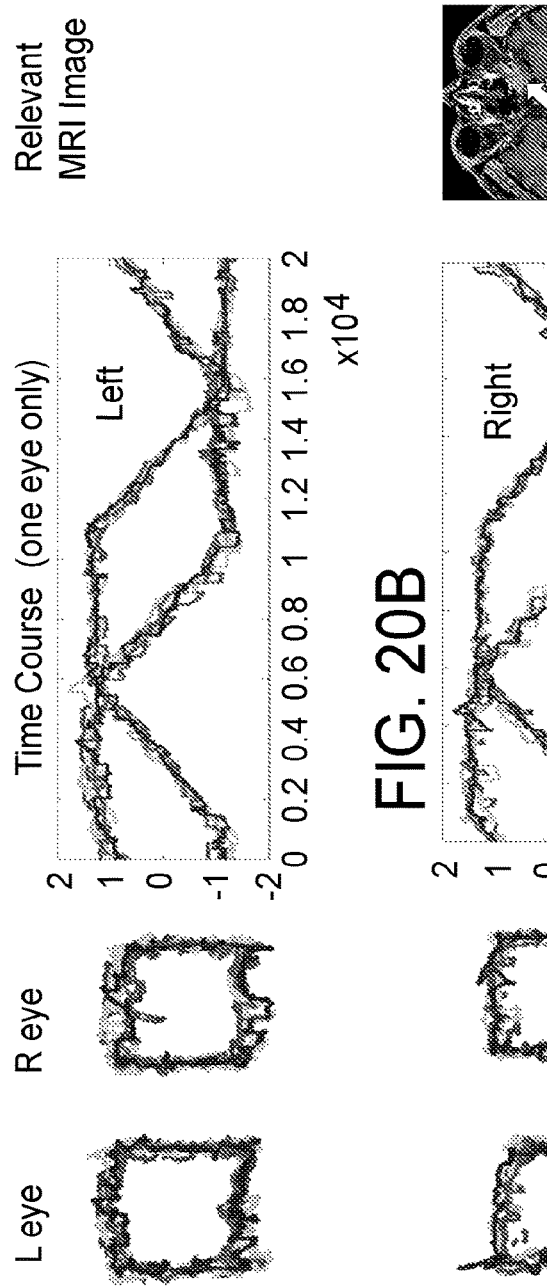
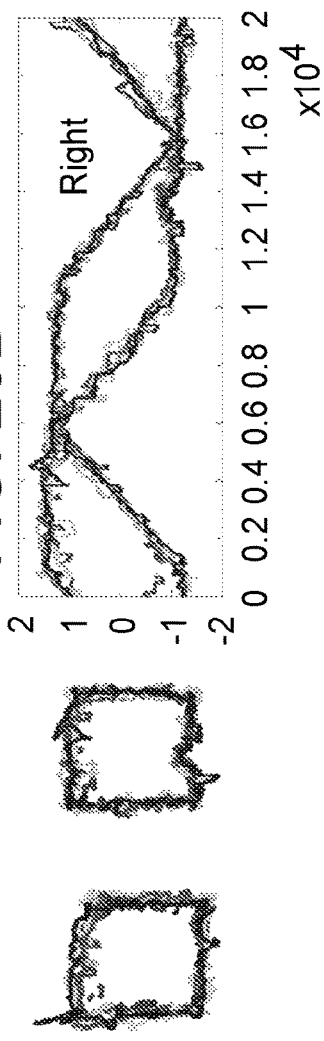
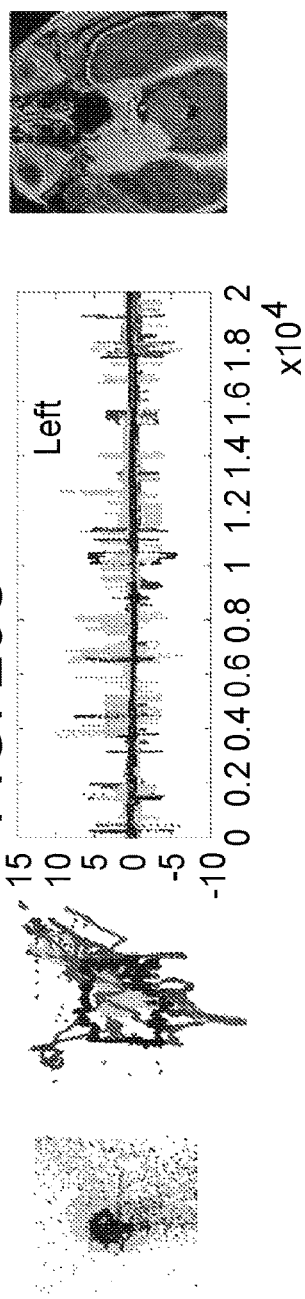
FIG. 20A Time Course (one eye only)
FIG. 20B
FIG. 20C
R eye
L eye
87 yo male with presbyopia astigmatism and cataracts
65 yo male with no light perception in left eye from a tumor
63 yo male with right ophthalmoplegia from tumor
Relevant MRI Image

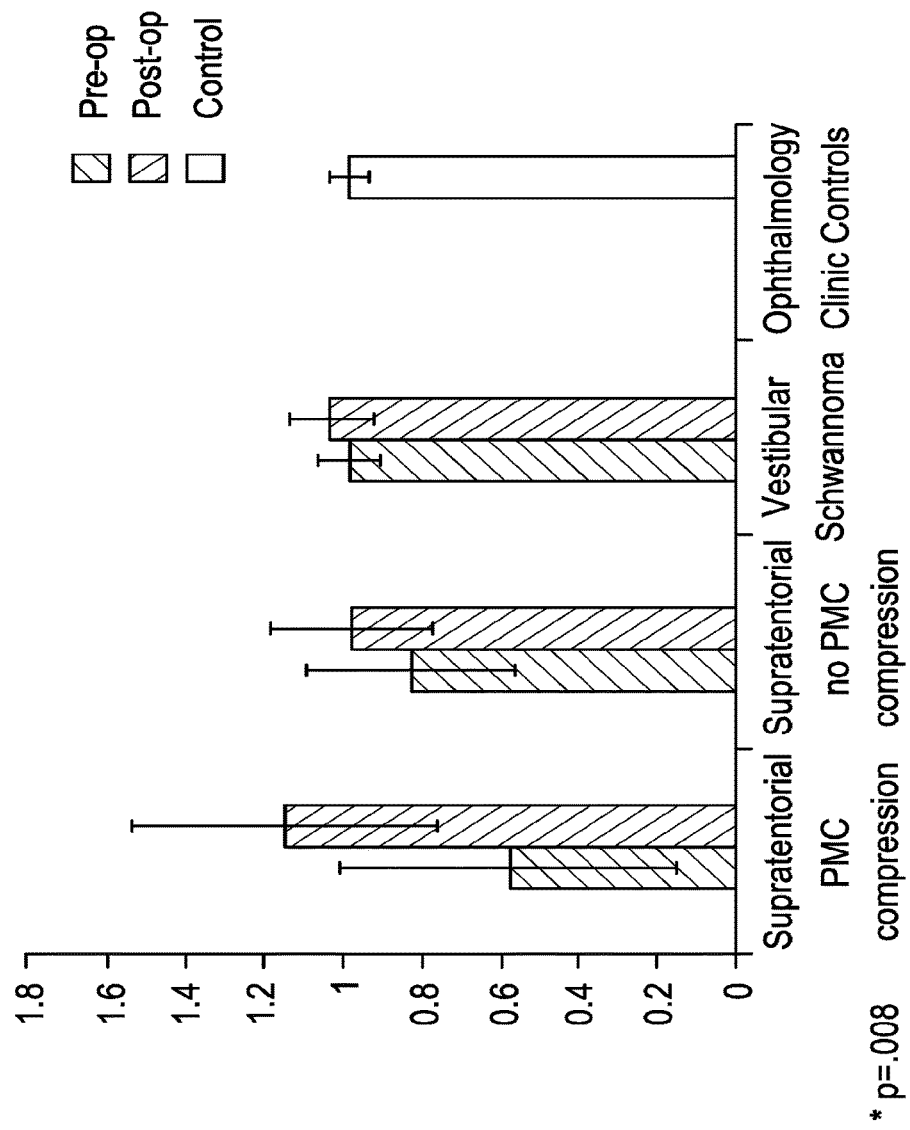

% Decrease in PMC Compression (Contralateral to Eyetracking from Postoperative to Preoperative CT vs. Percent Decrease in Box Aspect Ratio from Postoperative to Preoperative Tracking

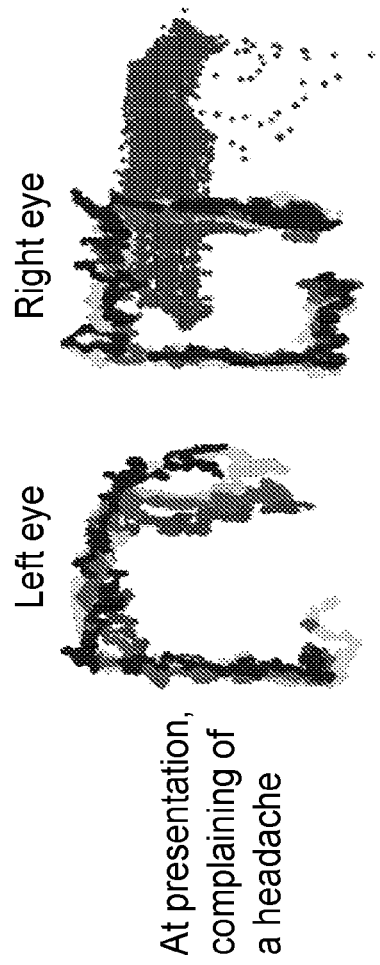
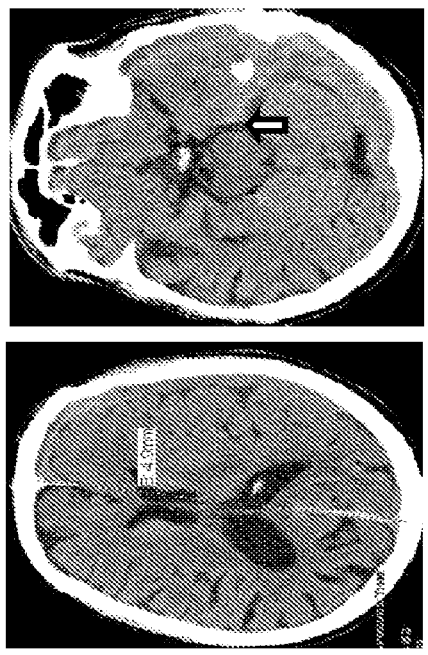
FIG. 22A At presentation, complaining of a headache
FIG. 22B 8 days later, the headache had resolved but then recurred FIG. 23A
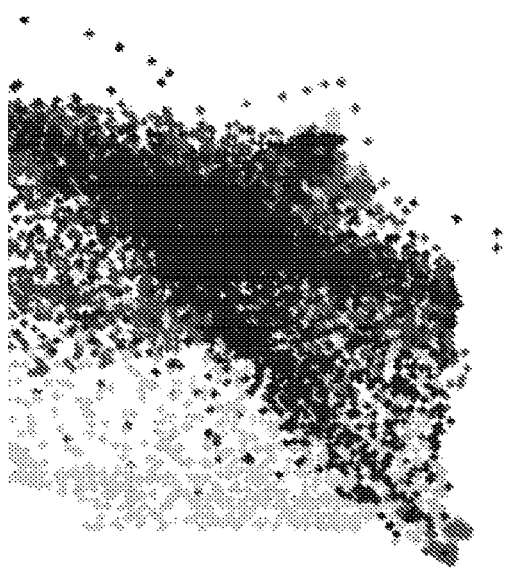
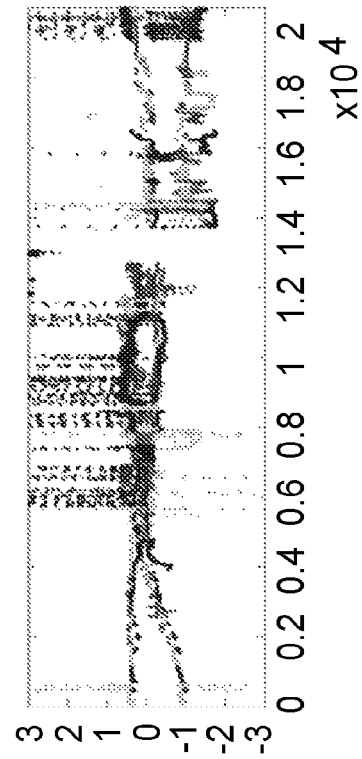
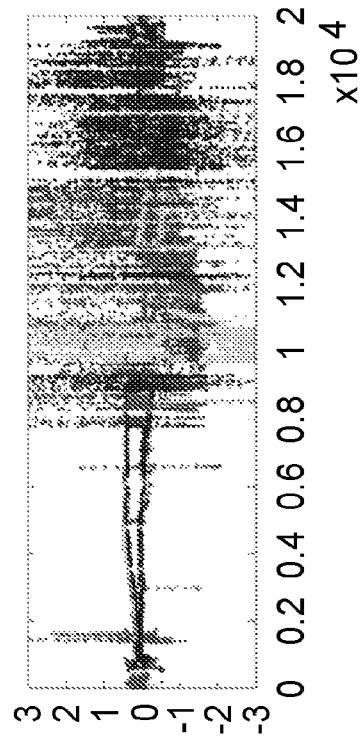

FIG. 23B
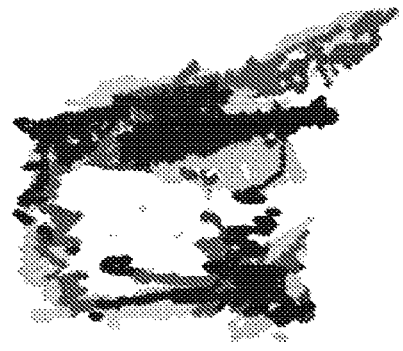
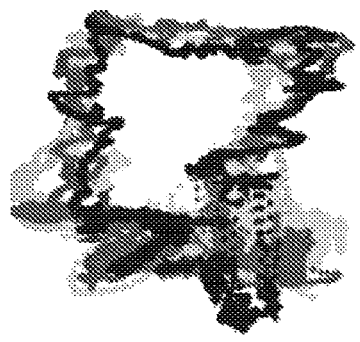
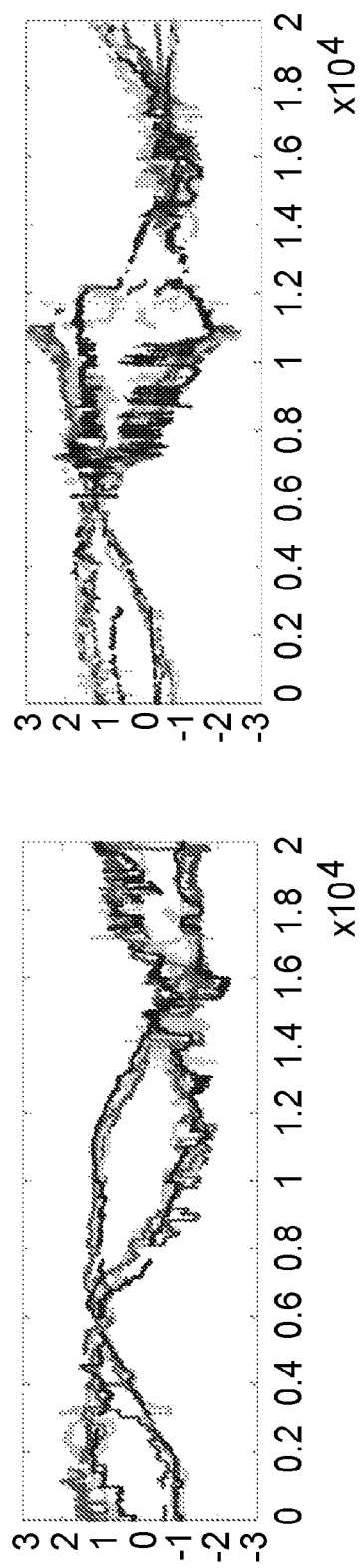

FIG. 23C
Preoperative CT images
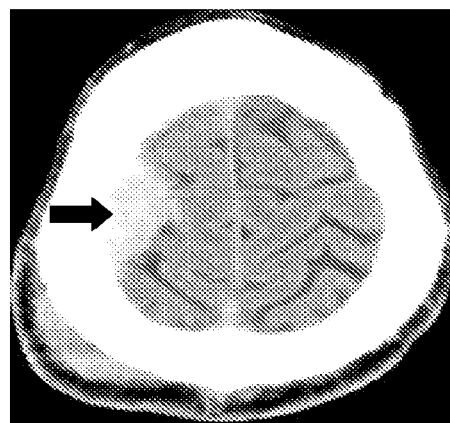
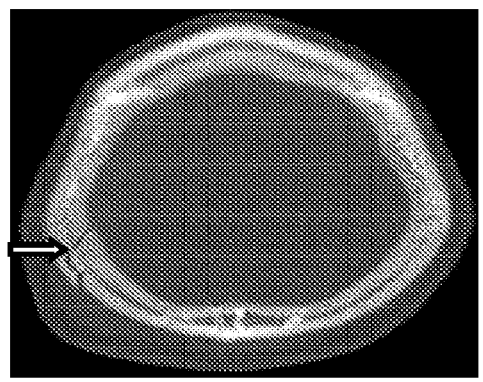
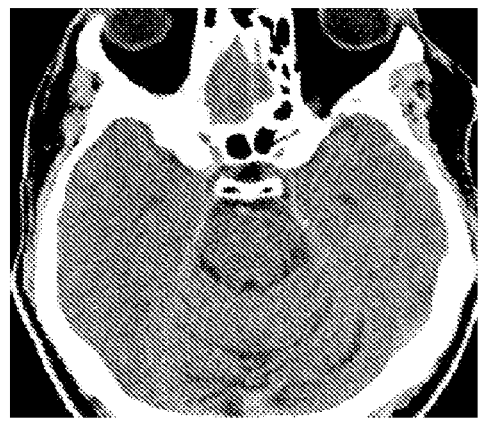

Box height in a normal control = median location of pupil as the aperture traverses the top (in red) minus the bottom (in blue) of the monitor Box height in this patient with an acute epidural hematoma is a negative value since the top (red) Is less than the median of the Bottom (cyan blue)

Preoperative CT scans showing subdural
hematoma and uncal fullness

Preoperative tracking

Left eye            Right eye

FIG. 26A
Preoperative MRI shows the tumor and mass effect on CNIII
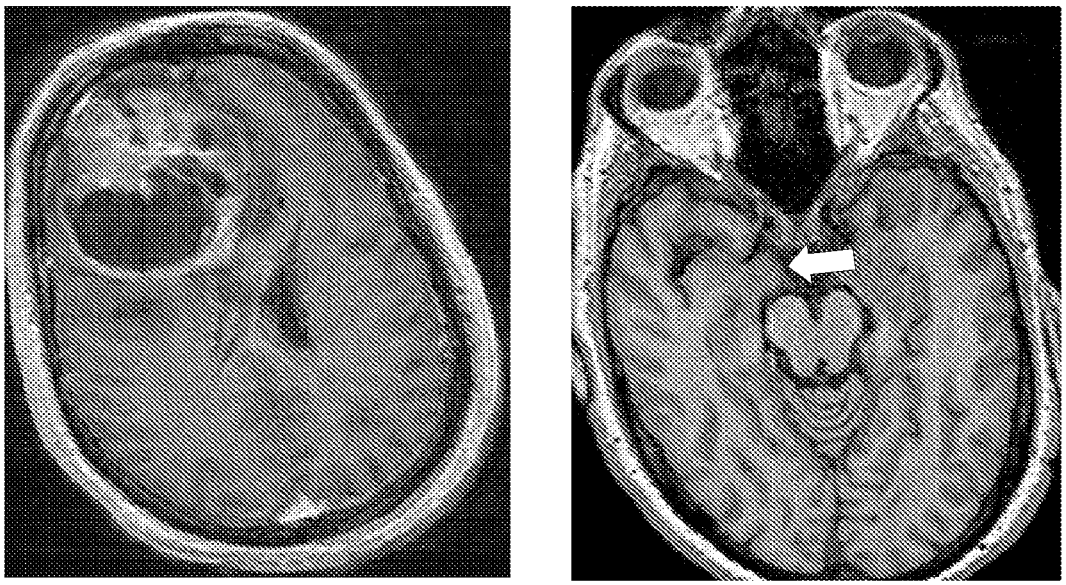
FIG. 26B
Preoperative
Left eye          Right eye
FIG. 26C
2 weeks Postoperative
Left eye          Right eye
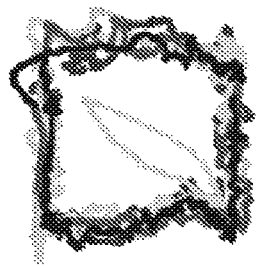 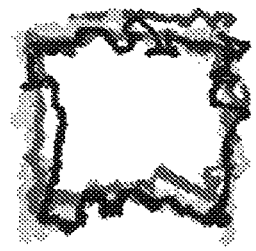

FIG. 27A
Preoperative CT scan shows subdural hematoma and full uncus
FIG. 27B
Preoperative tracking
Left eye                    Right eye
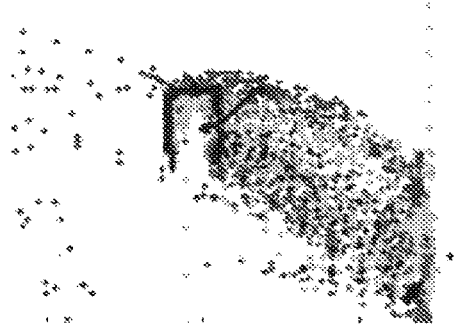 

3 days before cyst
drainage (above)

Left eye         Right eye

One month after tumor
resection (below)

Left eye         Right eye

FIG. 29A
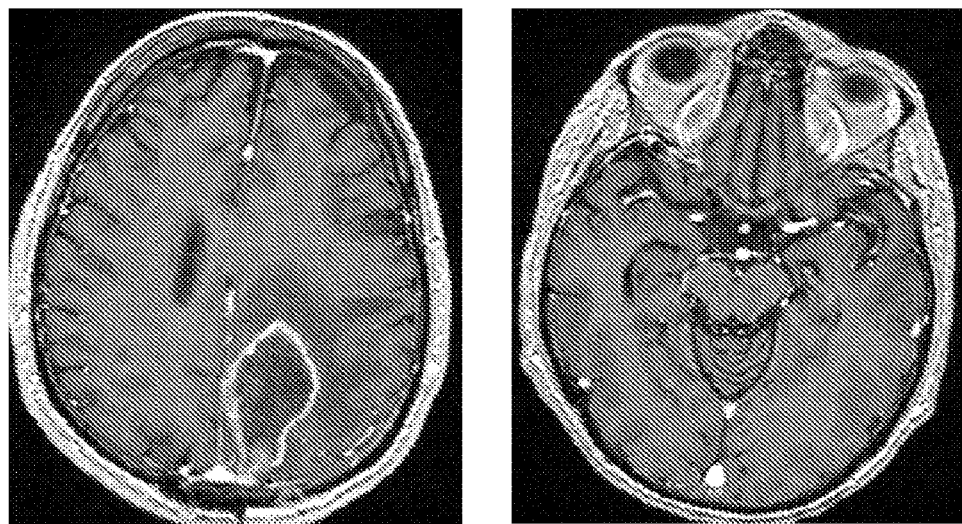
FIG. 29B
Preoperative
Left eye
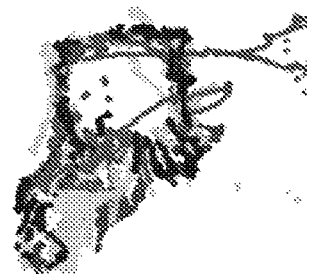
Right eye
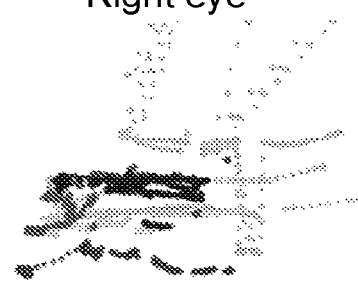
FIG. 29C
One week postoperative
Left eye
Right eye

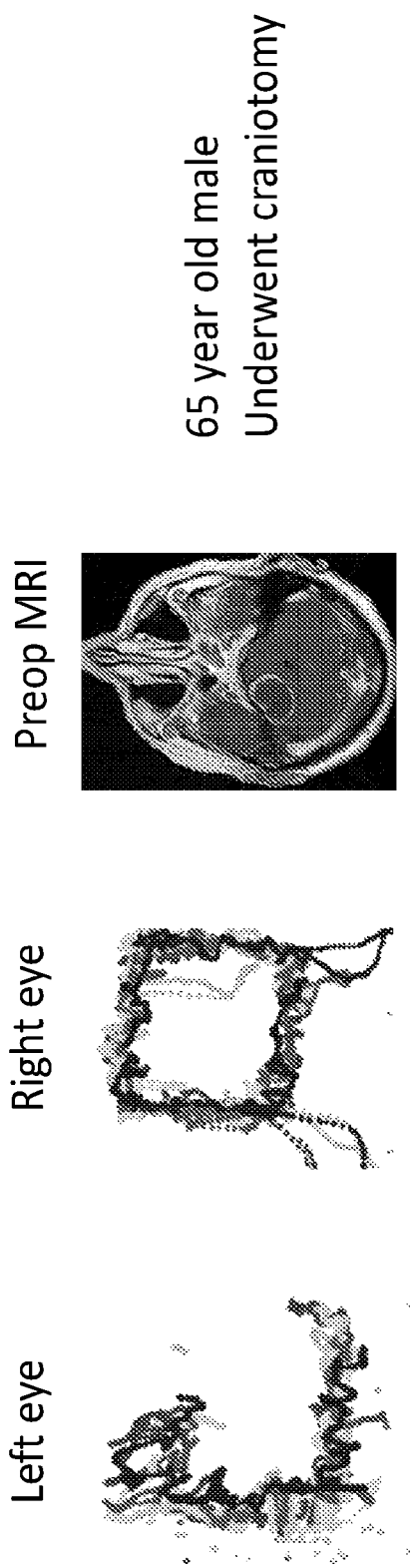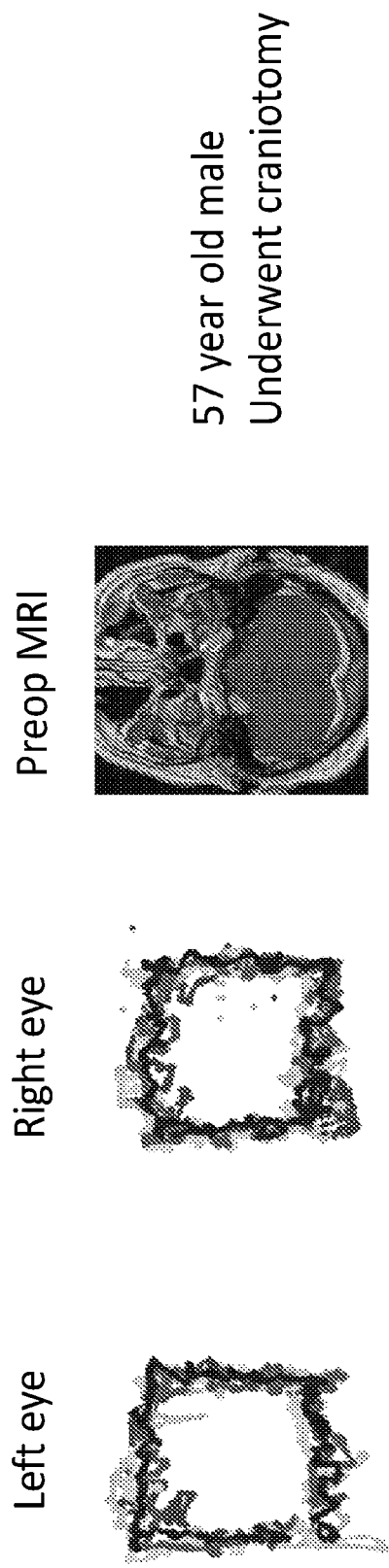

FIG. 30C Preop MRI — 56 year old male with a left 13x9 mm acoustic neuroma underwent gamma knife radiation
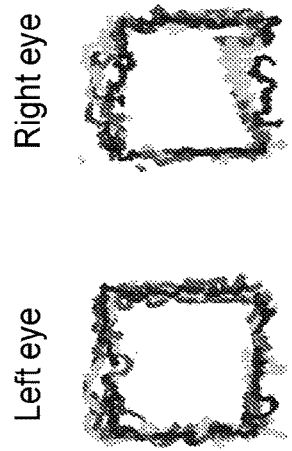
Right eye  Left eye
FIG. 30D Preop MRI — 63 year old male electing serial observation
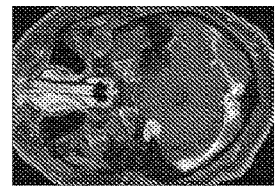
Right eye  Left eye
FIG. 30E Preop MRI — 44 year old male Underwent craniotomy
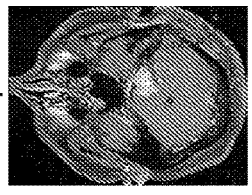
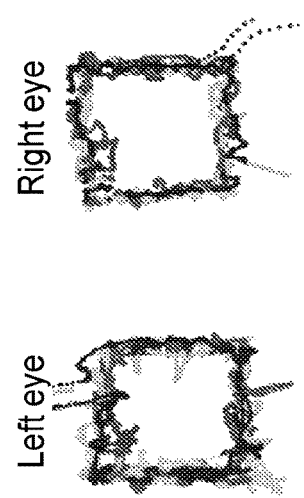
Right eye  Left eye

FIG. 31
Normal Pressure Hydrocephalus Case: 68 yo male presented with 2 falls after a stroke and noted to have progressive gait abnormality. Gait was dramatically improved by a large volume LP. The opening pressure was less than 3 cm. A shunt was placed.
preop
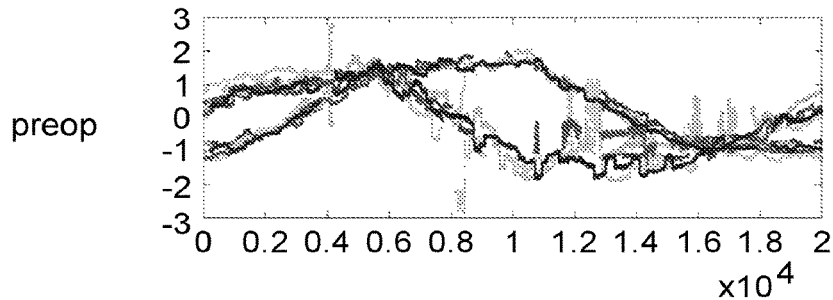
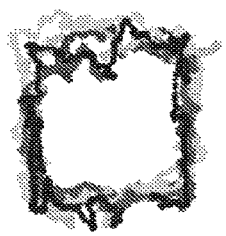
postop
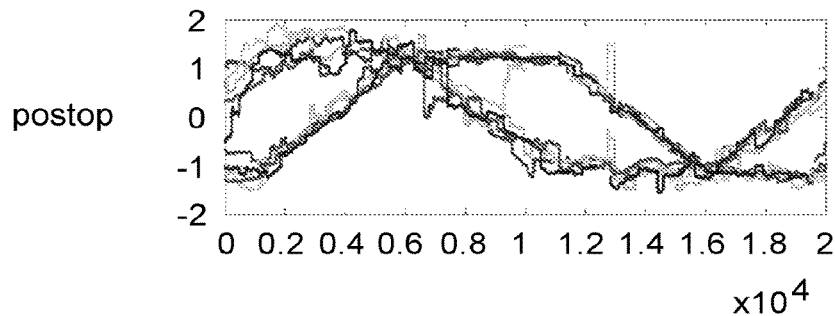

57 yo construction worker with increasing gait disturbance and memory problems progressive over 5 years. Fired from his job after falling. MMSE improved by 3 points, as did gait after a large volume LP.

FIG. 34
Serial tracking of a 57 year old male with multiple sclerosis and bilateral optic neuropathy
Left 20/70    Right 20/150

FIG. 35
56 yo diabetic male with longstanding horizontal diplopia due to a right VIth nerve palsy
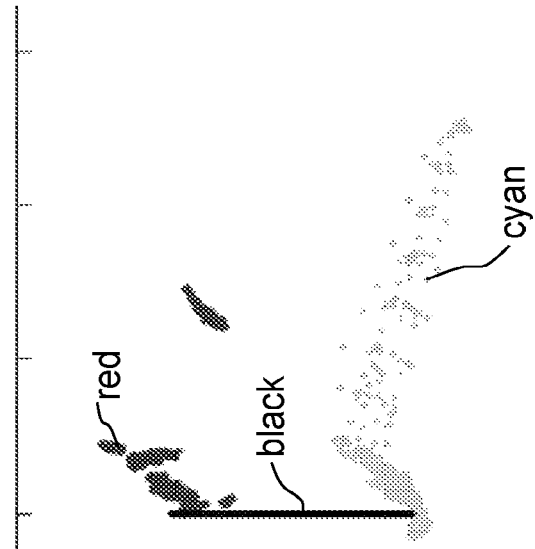
Key: top =red, bottom = cyan, height = black

FIG. 36
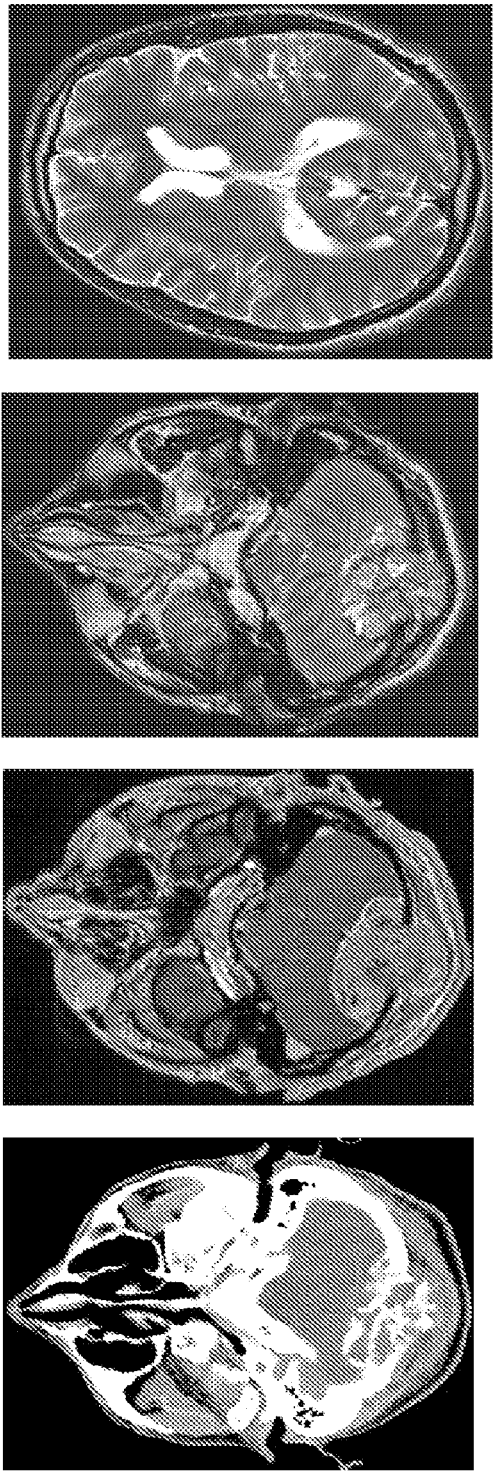
54 yo male with poorly differentiated papillary carcinoma, presented with a tender mass on the back of his head and a progressive headache
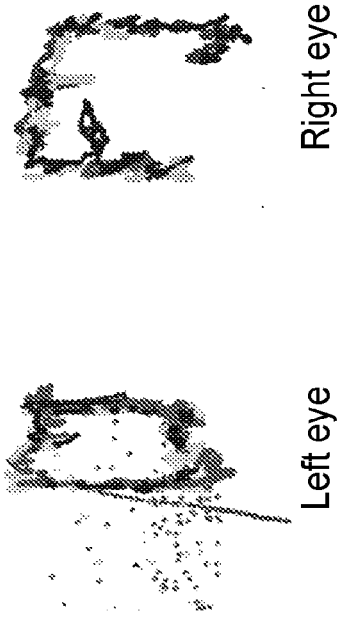
Ophthalmology: "no signs of papilledema"
Right eye
Left eye FIG. 37
Postoperative day 1
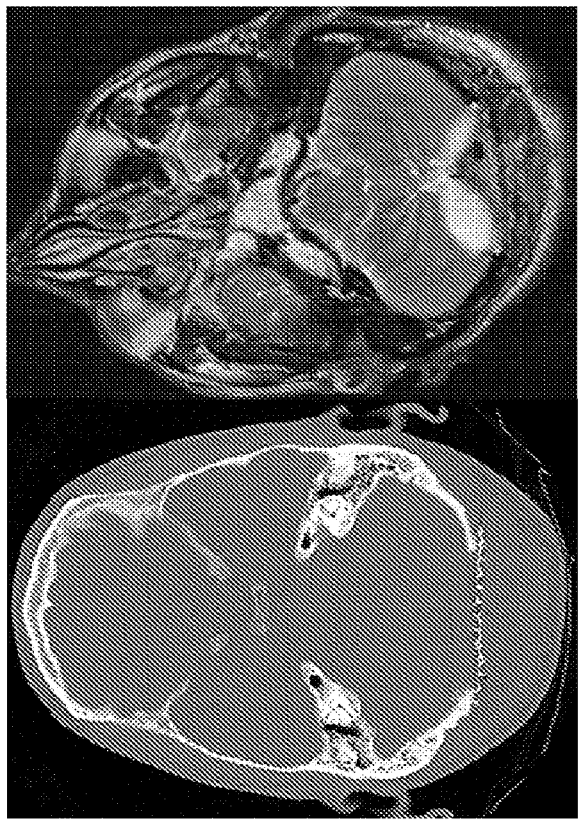
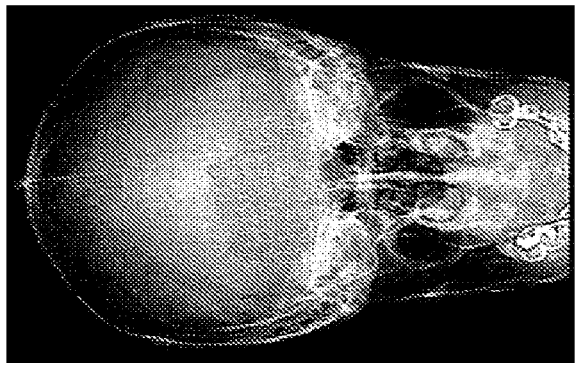
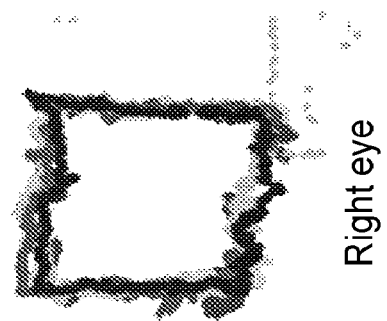
Right eye
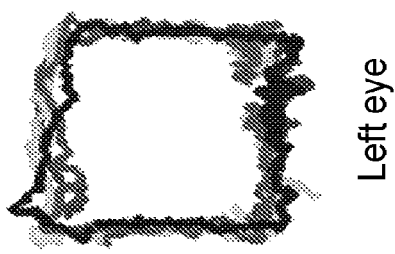
Left eye

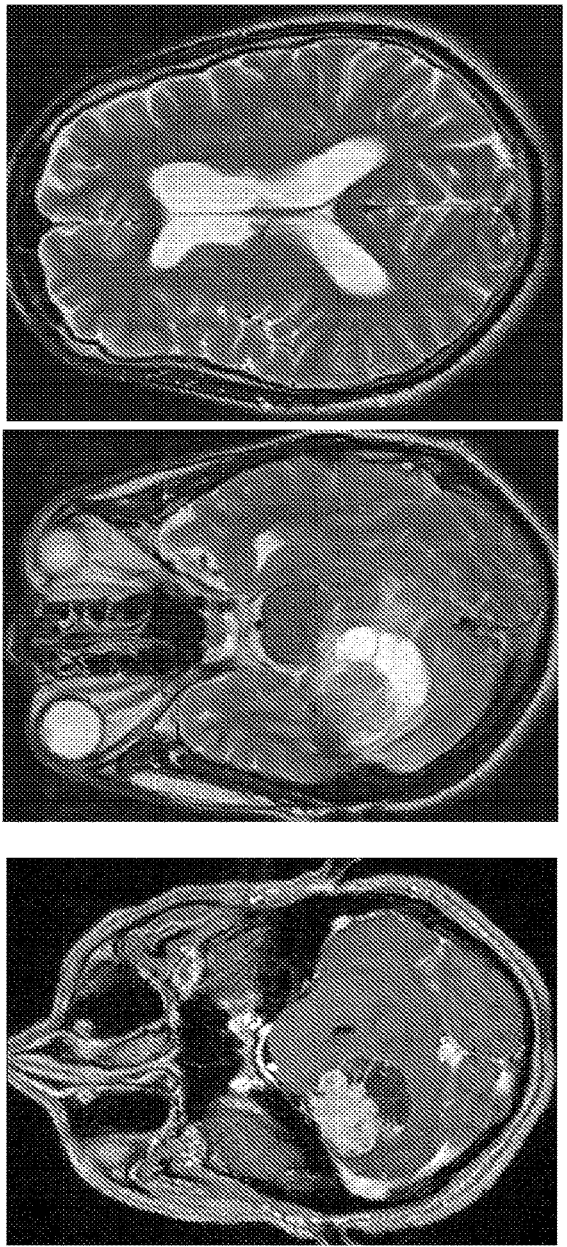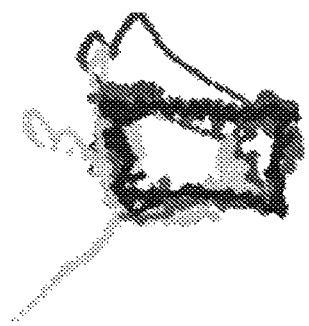
FIG. 38
56 yo male with lung mass, headaches; Ophthalmology: no evidence of papilledema
Right eye
Left eye Postoperative Day 1

25 year old female presented with blurry vision – optic neuritis

Elevated Intracranial Pressure Case: 63 yo male 2 ppd smoker, no medical care >40 years; presented with slow speech and gait; mild confusion 2 weeks after a flu-like illness. L pronator drift and neglect, Ox1, extra-ocular movements appeared grossly intact Immediately before the OR; after 10 mg decadron Every six hours x 4doses;
No left drift, neglect, oriented to person, place Eye movements seemed grossly intact Papilledema gone -

FIG. 46
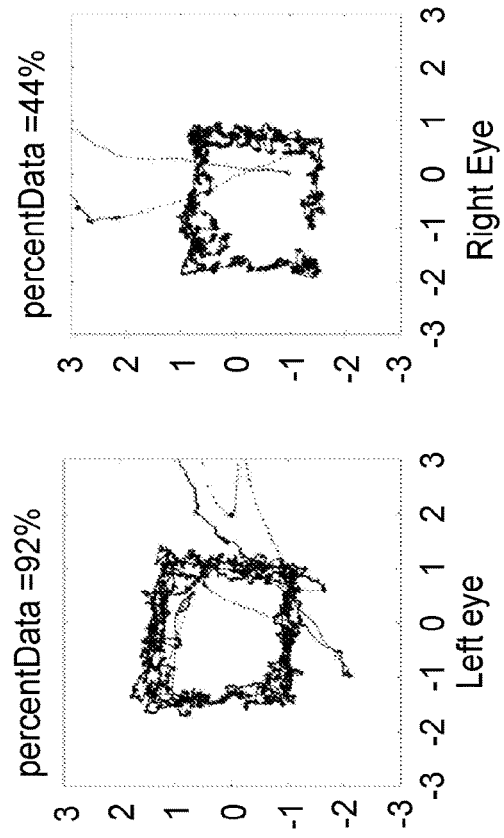
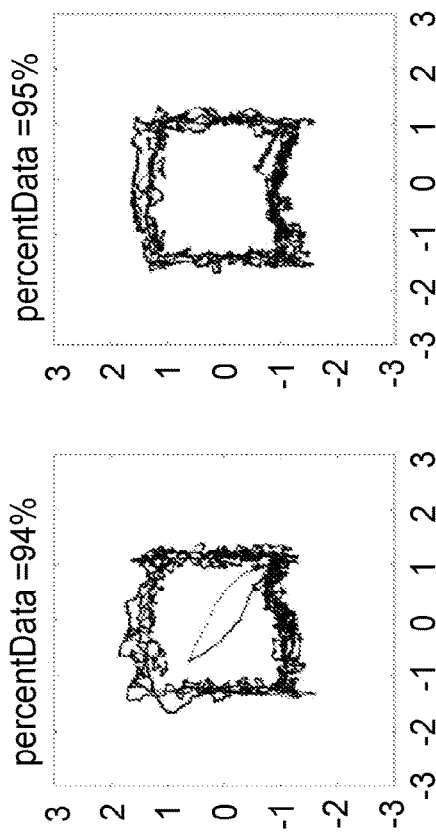
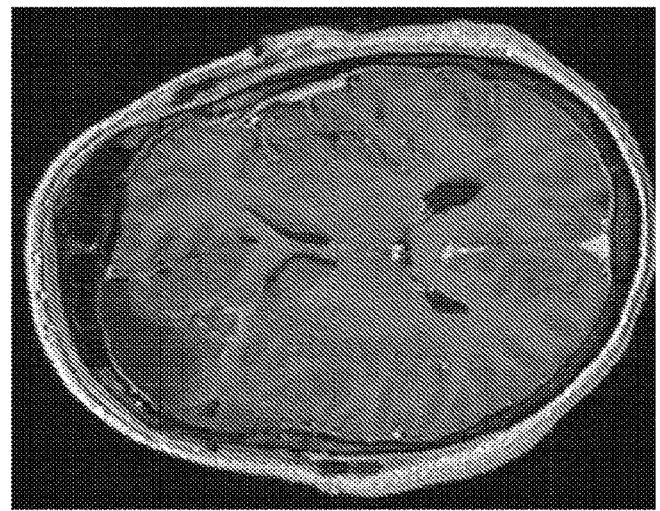

METHODS AND KITS FOR ASSESSING CENTRAL NERVOUS SYSTEM INTEGRITY

CROSS REFERENCE TO RELATED APPLICATIONS

This application is a divisional application of U.S. Patent Application Ser. No. 16/260,379, filed Jan. 29, 2019, which is a divisional of U.S. Patent Application Ser. No. 15/429,413, filed Feb. 10, 2017, now U.S. Patent No. 10,219,694, which is a continuation of U.S. Patent Application Ser. No. 14/387,892, filed Sep. 25, 2014, now U.S. Pat. No. 9,642,522, which is a U.S. National Stage of International Application No. PCT/US2013/033672, filed Mar. 25, 2013, which claims the benefit of priority to U.S. Provisional Application No. 61/615,463 filed Mar. 26, 2012 and U.S. Provisional Application No. 61/710,213 filed Oct. 5, 2012, the disclosures of which are herein incorporated by reference in their entireties.

FIELD OF THE INVENTION

The present invention relates to methods and kits for assessing physiologic function of the cranial nerves, screening for, diagnosing, and quantitating the extent of elevated intracranial pressure, transtentorial herniation as manifested by cranial nerve III palsy, concussion, normal pressure hydrocephalus, posterior fossa mass effect as manifested by cranial nerve VI palsy, optic neuropathy, and locating and monitoring progression of intracranial lesions and disease processes.

BACKGROUND OF THE INVENTION

If untreated, acute elevations in intracranial pressure (ICP) due to hydrocephalus, brain injury, stroke, or mass lesions can result in permanent neurologic impairment or death. Hydrocephalus, the most common pediatric neurosurgical condition in the world, has been well studied as a model for understanding the impact of elevated ICP. The visual disturbances and diplopia associated with hydrocephalus were first described by Hippocrates in approximately 400 B.C. (Aronyk, *Neurosurg Clin N Am.* 1993; 4(4):599-609). Papilledema, or swelling of the optic disc, and its association with elevated ICP was described by Albrecht von Graefe in 1860 (Pearce, *European neurology* 2009; 61(4):244-249). In the post-radiographic era, acute and chronic pathology of the optic nerve and disc (cranial nerve II), and of ocular motility (cranial nerves III, IV and VI) are well characterized in hydrocephalic children (Dennis et al., *Arch Neurol.* October 1981; 38(10):607-615; Zeiner et al., *Childs Nerv Syst.* 1985; 1(2):115-122 and Altintas et al., *Graefe's archive for clinical and experimental ophthalmology=Albrecht von Graefes Archiv fur klinische und experimentelle Ophthalmologie.* 2005; 243(12):1213-1217). Visual fields may be impaired in treated hydrocephalus (Zeiner et al., *Childs Nerv Syst.* 1985; 1(2):115-122), and there is increased latency in light-flash evoked responses in acutely hydrocephalic children relative to their post treatment state (Sjostrom et al., *Childs Nerv Syst.* 1995; 11(7):381-387). Clinically apparent disruption of ocular motility may precede computed tomography (CT) findings in some acute hydrocephalics (Tzekov et al., *Pediatric Neurosurgery* 1991; 17(6):317-320 and Chou et al., *Neurosurgery Clinics of North America* 1999; 10(4):587-608).

Several potential mechanisms may contribute to cranial nerve dysfunction due to hydrocephalus. The optic nerve (II) is most frequently analyzed because it can be visualized directly with ophthalmoscopy, and indirectly with ultrasound. Edema of the optic nerve appears earlier than ocular fundus changes, and resolves after treatment of elevated ICP (Gangemi et al., *Neurochirurgia* 1987; 30(2):53-55). Fluctuating elevated neural pressure leads to impaired axonal transport along the optic nerve after as little as 30 minutes in a rabbit model (Balaratnasingam et al., *Brain Research* 2011; 1417:67-76). Axoplasmic flow stasis and intraneuronal ischemia may occur in the optic nerve exposed to chronically elevated ICP (Lee et al., *Current Neurology and Neuroscience Reports.* Feb. 23, 2012).

At present, the diagnosis of elevated intracranial pressure relies on history, physical exam, radiographic imaging, and possibly direct invasive assessment of the subarachnoid space or structures contiguous with it via cannulated needle tap of a shunt or monitoring device placement. Chemical dilatation of the pupil to assess for papilledema may be unpleasant for the examinee, relies on the experience of the examiner and obfuscates further examination of the pupillary reflex. Papilledema is not always a sensitive marker for hydrocephalus, and in one study was present in as few as 14% of patients with a shunt malfunction (Nazir et al., *J Aapos* 2009; 13(1):63-66) consistent with the relatively short intracranial course of II relative to cranial nerves III and IV. Compartmentalization of subarachnoid spaces is hypothesized to explain why papilledema may be present in a patient without elevated ICP, and not occur in patients with elevated ICP (Killer et al., *Clinical & Experimental Ophthalmology* 2009; 37(5):444-447).

Automated eye movement tracking has been used for marketing and advertising research, the development of assistive devices for immobile individuals, and for video games. Calibration of the device requires the subject to have relatively intact ocular motility that implies function of cranial nerves II (optic), III (oculomotor), IV (trochlear) and VI (abducens) and their associated nuclei as well as sufficient cerebral function to enable cognition and volition for calibration. Calibrated eye movement tracking has been utilized to detect cognitive impairment secondary to axonal shearing after mild traumatic brain injury (Lee et al., *Brain research.* 2011; 1399:59-65; Contreras et al., *Brain Research* 2011; 1398:55-63 and Maruta et al., *The Journal of Head Trauma Rehabilitation* 2010; 25(4):293-305).

Others have successfully demonstrated the clinical applications of eye movement data (Lee et al., *Brain Research.* 2011; 1399:59-65; Contreras et al., *Brain Research* 2011; 1398:55-63; Maruta et al., *The Journal of Head Trauma Rehabilitation* 2010; 25(4):293-305). Trojano et al., *J Neurol* 2012; (published online; ahead of print) recently described uncalibrated eye movement measurements in a population of minimally conscious and persistently vegetative patients. They report data from 11 healthy control subjects evaluating chronic disorders of consciousness, not acute changes in intracranial pressure. They sample eye movements at 60 Hz rather than 500 Hz, effectively reducing the power of their data 100-fold, and they report differences in on-target and off-target fixations between the groups without spatially calibrated data. Moreover, they use static stimuli moving in a quasi-periodic way.

All publications, patent applications, patents and other reference material mentioned are incorporated by reference in their entirety. In addition, the materials, methods and examples are only illustrative and are not intended to be limiting. The citation of references herein is not to be construed as an admission that the references are prior art to the present invention.

SUMMARY OF THE INVENTION

In a first aspect, the invention provides methods for assessing central nervous system integrity in a subject by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

In a second aspect, the invention provides methods for detecting or screening for reduced or impaired cranial nerve function or conduction in a subject by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

The cranial nerve may be, for instance, one or more of II, III, IV or VI. The reduced or impaired cranial nerve function or conduction may be unilateral or bilateral and may be caused all or in part by increased intracranial pressure, and it may be caused all or in part by a localized or diffuse lesion or disease process. The reduced function of the cranial nerve may be due to pathology impacting the nerve itself, its associated nucleus or supranuclear inputs.

In a third aspect, the invention provides methods for detecting, diagnosing or screening for increased intracranial pressure in a subject by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

The increased intracranial pressure may be, for instance, 10%, 20%, 30%, 50%, 100%, 200%, 300% or more greater than normal.

In a fourth aspect, the invention provides methods for detecting, diagnosing, monitoring progression of or screening for a disease or condition featuring increased intracranial pressure by
- a) Tracking eye movement of a subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

The disease or condition featuring increased intracranial pressure may be, for instance, a trauma, cerebrovascular accident (CVA), an aneurysm or other vascular lesion, a tumor whether malignant or benign, an infectious process, an inflammatory disease, a disruption of venous drainage, a pseudotumor, hydrocephalus or idiopathic.

In a fifth aspect, the invention provides methods for detecting, diagnosing or screening for concussion by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

In a sixth aspect, the invention provides methods for detecting, diagnosing or screening for transtentorial herniation by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

In a seventh aspect, the invention provides methods for quantifying the severity of normal pressure hydrocephalus, detecting or screening for shunt malfunction or optimizing valve pressure for treating normal pressure hydrocephalus by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

In a eighth aspect, the invention provides methods for detecting or evaluating posterior fossa mass effect by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

In a ninth aspect, the invention provides methods for detecting, screening for or diagnosing a disorder that impedes conductance through the optic disc or optic nerve by
- a) Tracking eye movement of the subject;
- b) Analyzing eye movement of the subject;
- c) Comparing eye movement of the subject to eye movement of a control or to the subject's baseline normative eye movement; and
- d) Identifying the subject as having eye movement significantly different from the control or the subject's baseline normative eye movement.

In a tenth aspect, the invention provides a kit useful for detecting or screening for reduced or impaired cranial nerve function or conduction, useful for detecting, diagnosing or screening for increased intracranial pressure, or useful for detecting, diagnosing, monitoring progression of or screening for a disease or condition featuring increased intracranial pressure containing a device for tracking eye movement, one or more means for analyzing eye movement tracking data such as, for instance, an algorithm or computer program, and instructions. Processing eye movement observations, making measurements of eye movement observations, determining distributions of values measured and performing statistical tests may all be accomplished using suitable computer software that may be included in such a kit.

In a eleventh aspect, the invention provides a computer system. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

According to the methods described, tracking eye movement may be performed using any suitable device such as, for example, an Eyelink® 1000 monocular eye tracker (500 Hz sampling, SR Research). The eye tracking movement samples may be obtained at any suitable frequency, such as for instance, 10 Hz to 10,000 Hz or more. The subject may be positioned an appropriate distance from the device, such as, for example, 10, 20, 30, 40, 50, 55, 60, 70, 80, 90 cm or more, or even a meter or more from the device screen. In some instances, the subject's head may be stabilized, such as, for instance by using a chinrest or similar stabilizing mechanism. The subject may be seated or reclining. Preferably, the presentation monitor of the device is adjusted so as to substantially match the subject's gaze direction. The tracking eye movement may be performed for a total of, for example, 30, 60, 90, 120, 150, 180, 200, 220, 240, 270, 300, 330, 360, 400, 450, 500 seconds or more. As such, according to the methods provided, 1,000, 5,000, 10,000, 20,000, 25,000, 50,000, 75,000, 100,000, 150,000, 200,000, 250,000, 300,000 or more samples of eye position may be obtained.

According to the methods described, analyzing eye movement may be performed by any suitable means. In some instances, a stimulus and an analysis stream are provided that allows interpreting raw eye position data. In some instances, an algorithm may be provided for looking at pupil position directly thereby yielding information about ocular motility. Preferably, a device is adapted into a novel mobile system that may analyze eye movement close in time or substantially concurrent to the eye movement itself.

According to the methods described, eye movement may be tracked in response to a visual stimulus. In some instances, the visual stimulus may be, for instance, a video such as a music video that may move, for instance clockwise, along the outer edge, of a computer monitor. In some instances, such a video may be provided starting at the upper or lower, left or right hand corners, of a screen. The visual stimulus such as a video, e.g. a music video, may be provided in a substantially square aperture with an area of approximately 10, 12, 14, 16, 18, 20, 25, or degrees, for example, approximately 1/10, 1/8, 1/6, 1/5, 1/4, 1/3, 1/2 of the size of the screen or so. The visual stimulus, such as, for example a music video, may play substantially continuously during the eye movement tracking, and it may in some instances move across the screen at a relatively or substantially constant speed. For instance, such a visual stimulus, for instance, a music video may cover each edge of a monitor in about 2, 5, 10, 15, 20, 30, 45 or 60 seconds or so. Therefore, in some instances, a full cycle may take, for instance, 10, 20, 30, 40, 50, 60, 75, 100, 120, 150, 180 seconds or so. Multiple cycles of such a visual stimulus, for instance a music video may be played, for instance, one, two, three, four, five, six, seven, eight, nine, ten, twelve, fifteen, twenty or more full cycles. As such, the visual stimulus may be provided, the eye movement may be tracked, in effect, in some instances the video may be played for a total of, for example, 30, 60, 90, 120, 150, 180, 200, 220, 240, 270, 300, 330, 360, 400, 450, 500 seconds or more. In instances where the visual stimulus is in the form of a video, a countdown video may be played in the starting position for, for instance, 5, 10, 15, 20, 25, or 30 seconds or more before beginning the visual stimulus, e.g. video, to provide subjects sufficient time to orient to the visual stimulus. Likewise, the visual stimulus, for instance a video, may be continued for an addition 2, 5, 10, 15, 20, 30, 45 or 60 seconds or so after the eye movement tracking is performed to reduce or substantially avoid boundary effects.

According to the methods described, comparing eye movement of the subject to a control may be performed by analyzing data. Data from the tracking eye movement may provide an indication of whether an individual subject's ocular motility differs from that of healthy controls. Comparing eye movement of the subject to a control may feature generating scatterplots. Comparing eye movement of the subject to a control may feature plotting the horizontal eye position along one axis and vertical eye position along an orthogonal axis. Such comparing eye movement of the subject to a control may feature generating, plotting pairs of (x,y) values, for instance, 50,000, 100,000 or more pairs of values (x,y). Such pairs of values (x,y) may be plotted representing, for instance, the two components of the instantaneous angle of pupil reflection (horizontal, vertical) over a period of time, for instance, 100 or 200 seconds or more.

As such, comparing eye movement of the subject to a control may feature generating figures substantially resembling boxes that reflect the trajectory traveled by the visual stimulation, such as when it moves across a screen. In healthy controls, these figures substantially resembling boxes may look like, for instance, substantially equilateral rectangles or squares, reflecting the trajectory traveled by the visual stimulus across a screen. In instances of neurological damage or increased intracranial pressure, such figures may not substantially resemble a box, a rectangle or a square. In fact, in some instances, the cranial nerve having reduced or impaired function or conduction may be identified. In some instances, the figures generated that reflect the trajectory traveled by the visual stimulation may demonstrate abnormal distribution of or absence of normal plotting pairs in particular areas. Increased variability along the y-axis may for example reflect cranial nerve II dysfunction. Decreased variability along the y-axis, or decreased height to width ratio may reflect CN III dysfunction. Increased height to width ratio may reflect CN IV or VI dysfunction. The height of the box may be mathematically determined by assessing the position of the pupil as the video traverses the top and bottom of the presented visual stimulus. This "actual" height may be different from the perceived height mathematically, since the perceived height can represent aberrant pupillary motion due to the patient's ocular motility dysfunction. The integrity of the box walls may also be indicative of other types of dysfunction. Both cranial nerve palsies and mass effect may cause defects in box trajectory. Supratentorial mass lesions and CN III defects may impact the top and/or bottom of the box. Infratentorial mass lesions or CN VI palsies may impact the sides of the box. For instance, in the case of the left eye, the upper left quadrant of the figure may reflect activity, function or conduction of cranial nerves III and VI, the lower left quadrant of the figure may reflect activity, function or conduction of cranial nerves III and IV, while the upper right quadrant and the lower right quadrants may reflect activity, function or conduction of cranial nerve III. In the case of the right eye, the upper and lower left quadrants of the figure may reflect activity, function or conduction of cranial nerve III, the lower right quadrant of the figure may reflect activity, function or conduction of cranial nerve III, while the upper right quadrant and the lower right quadrant may reflect activity, function or conduction of cranial nerves IV and VI.

Comparing eye movement of the subject to a control may feature determining the distribution of certain measurements in the control population and comparing the subject with these control distributions. In such instances, visual stimulus trajectory may be divided into four time components, for instance, two, three, four, five, six or more repetitions of the first few, for instance, 2, 5, 10, 15, 20 or so seconds of each rotation cycle. In such instances, comparing eye movement of the subject to a control may feature evaluating such variables as the relative variance in each arm, and the relative integrity of each arm.

Comparing eye movement of the subject to a control may also feature measuring the integrity of each subject's values. In instances featuring generating figures substantially resembling boxes that reflect the trajectory traveled by the visual stimulation, such as when it moves across a screen, the sides or arms of the figures (e.g. the top of the box and the bottom of the box) may be z-scored using the mean and standard deviation calculated from the control population. The resulting score may indicate how different the subject's values are compared with the control values, such as, for instance, in units of standard deviations.

According to the methods described, identifying the subject as having eye movement significantly different from the control may be performed using a z-score. Because 95% of all values in a normal distribution lie within two standard deviations of the mean, a z-score of 2 may be used as a significance threshold. Subjects with z-scores above, for instance, 2 in either or both, or 1, 2, 3, or 4 sides or arms of the figures may be judged to have significant disturbances of ocular motility.

Identifying the subject as having eye movement significantly different from the control may feature determining relative variance. In some instances, multiple such as 1,000, 2,000, 3,000, 5,000, 10,000, 20,000 or more point distributions may be generated by, for instance, taking multiple samples from a multiple number of values randomly chosen with replacement from the multiple control values. For each subject, the relative variance in either or both, or 1, 2, 3, or 4 sides or arms of the figures may be compared respectively with the corresponding control distribution, and the percent of the control distribution with variance below that of the test value may be determined. A p-value of 0.05 a widely accepted measure of statistical significance corresponds to 95% of control values falling below the test value. In such instances, subjects with variance higher than 95% of the values in the control distributions may be determined to have significant disturbances of ocular motility. The video may also move in other trajectories not resembling a rectangle, such as a triangle, circle or linear or nonlinear trajectories. As long as the trajectories can be resolved into vectors along Cartesian coordinates (horizontal vertical or x,y) the same principles will apply. In short, any trajectory (e.g. any shape, or line, or curve, etc.) studied over time may provide information about Central Nervous System function or dysfunction.

BRIEF DESCRIPTION OF THE FIGURES

FIGS. 1A and D are the results obtained from neurotypical control observers.

FIG. 2(A, B, C) provides examples of eye movement recordings taken during repeated viewings by the same patient over time. The first column indicates the date. The second column provides an image of an axial slice through the patient's brain on that date. The third and fourth columns provide scatterplots for the eye movements recorded in the left and right eyes, respectively.

FIG. 7 demonstrates the eye movement tracking of a 77 year old male who entered the hospital after two syncopal episodes resulting in falls. He denied headache and walked around the emergency room, speaking with fluent speech. He was oriented to person, place and time. His extraocular movements appeared intact. Head CT revealed a left sided foramen of Monroe hemorrhage with unilateral hydrocephalus.

FIG. 8 demonstrates the eye movement tracking of an 86 year old male who presented 6 weeks after a fall with headache.

FIG. 9 demonstrates the eye movement tracking of a patient with an intracranial lesion.

FIG. 10 demonstrates the eye movement tracking of a patient with an intracranial lesion. The third nerve is under direct pressure, experiencing palsy and demonstrates a visually apparent massive loss in diagram box height.

FIG. 23 (A, B, C) represents the eye movement tracking of a 62 year old patient with an acute epidural hematoma and bilateral perimesencephalic compression after a fall. The patient presented with a neurologically non-focal examination and CT scan showing a small right frontoparietal epidural hematoma and non-displaced skull fracture. Upon presentation he was verbally appropriate without focal neurologic deficit. A. Pupil size was equal by gross examination and extraocular movements appeared intact when eye movement tracking was performed. Four hours later the patient developed a left pronator drift and intermittent dysarthria. Epidural hematoma evacuation and fracture repair was performed. B. He underwent repeat eye movement tracking on postoperative day 7, which showed persistent abnormality in the same portions of the eye box trajectory, less than preoperative. C. The preoperative CT images are provided.

shows eye movement tracking including box height in a normal control. B. shows the eye movement tracking in this patient.

Figure 25A:
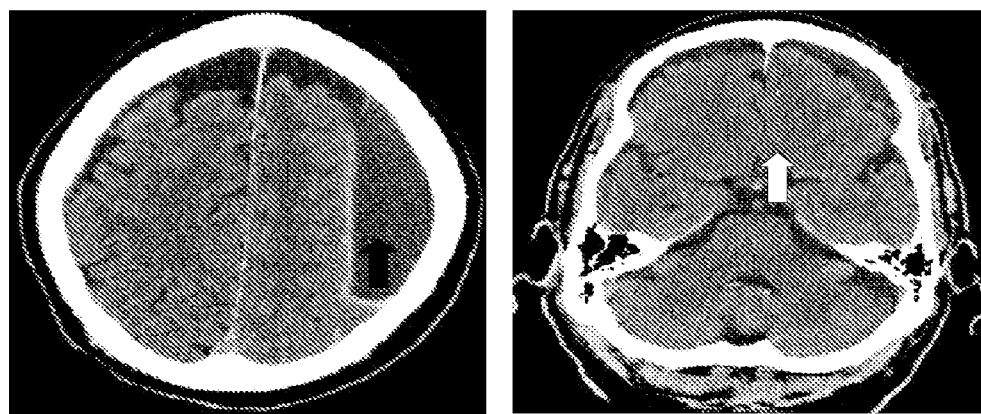
Figure 25B:
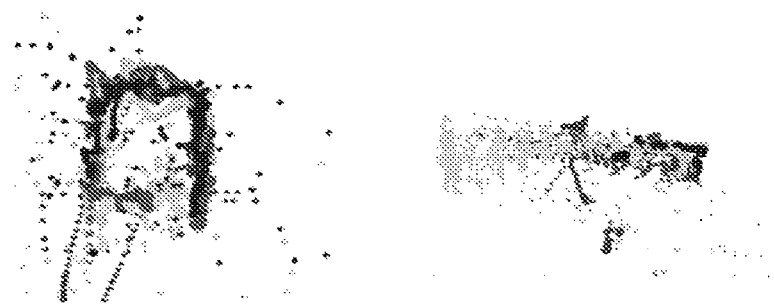

FIG. 25 (A, B) represents the eye movement tracking of a 74 year old diabetic hypertensive male with renal insufficiency, bilateral cataracts and 20/25 vision bilaterally, presented with impaired mobility due to right lower extremity weakness. He denied head trauma but reported having fallen three months prior without hitting his head. On examination he was awake and alert with a right pronator drift and 4/5 right sided hemiparesis of the upper and lower extremities. His left side was intact. His pupils appeared equal and he had intact extraocular motility on examination. A. provides preoperative CT scans showing a subdural hematoma and uncal fullness. Eye movement tracking was performed and the results provided in B. Twist-drill drainage of the subdural hematoma was performed and 130 cc of fluid was extracted. He was discharged to home after inpatient rehabilitation.

FIG. 26 (A, B, C) represents the eye movement tracking of a 63 year old 100 pack-year smoking male who had declined to see a physician for the duration of his adult life, and thus reported no relevant medical or ophthalmologic history, presented to the emergency room with a cough and flu-like illness. On examination he was noted to be disoriented and have a mild L hemiparesis. Pupils were equal and reactive, extraocular movements appeared intact. A. Head CT demonstrated a right frontal mass, and chest radiograph showed a large left upper lobe chest mass. The patient was administered decadron 10 mg po q6 hours and a CT chest/abdomen/pelvis and brain MRI (shown) was obtained. B. Eye movement tracking was performed 48 hours after admission, directly prior to right frontal craniotomy for resection of a moderately well-differentiated squamous cell carcinoma metastasis. A radiographic gross total resection was performed. The patient went home one week after his craniotomy and ultimately underwent radiation therapy to his whole brain. C. provides the results of eye movement tracking 2 weeks postoperative. He declined treatment for the lung mass and expired 7 months after his initial diagnosis.

FIG. 27 (A, B) represents the eye movement tracking of a 63 year old male with diabetes, hypertension, hypercholesterolemia, atrial fibrilliation on coumadin, congestive heart failure, post-traumatic stress disorder, renal failure on dialysis, chronic obstructive pulmonary disease and coronary artery disease. He presented with confusion while receiving hemodialysis for his renal failure. Ophthalmic history was significant for proliferative retinopathy. He had visual acuity of 20/25 in the right eye and 20/40 in the left eye. On physical examination at presentation he was neurologically well, without neglect or pronator drift. Extraocular movements were intact, pupils were equal. A. Head CT demonstrated a right sided mixed-density subdural hemorrhage. B. Eye movement tracking was performed. Coumadin was stopped and fresh frozen plasma administered. Two days after presentation twist-drill drainage was performed and 176 cc of subdural fluid was evacuated. The patient remained neurologically well and returned to his assisted living residence two days later.

Figure 28A:
Figure 28B:
Figure 28C:
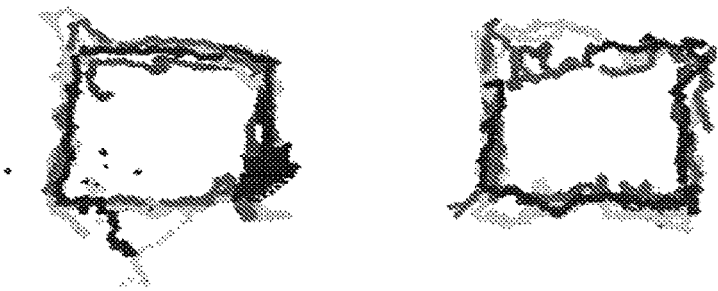

FIG. 28 (A, B, C) represents the eye movement tracking of a 67 year old male with a past medical history of prostate cancer, hypertension, hyperlipidemia, alcoholism in remission, and gunshot wound to the left shoulder with retained missile fragment. His ophthalmic baseline was 20/40 vision in the right eye and 20/50 in the left eye. He presented with 2 months of stuttering and right arm and hand weakness. He had a witnessed seizure on the day of presentation that began with shaking of the right upper extremity and progressed to generalized tonic-clonic activity. On examination he had intact pupils and extraocular movements. His speech was slow with paraphasic errors and difficulty with repetition and naming. A. Head CT with contrast revealed a left frontotemporal cystic mass. B. Eye movement tracking was performed for both the left and the right eye. The patient underwent awake stereotactic drainage of the cyst, which revealed necrotic cells and was non-diagnostic for malignancy, followed by awake stereotactic craniotomy with speech mapping for resection of a glioblastoma multiforme. Gross total resection was achieved radiographically. The patient had preserved speech but mild hemiparesis postoperatively and participated in rehabilitation prior to discharge home. He received temodar and radiation therapies as an outpatient and remained independent in activities of daily living with no tumor recurrence at four months postoperatively. C. Eye movement tracking was performed for both the left and the right eye one month after tumor resection.

FIG. 29 (A, B, C) represents the eye movement tracking of a 65 year old male with a past medical history of hypertension, hyperlipidemia, coronary artery disease and post-traumatic stress disorder, with no known ophthalmic disorders and visual acuity of 20/20 bilaterally presented 2 weeks after left parietal craniotomy for a esophageal junction metastasis by an outside surgeon with worsening right hand coordination and ataxia. On examination the patient had right pronator drift and hemineglect. A. CT revealed edema at the surgical site and MRI revealed a peripherally enhancing collection in the previous tumor cavity. B. Eye tracking was performed and then the patient was taken to the operating room for re-exploration craniotomy and evacuation of an abscess deep to the dura. He was treated with antibiotics for 12 weeks postoperatively. C. Eye tracking was again performed one week postoperative.

FIG. 30 (A, B, C, D, E) represents the eye movement tracking of vestibular schwannoma surgical control cases. Three patients (A, B, and E) underwent resection and one had gamma knife radiation (C) for vestibular schwannoma tumors while one patient elected only serial observation (D). Both left and right eye movement tracking is provided in the left and center column while MRI films are provided in the right column.

FIG. 31 represents the eye movement tracking of a 68 year old male with a past medical history of HIV infection, diabetes, hypertension, and stroke presented after 2 falls to his neurologist. A large volume lumbar puncture was performed. The opening pressure was 3 cm. The patient's gait was dramatically improved by the tap. A Codman shunt with Certas programmable valve set to 4 was placed and the patient continued to demonstrate progressive improvement clinically. Serial tracking was performed and paralleled the clinical improvement in gait.

Figure 32:
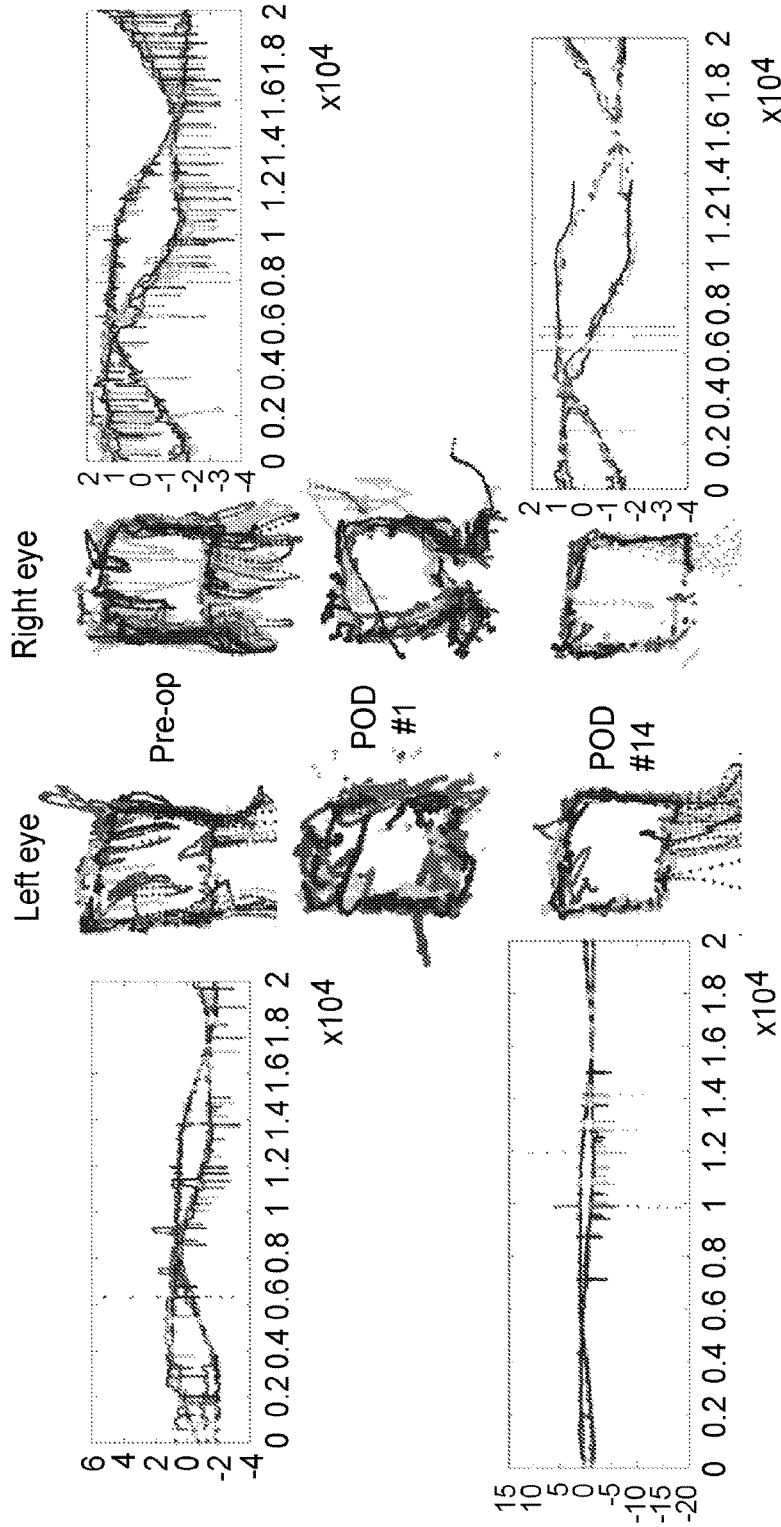

FIG. 32 represents the eye movement tracking of a 57 year old construction worker with presented with increasing gait disturbance and memory problems progressive over 5 years. He was fired from his job as a construction worker after falling at work. His mini mental status exam improved by 3 points, as did his gait after a large volume lumbar puncture. A Codman shunt with Certas programmable valve set to 5 was placed and the patient continued to demonstrate progressive improvement clinically. Serial tracking was performed and paralleled the clinical improvement in gait.

Figure 33:
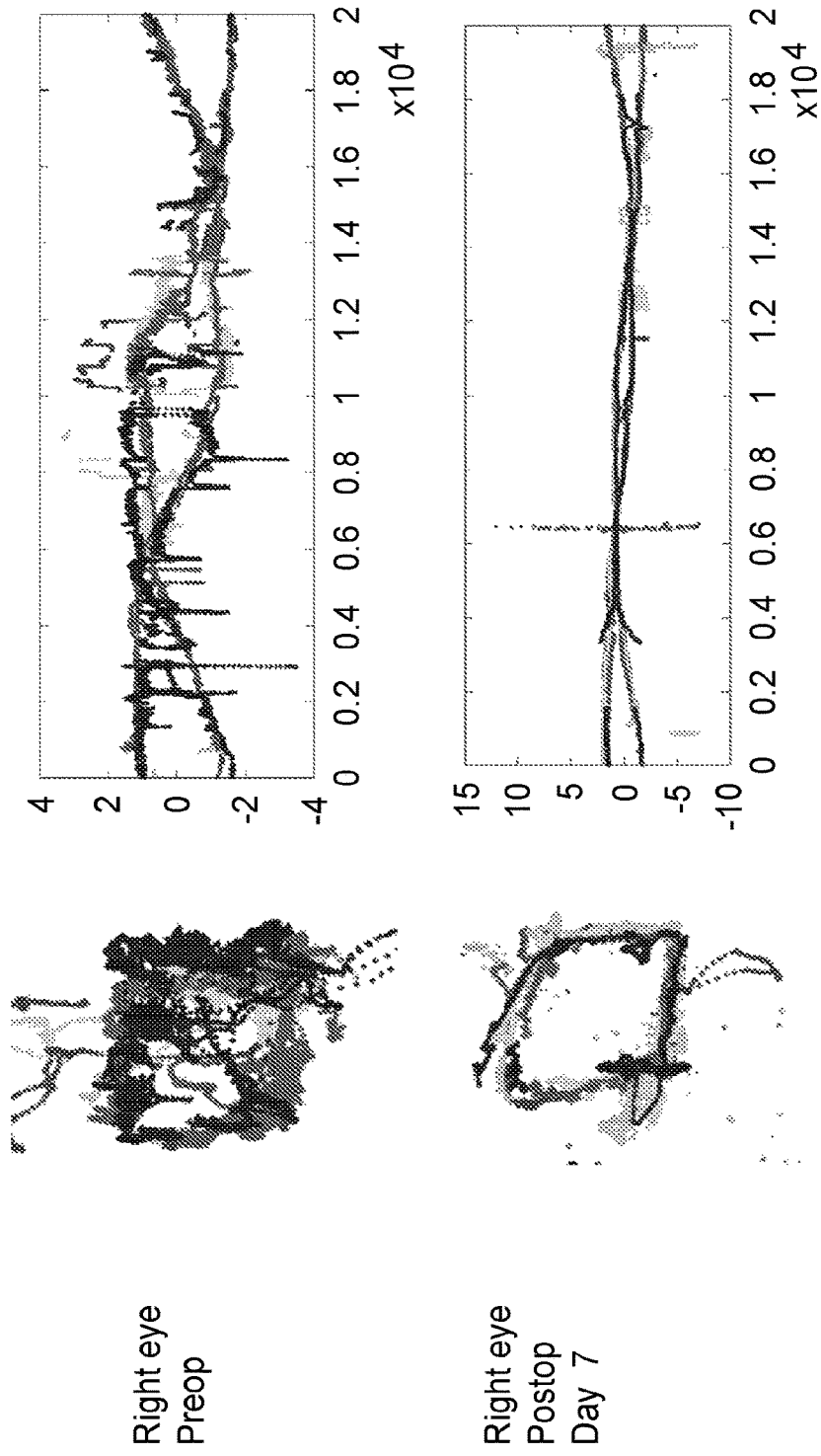

FIG. 33 represents the eye movement tracking of an 87 year old male World War II veteran with a past medical history of asthma, hypertension, posttraumatic stress disorder and benign prostatic hypertrophy had undergone shunting for normal pressure hydrocephalus at the age of 73 for a gait apraxia. A medium pressure PS medical valve was placed at that time. He underwent three subsequent distal shunt revisions without changing of the valve. He now presented again with progressive gait apraxia and shuntogram demonstrating distal malfunction. Since he had already failed three intraperitoneal shunts, the shunt was now revised and placed in the pleural space. Neither the valve, nor the shunt tubing was changed. The patient demonstrated improvement in his gait which paralleled the improvement in tracking.

FIG. 34 provides results of serial tracking of a 57 year old male with multiple sclerosis and bilateral optic neuropathy. The tracking demonstrates no serial improvement.

FIG. 35 represents the eye movement tracking of a person with a known VIth nerve palsy resulting in diplopia and detected by an ophthalmologist was compared to normal controls. Although the box trajectory appeared flattened (FIG. 35 left), calculation of the aspect ratio revealed that it was indeed taller and narrower than a control trajectory (FIG. 35 right).

FIG. 36 represents the eye movement tracking of a 54 year old male with poorly differentiated papillary carcinoma who presented with a tender mass on the back of his head and a progressive headache. Imaging revealed a calvarial based metastasis nearly obliterating the fourth ventricle. There was no transependymal flow on MRI to suggest hydrocephalus (FIG. 36 right). Eye tracking demonstrated a box narrower than it was wide (increased aspect ratio) consistent with CN VI palsy.

FIG. 37 represents the eye movement tracking of the patient of FIG. 36 after the mass was resected. Repeat imaging on postoperative day one showed that the boxes had returned to having a normal aspect ratio.

FIG. 38 represents the eye movement tracking of a 56 year old male who presented with a lung mass and headaches. There was no transependymal flow on MRI to suggest hydrocephalus (FIG. 38 right). Eye tracking of the right eye demonstrated a box narrower than it was wide (increased aspect ratio) consistent with CN VI palsy.

Figure 39:
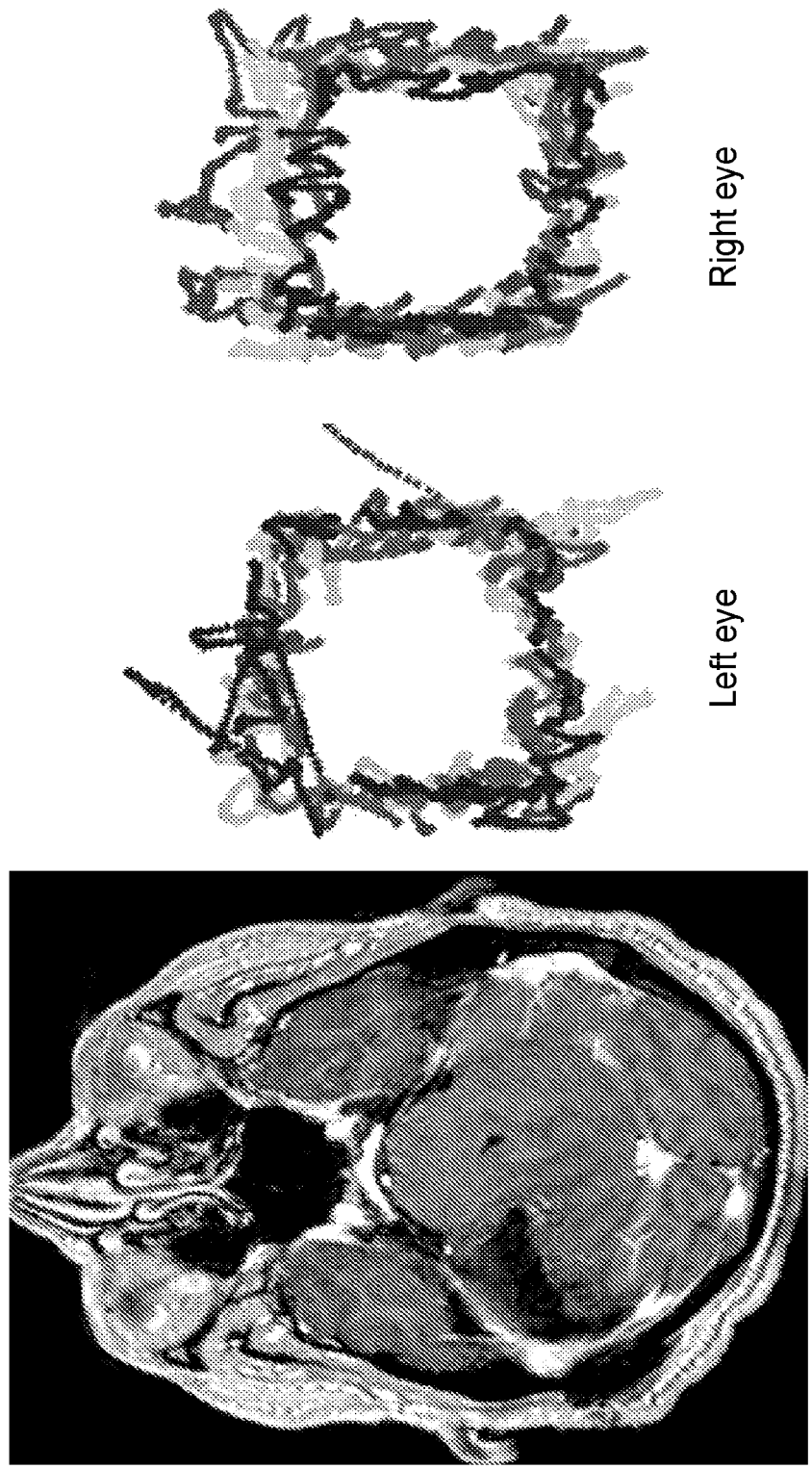

FIG. 39 represents that the patient of FIG. 38 postoperatively. The aspect ratio returned to normal.

Figure 40:
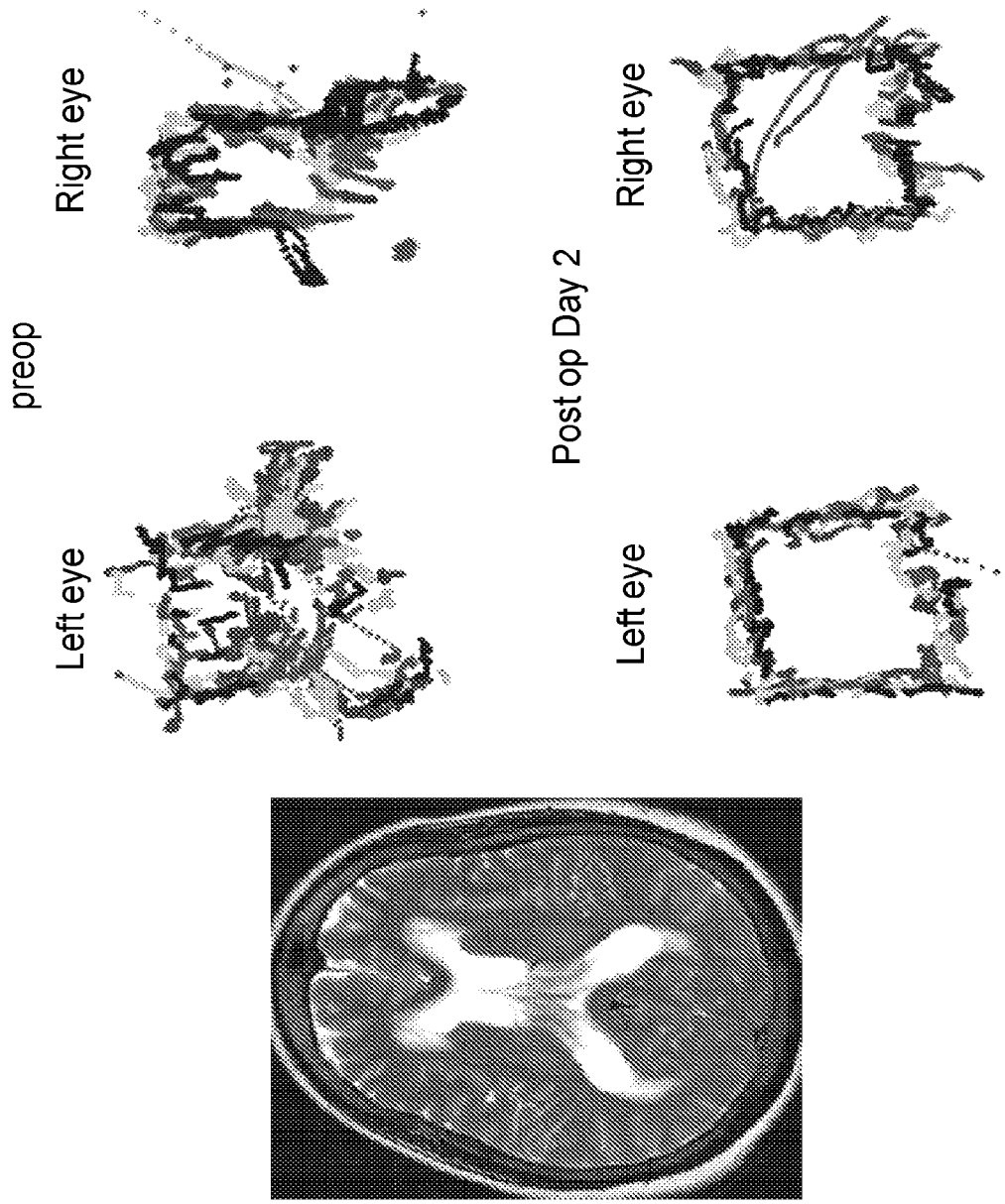

FIG. 40 represents the eye movement tracking of a 59 year old woman presenting with dizziness and headaches found to have hydrocephalus with no papilledema, but transependymal flow on MRI scan. She was shunted and her aspect ratio returned to normal postoperatively (FIG. 40 bottom).

Figure 41:
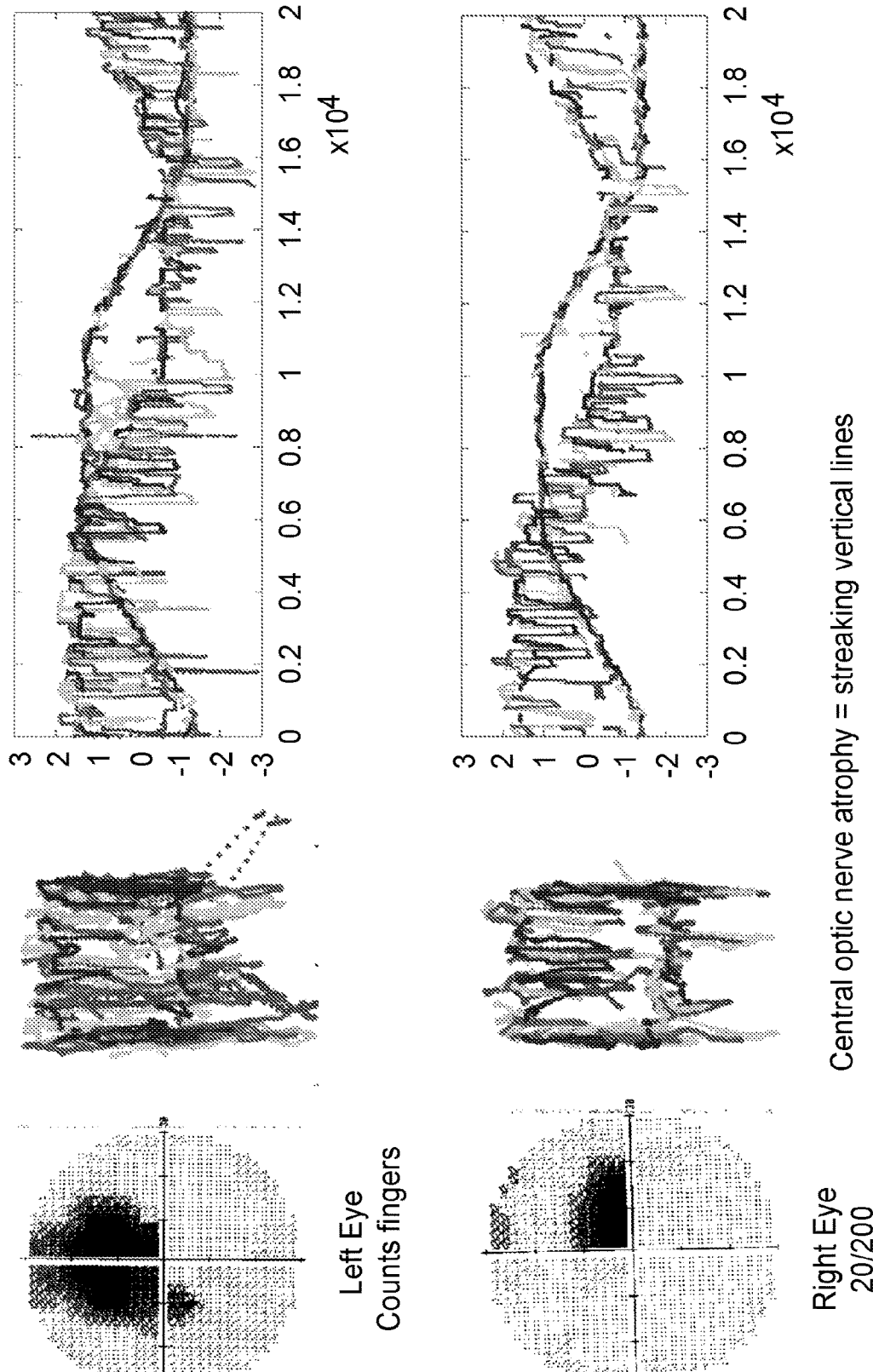

FIG. 41 represents the eye movement tracking of a patient with ocular histoplasmosis resulting in central optic nerve atrophy and showing extensive y-variability.

Figure 42:
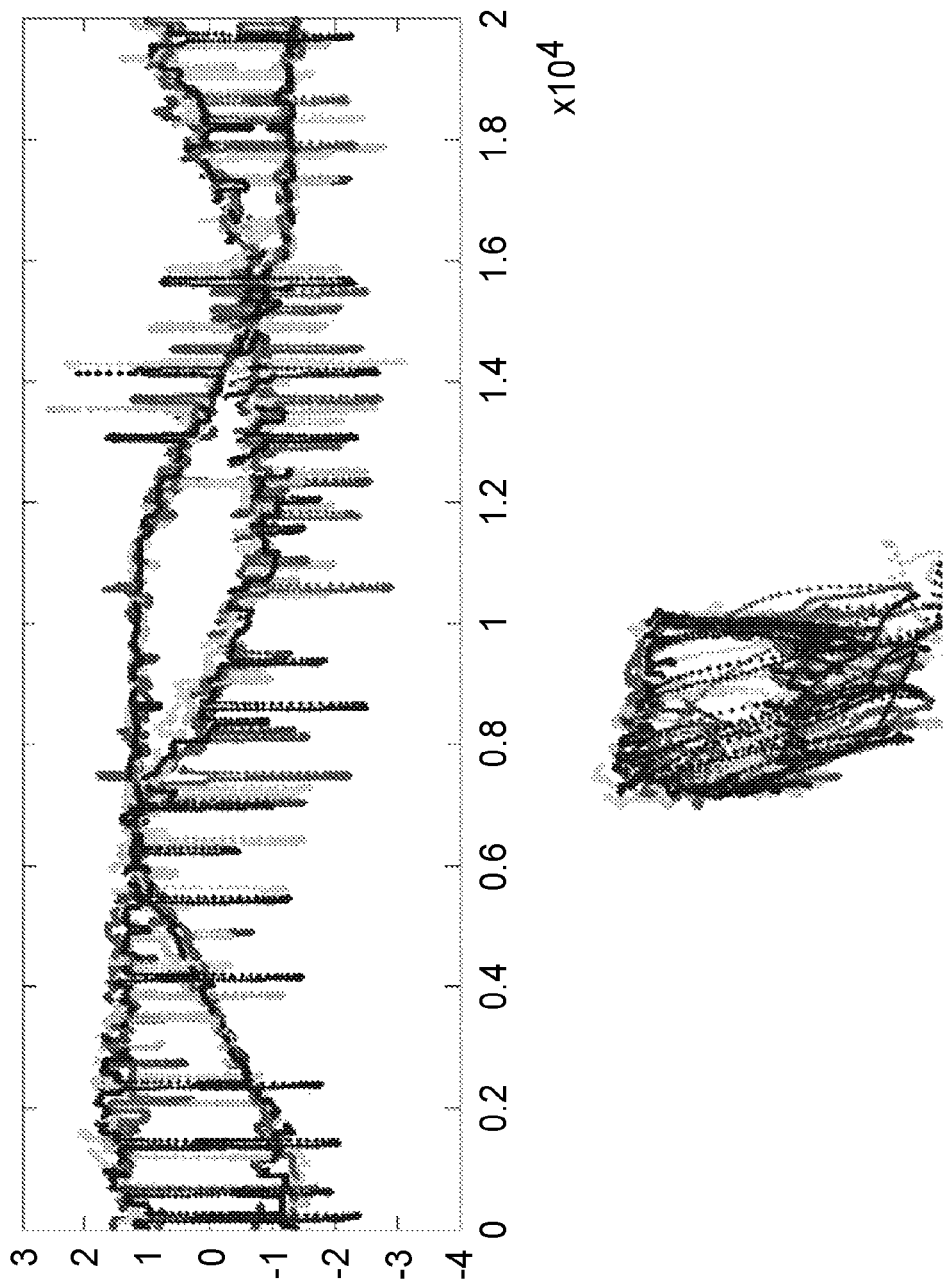

FIG. 42 represents the eye movement tracking of a 25 year old female patient being evaluated for optic neuritis also demonstrating increased y-variability.

Figure 43:
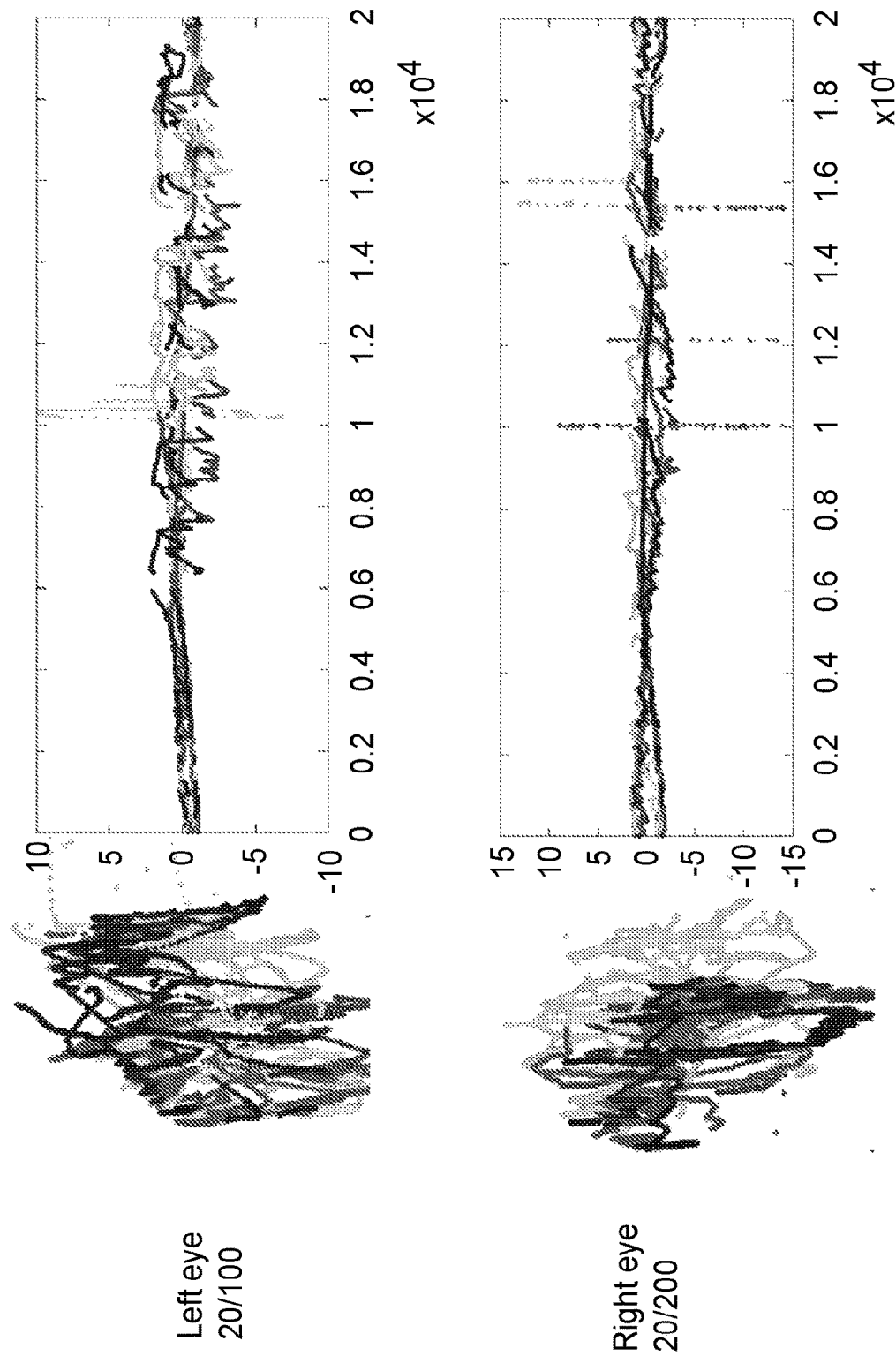

FIG. 43 represents the eye movement tracking of a patient with disconjugate gaze due to multiple sclerosis who demonstrated multiple cranial neuropathies. This pattern was not seen in the healthy control subjects nor in other patients including several with tumors impinging on the optic nerve, chiasm or tract or with poor visual acuity due to known ocular non-neuronal pathology.

Figure 44:
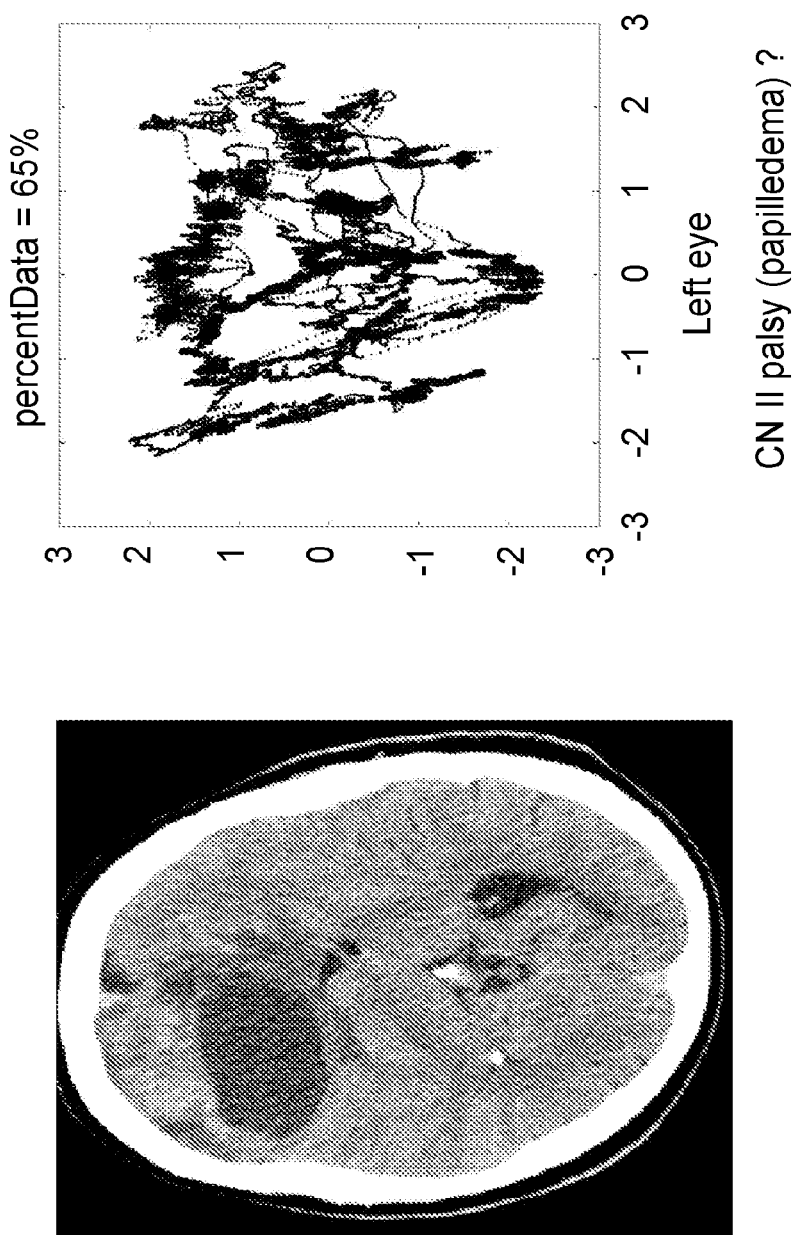

FIG. 44 represents the eye movement tracking of the left eye of a patient with a large right frontal brain tumor presenting with an examination consistent with papilledema demonstrated an increased vertical range box trajectory with no roof or floor similar to those seen in the central optic nerve atrophy and ocular histoplasmosis patients.

Figure 45:
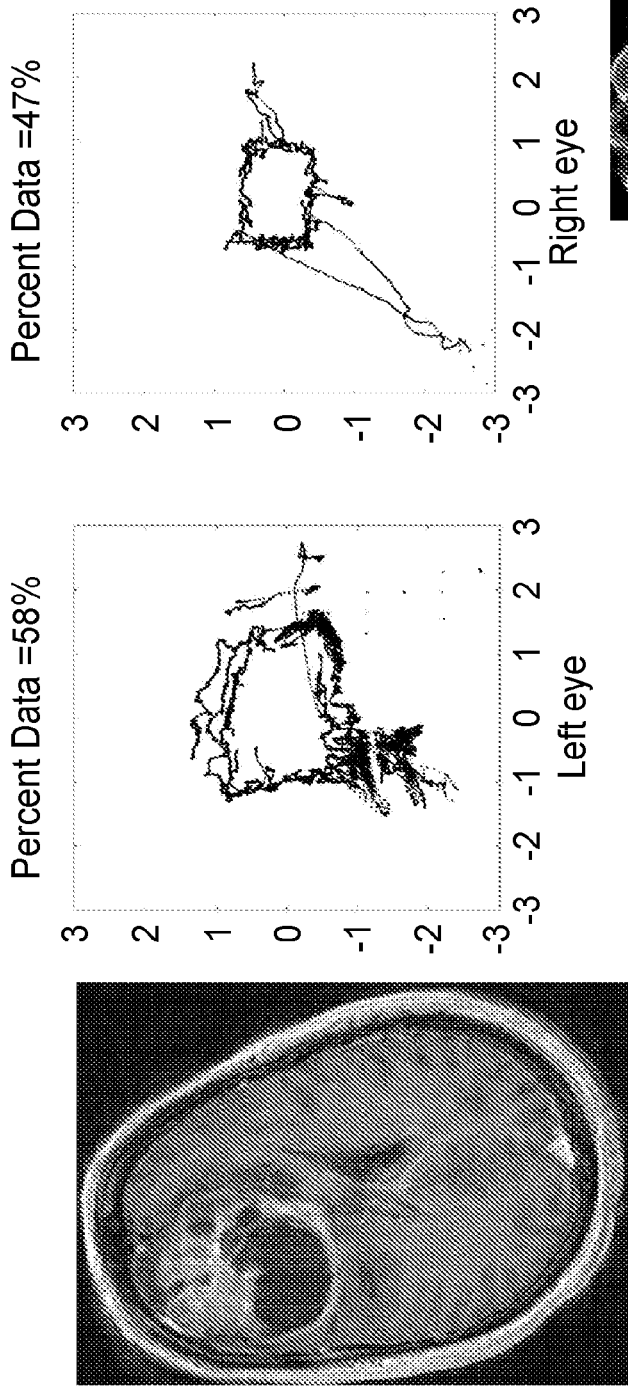

FIG. 45 demonstrates that this statistically significant deviation in y-variability resolved with steroids over 24 hours. The height of the patient's box trajectory remained decreased after the steroids and before resection, suggesting a component of IIIrd nerve palsy.

FIG. 46 demonstrates that the eye tracking trajectory of the patient represented in FIGS. 44 and 45 returned to normal by one week after resection.

DETAILED DESCRIPTION OF THE INVENTION

Before the present methods are described, it is to be understood that this invention is not limited to particular methods and experimental conditions described, as such methods and conditions may vary. It is also to be understood that the terminology used herein is for purposes of describing particular embodiments only, and is not intended to be limiting, since the scope of the present invention will be limited only by the appended claims. As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

Definitions

The terms used herein have the meanings recognized and known to those of skill in the art, however, for convenience and completeness, particular terms and their meanings are set forth below.

"Subject" or "patient" refers to a mammal, preferably a human, in need of or undergoing treatment or screening for a condition, disorder or disease such as, for instance, increased intracranial pressure.

By "assessing central nervous system integrity" is meant identifying one or more symptoms that may indicate a pathology of or affecting the central nervous system, or identifying, assessing, quantifying or diagnosing a pathology of the central nervous system. The pathology may be, for instance, one or more of increased intracranial pressure, hydrocephalus, concussion, dementia, schizophrenia, amyotrophic lateral sclerosis, muscular sclerosis, autism and Fragile X disease.

The methods described herein are distinct from conventional methods. As applied to determining intracranial pressure, a conventional ICP monitor determines the brain's pressure number in one spot, an $O_2$ monitor determines an oxygenation number in one spot, imaging reveals what the brain looks like, but the methods described herein provide methods for testing for physiologic function of the cranial nerves that may reflect factors that may delay axoplasmic transport such as elevated intracranial pressure.

The methods described herein may be used to detect elevated intracranial pressure and assess or determine the severity of the same. Similarly, the methods described herein may be used to localize the intracranial cause of such intracranial pressure and to monitor progression of lesions or diffuse processes within the cranium.

The methods described herein provide high sensitivity. No patient yet evaluated with an abnormal physical exam or films consistent with elevated ICP has had normal eye movement tracking. The methods described herein may be used to reduce the need for CT scans among potential shunt malfunction patients, patients with lesions causing elevated intracranial pressure, and may be used to screen patient populations such as emergency room ER populations, sports participants, soldiers or other combatants, nursing home residents or other populations at risk for falling for elevated intracranial pressure.

High resolution automated eye movement tracking, occurring over, for instance, about 220 seconds, is a powerful tool for detecting subclinically apparent ocular motility dysfunction, and thus aid in the rapid diagnosis of elevated intracranial pressure.

While palsies of cranial nerves II, III, IV and VI have all been described in patients with acute hydrocephalus (Tzekov et al., *Pediatric Neurosurgery* 1991; 17(6):317-320 and Chou et al., *Neurosurgery Clinics of North America* 1999; 10(4):587-608), the relative vulnerability of each nerve has not been well established. If length of exposure to the subarachnoid space were the sole predictor of vulnerability to intracranial pressure elevation, the IVth nerve would be most vulnerable (median length 33 mm (Hanson et al., *Neurology* 2004; 62(1):33-36)), the IIIrd nerve would be second most vulnerable (26 mm (Adler et al., *Journal of Neurosurgery* 2002; 96(6):1103-1112)) and IInd and VIth would be approximately equally least vulnerable (5 to 16 mm for II (Murali, R. Injuries of the Cranial Nerves. In: Golfinos P CaJ, ed. *Head Injury*. 4th ed. New York: McGraw Hill; 2000), and 11 mm median length for VI (Hanson et al., *Neurology* 2004; 62(1):33-36)).

The abducens nerve (VI) exits the brainstem from its tethering at the medullopontine junction and courses intracranially before entering Dorello's canal, where it is again tethered by fibrous and osseous structures. Elevation of supratentorial ICP forces the parahippocampal gyri down past the free edge of the tentorium while the brainstem with the tethered VIth nerve moves caudally toward the foramen magnum, stretching the nerve where it enters Dorello's canal (Hanson et al., *Neurology* 2004; 62(1):33-36). Posterior fossa lesions pushing the cerebellum and brainstem forward may directly compress the VIth nerve against the clivus (Hanson et al., *Neurology* 2004; 62(1):33-36). It is also possible that the increased reporting of VIth nerve palsies may be due to their easier detection on clinical examination than III and IVth nerve palsies.

The data presented herein does not feature a calibration step in eye movement tracking. Thus patients need not reliably follow instructions, and the data does not filter out the possible effects of cranial neuropathy. Unlike other studies (Contreras et al., *Brain research* 2011; 1398:55-63; Maruta et al., *The Journal of Head Trauma Rehabilitation* 2010; 25(4):293-305; Contreras et al., *Journal of Biological Physics* 2008; 34(3-4):381-392 and Trojano et al., *J Neurol* 2012; (published online; ahead of print)) the data presented herein does not use saccade count or spatial accuracy as the measure. In addition to results based on the moving aperture's periodic envelope presented in this paper, the methodology also affords a very fine-scale data showing eye movements in response to the successive frames of the movie itself.

The methods described herein build on pre-existing methods that rely on intact ocular motility to address clinical questions. (Lee et al., *Brain research*. 2011; 1399:59-65; Contreras et al., *Brain research* 2011; 1398:55-63; Maruta et al., *The Journal of Head Trauma Rehabilitation* 2010; 25(4):293-305). The methods described herein differ in several ways. First, the present methods feature diagnosing specific clinical conditions related to vision and ocular motility reflecting the function of cranial nerves II, III, IV, VI and associated nuclei rather than measuring cognitive impairment due to primarily cortical mild to moderate traumatic brain injury. Second, the present methods use more fine-scale information, using, for instance, about 100,000 measurements to pull out subtle differences that can be lost through the somewhat arbitrary thresholding of velocity measures into saccades. Third, the present methods do not use measurements of spatial accuracy, which requires transforming the raw data by a series of scaling and rotating processes whose effectiveness depends on the ability of their subjects to follow precise commands reliably. In such methods previously used, it is necessary to exclude the vast majority of neurologically compromised patients. Further, such methods previously used lose any information related to the function of cranial nerves II, III, IV and VI, because the spatial distortions expected to result from damage to these nerves is reversed in the process of spatial calibration.

Trojano et al., *J Neurol* 2012; (published online; ahead of print) recently described uncalibrated eye movement measurements in a population of minimally conscious and persistently vegetative patients. The methods described herein differ in several ways. First, Trojano et al. report data from 11 rather than 25 healthy control subjects. Second, Trojano et al. evaluate chronic disorders of consciousness rather than acute changes in intracranial pressure. Third, Trojano et al. sample eye movements at 60 Hz rather than 500 Hz, effectively reducing the power of the data 100-fold. Fourth, Trojano et al. report differences in on-target and off-target fixations between the groups, despite not having spatially calibrated the data, making these values noisy. Finally, Trojano et al. use static stimuli moving in a quasiperiodic way. The methods described herein use moving images shown within an aperture that moves periodically and allows assessing both coarse and fine eye movement characteristics in both controls and patients.

Clinical Implications.

The data presented herein are consistent with compartmentalization of subarachnoid spaces, as several of the patients demonstrate elevated ICP on one side of the brain, but not the other. The methods for ICP assessment described herein represent a significant advantage over conventional radiographic studies because while the latter depict how the brain appears, our technique captures how well it functions. CT scanning may require brief sedation in a pediatric population and risks radiation exposure, while MR may require prolonged sedation. Brain imaging may not be diagnostic of elevated ICP in patients with chronically enlarged ventricles without classic findings such as transependymal flow on T2 weighted MR imaging (Mizrachi et al., *J Neuroophthalmol.* 2006; 26(4):260-263). Patients with non-compliant and slit ventricles may also have elevated ICP in the absence of radiographic abnormality (Engel et al., *Neurosurgery* 1979; 5(5):549-552). Shunt tapping risks infection and malfunction, particularly in patients with slit ventricles. Invasive monitoring risks intracranial hemorrhage. Thus additional low-risk, rapid techniques for assessment of hydrocephalus or elevated ICP may be useful to those assessing populations at risk for these pathologies.

The methods described herein provide a useful adjunct for diagnosis of elevated ICP and the prospective monitoring of such patients at risk for its development. No patients with elevated ICP by history, physical examination and radiology have demonstrated normal ocular motility, demonstrating that the methods described herein are sensitive. The data presented herein demonstrate that patients with grossly intact extraocular movements on physical exam, and relatively minimal changes in pathology, may have profound disruption on high resolution tracking.

Given the diverse baseline ocular pathology of hydrocephalic patients alone (Dennis et al., *Arch Neurol.* October 1981; 38(10):607-615; Zeiner et al., *Childs Nerv Syst.* 1985; 1(2):115-122 and Altintas et al., *Graefe's archive for clinical and experimental ophthalmology=Albrecht von Graefes Archiv fur klinische und experimentelle Ophthalmologie.* 2005; 243(12):1213-1217), tracking results may need to be compared to each patient's own normative data.

The data presented herein demonstrates in part that it is possible to diagnose elevated intracranial pressure by analysis of eye movements during watching of a video. The methods described herein are significantly different from other technologies since imaging studies enable one to see the brain and invasive techniques enable determination of an arbitrary pressure or oxygenation number. The methods described herein actually assess physiologic functioning.

The methods described herein have many clinical applications including, for instance, i) assessing function of cranial nerves II, III, IV and VI, and perhaps even VII, VIII, and/or X; ii) detecting and quantitatively monitoring any process impeding or improving the function of the above (e.g. demonstrating elevated ICP or increased brain mass effect, that may be applied to such things as aneurysms, multiple sclerosis, sarcoidosis, tumors, aging, alcohol abuse, intoxicants/narcotics, etc.), iii) localizing pathology and identifying the nature of that pathology within the brain (e.g. differentiating between lesions that compress nerves and those that only create mass effect or elevate ICP far away); iv) monitoring patients via home computer/webcam, in-hospital or outpatient "TV shows" that perform "neurochecks" on a regular basis; v) quantitatively measuring outcome for assessment of persistently vegetative and minimally conscious state, aphasia, and recovery from brain injury; vi) characterizing types of aphasia and localizing pathology; vii) quantitatively assessing dementia/cognitive function. Likewise, the methods described herein may provide means for in-person screening such as to, for example, assess vision, assess ocular motility, and assess cognitive dysfunction all relatively simultaneously (e.g. for a driver's or pilot's license, employment etc.). Further, the methods described herein may be used to assess variance, which appears to increase with cognitive decay. This could be used, for instance, to target advertising by stratification of intelligence. Still further, the methods described herein may be used for intelligence or neurologic function testing.

Figure 17:
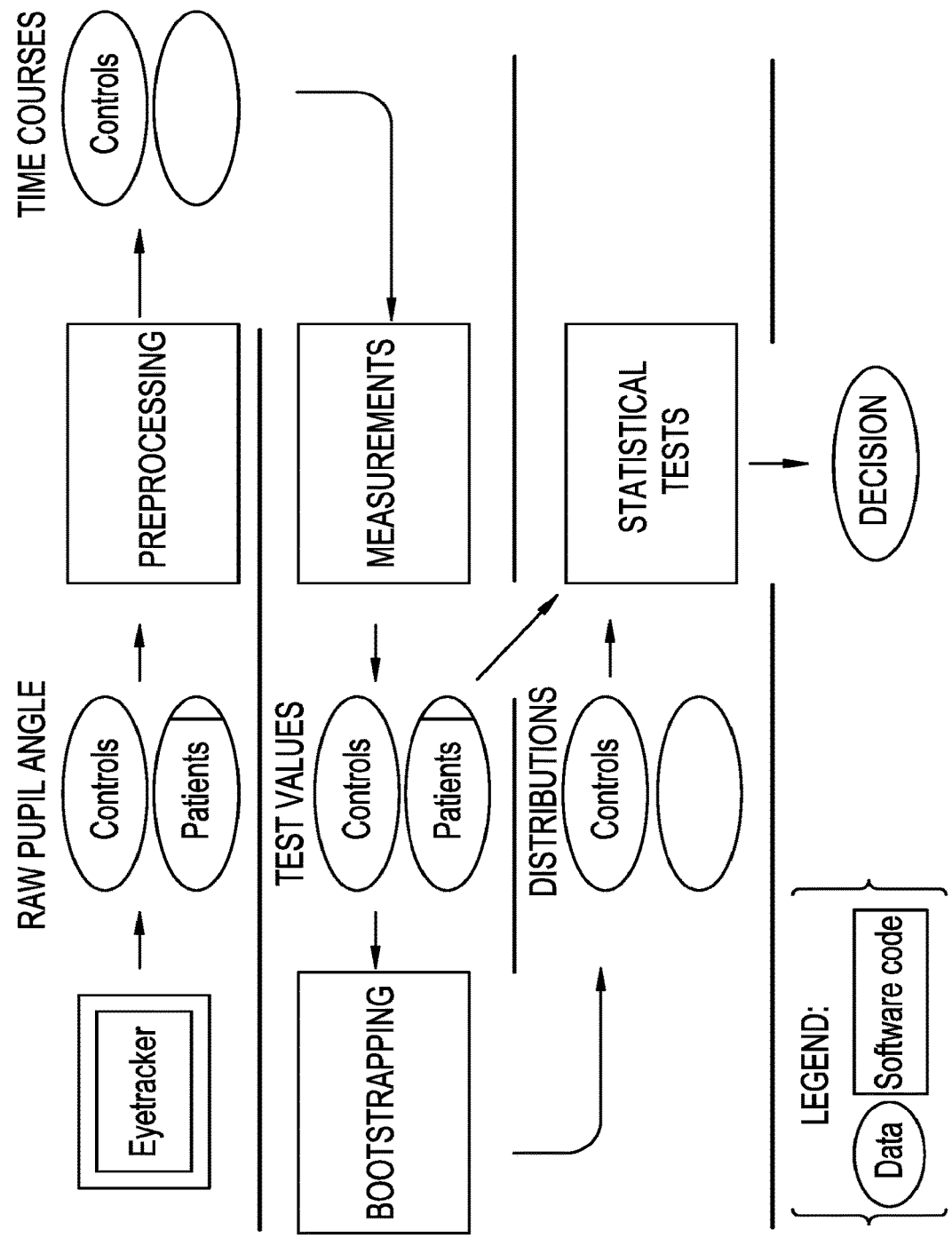
FIG. 17 is a flowchart demonstrating how the eye movement tracking of both subjects or patients and controls may be tested and compared. An eyetracker device is provided to measure raw pupil angle in response to a visual stimulus over a determined time period. Measurements are made and distributions of values measured may be generated. Statistical tests may be performed on the distributions to determine a diagnosis or screen for reduced nerve conductance and function and increased intracranial pressure. Processing the eye movement observations, making measurements, determining distributions of values measured and performing statistical tests may all be accomplished using suitable computer software.
Figure 18:
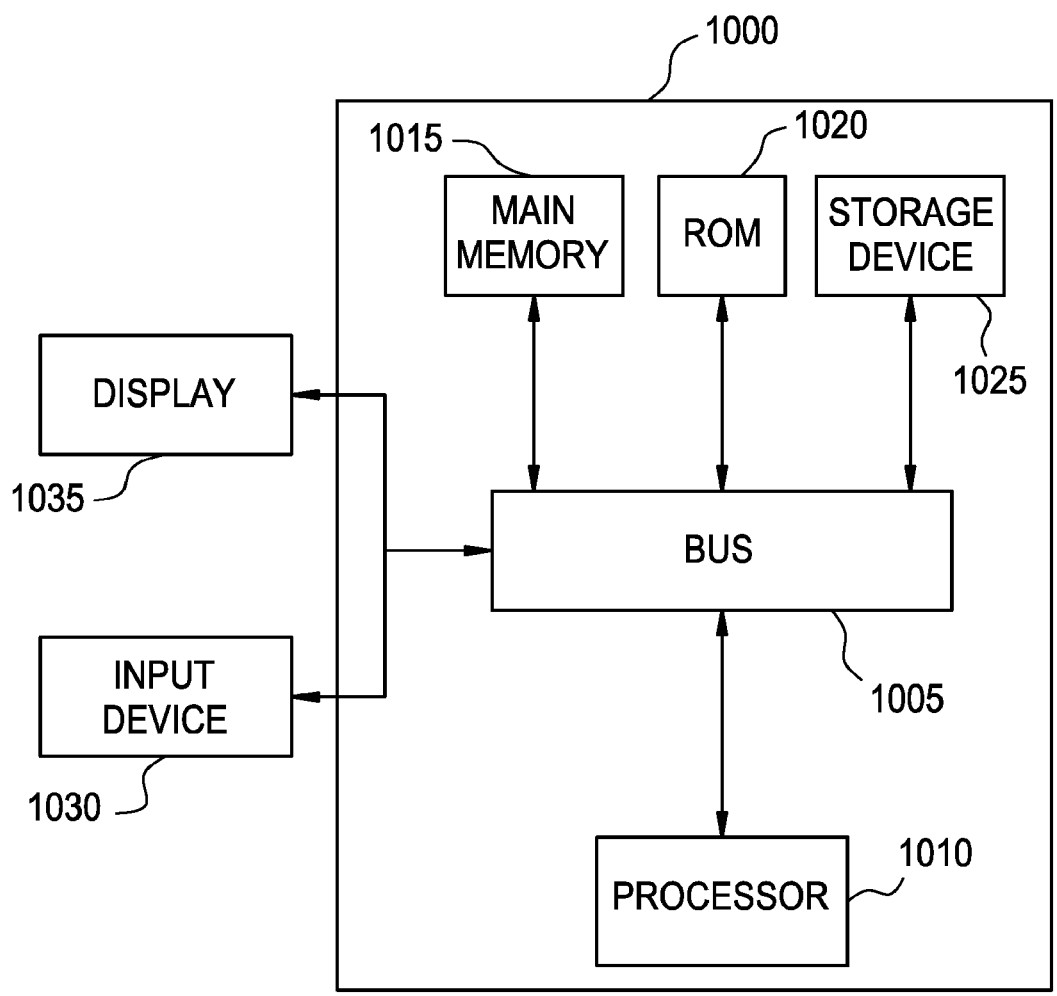
FIG. 18 is a block diagram of a computer system in accordance with an illustrative implementation.
Figure 19:
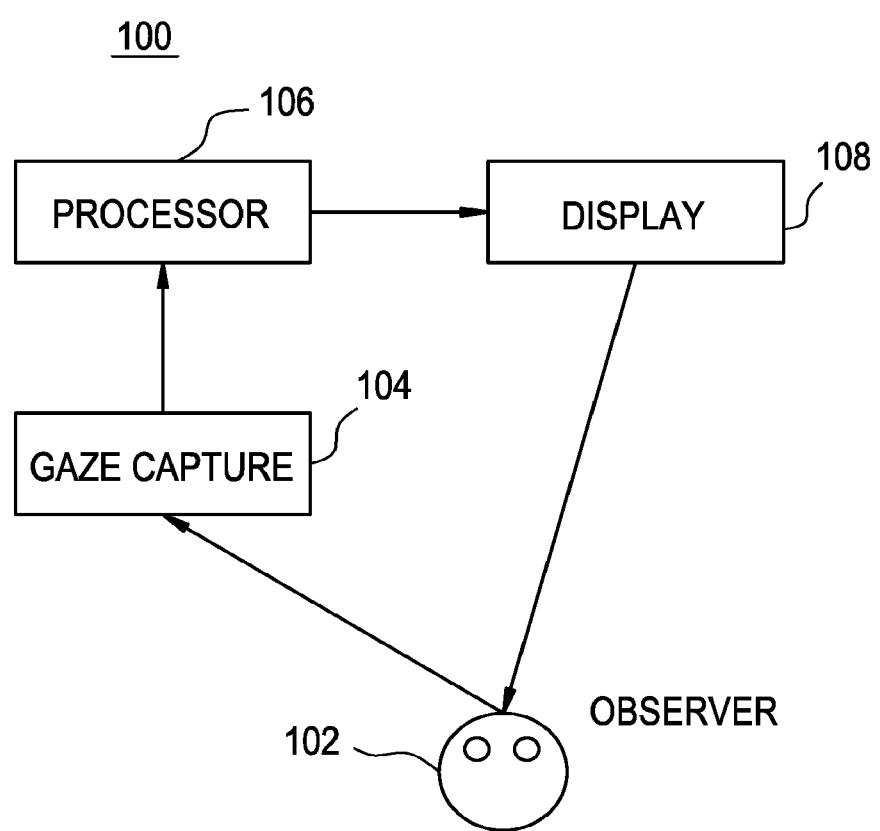
FIG. 19 is a schematic diagram showing a configuration of how a subject's eye movements are measured, analyzed and displayed by such a computer system as shown in FIG. 18.

A computing system according to the invention is described in FIGS. 17-19. Implementations of the observer matter and the functional operations described herein can be implemented in other types of digital electronic circuitry, or in computer software, firmware, or hardware, including the structures disclosed in this specification and their structural equivalents, or in combinations of one or more of them. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

Implementations of the observer matter and the operations described herein can be implemented in digital electronic circuitry, or in computer software, firmware, or hardware, including the structures disclosed in this specification and their structural equivalents, or in combinations of one or more of them. The observer matter described herein can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described herein can be performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the observer matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Described herein are many specific implementation details, these should not be construed as limitations on the scope of any inventions or of what may be claimed, but rather as descriptions of features specific to particular implementations of particular inventions. Certain features described herein in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

The relationship of aspect ratio and variance as measures of the signal. When the (x,y) pairs are plotted to show the 'box plots,' they have been preprocessed because the absolute values of the raw data are of limited use since changes in the signal over time are most important. There are many ways to normalize data, including dividing by the mean, by the standard deviation, or by the variance. Furthermore, the standard deviation or variance can be computed for all the data at once or x can be normalized using the variance of x and y can be normalized using the variance of y. Any normalization procedure for periodic data likely includes subtracting the mean, so the signal can be plotted as signal change alternating around zero. All of these transformations are conventional and widely used in data analysis by those of ordinary skill in the art. The details depend on the question being asked and the type of modeling or statistical testing being used.

In creating the box plots described herein, the raw data is preprocessed as follows: for the x (horizontal) and y (vertical) vectors independently, the mean is subtracted and divided by the standard deviation (which is the square root of the variance). This puts all the data in the same relative frame (zero-mean, max and min about 1 and −1). This is the reason the boxes look square (even if the stimulus presentation monitor is not square).

This means that 'long' and 'short' sides are reflecting relative variability. If the variability is high, the denominator is high and the measure value low. So, for example, if the variability of the horizontal (x) data is high relative to the variability of the vertical (y) data, the horizontal aspect of the box will be relatively smaller, and the result will be a tall skinny box (higher aspect ratio). Conversely, if the variability of the vertical (y) data is high relative to the variability of the horizontal (x) data, the vertical range will be reduced and the result will be a short fat box (lower aspect ratio).

Thus, particular implementations of the observer matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous

EXAMPLES

The following examples are set forth to provide those of ordinary skill in the art with a description of how to make and use the methods and compositions of the invention, and are not intended to limit the scope thereof. Efforts have been made to insure accuracy of numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Background

Eye movements contain clinically important information about neurological integrity. Clinical devices may take advantage of the relative ease of automated eye-movement tracking, for applications such as assessing recovery following clinical intervention. We designed a technique that can reliably measure eye movements with precision, without initial spatial calibration. We tracked eye movements without spatial calibration in neurologically intact adults and in neurosurgical patients as they watched a short music video move around the perimeter of a screen for 220 s. We measured temporal features of the data, rather than traditional spatial measures such as accuracy or speed.

We reliably discriminated between the presence and absence of neurological impairment using these uncalibrated measurements. Our results indicate that this technique may be extended to assess neurologic integrity and quantify deficits, simply by having patients watch TV.

These methods are useful in a number of contexts, including rapid assessment of potentially neurologically injured individuals, monitoring of patients whose states might fluctuate between impairment and recovery, and measuring the efficacy of rehabilitation or intervention.

Eye movements have long been known to contain clinically relevant information about neurological integrity. Assessment of ocular motility is a standard part of any neurological exam, because it is easy and informative. However, there are some problems with the standard clinical exam including that it is normally administered by an expert, and generally is only qualitative, not quantitative.

The relative ease, portability, and noninvasiveness of automated eye-movement tracking devices has made it a promising area of translational research, for applications such as testing for concussion on athletic fields and assessing recovery following clinical intervention. Eye movement studies have provided insight into clinical fields from psychiatry to traumatic brain injury (TBI) and rehabilitation. (Trojano, et al., *J Neurol.*, 2012, 259(9):1888-95; Gitchel, et al., *Arch Neurol.*, 2012, 69(8):1011-7; Qiu, et al, *PLoS One*, 2011. 6(10):e25805; Plow, et al., *PMR*, 3(9):825-35; Heitger, et al. *Brain.*, 2009. 132 (Pt 10):2850-70; Pearson, et al., *Br J Sports Med.*, 2007, 41(9):610-2; Heitger, et al., *J Neurol Sci.*, 2007. 15:253(1-39 2):34-47; Suh, et al., *Neurosci Lett.*, 2006, 401(1-2):108-13; Suh, et al., *Neurosci Lett.*, 2006, 410(3):203-7; Heitger, et al., *Brain Inj.*, 2006, 20(8):807-24; Yang, et al., *Image and Vision Computing*, 2002, 20(4):273-87; and Heitger, et al., *Prog Brain Res.*, 2002, 40:433-12 48) Studies commonly measure accuracy of spatial fixation, time spent on particular fixation targets, and saccade count. (Trojano, et al., *J Neurol.*, 2012, 259(9):1888-95 and Foulsham, et al., *Vision Res.*, 2011, 51(17):1920-31) Despite the promise, it has proven difficult to develop clinical applications based on quantitative measurements of eye-movements, (Heitger, et al., *Prog Brain Res.*, 2002, 40:433-12 48 and Foulsham. et al., *Vision Res.*, 2011, 51(17):1920-31) possibly because spatial calibration can be difficult in clinical settings, and because spatial calibration precludes the use of eye tracking for detection of dysfunctional ocular motility.

The standard use of an eye-tracker requires that the system be calibrated individually for every observer at the start of every measurement session. Calibration involves asking the observer to look at a series of high-contrast dots displayed on a computer monitor. The calibration process may be repeated several times until sufficient accuracy has been achieved. Only then can eye movements be recorded.

It has been difficult to use eye-tracking in clinical applications with observers for whom this calibration process is difficult (e.g., requiring many repetitions) or impossible. Calibration requires a willing observer who can follow commands reliably. Many clinical conditions that result in a loss of neural integrity, such as stroke or brain injury, also render the observer unwilling or unable to follow instruction.

Also problematic for using eye-tracking methods to brain injury or stroke patients, the calibration process itself may reduce the sensitivity of the eye tracking test. For example, consider a patient with impaired vertical ocular motility. Because the calibration process assumes that the eyes cover the full range of locations mapped out by the calibration points, it assigns the maximum pupil angle up and down incorrectly to the 'top' and 'bottom' of the monitor, respectively. In such instances, all future measurements for that observer are adjusted to conform to that incorrect assignment. Thus, impaired ocular motility may be undetected in tests that begin with a spatial calibration of the eye tracker.

Eye movement measurements may reflect severity of damage to the brain, as well as recovery following clinical intervention. The methods described herein were used to test 35 patients from a neurosurgery clinic as well as a control set of healthy volunteers. The success of the method involves two features. First, the methods described herein do not use spatial measures of accuracy as a variable of interest. By looking at eye movement trajectories in the time domain rather than the spatial domain, it is possible to quantify measures that do not rely on spatial calibration. Second, the measures are easily visualized and evaluated, making them immediately useful to the clinician or researcher.

Methods

Subjects. Twenty-four healthy observers were recruited in New York University according to IRB approved protocols as determined by the University Committee on Activities Involving Human Subjects (UCAIHS). All participants provided written informed consent, and the consent forms were approved by UCAIHS. Thirty-five test patients with neurological deficit were recruited from the neurosurgical practice at the New York Harbor Healthcare System (NYHHS). Written informed consent from the subjects or their legal proxies were obtained for prospective data collection according to guidelines established by the VA New York Harbor Healthcare System Research and Development Subcommittee for Human Studies, and the consent forms were approved by this IRB. This study was approved by this IRB.

Observers. Because of the potential for uncalibrated eye-tracking to serve as an initial screen, the patient population was not restricted to a specific pathology. Rather, an arbitrary sample of patients who came through the clinic was recruited. The resulting sample was representative of the range of disorders seen in the clinic. Twenty two percent had disorders of the spine, and the rest of the group had central nervous system tumors, hemorrhages, vascular lesions and/or trauma. This heterogeneous group is referred to collectively as the "test patients."

Eye Movement Tracking. Observers' eye movements were recorded using an Eyelink 1000 monocular eye tracker (500 Hz sampling, SR Research). All observers were seated approximately 55 cm from the screen. Some test patients were tracked on multiple visits at different stages of diagnosis, surgery, and recovery. This resulted in a total of 77 eye-movement timecourses for the test patient population. There were 45 eye movement timecourses for the neurologically intact control population.

Visual Stimulus. The visual stimulus provided as a music video that played continuously while it moved clockwise along the outer edges of a computer monitor. Observers were instructed to watch the video. The stimulus was expected to evoke smooth pursuit eye movements as well as possible saccades and microsaccades as the observers scanned the video. The video was presented in a square aperture with an area approximately ⅛ of the size of the screen (about 16○ of visual angle). This square aperture started at the upper left hand corner of the screen and moved at a constant speed, taking 10 seconds to traverse each edge of the monitor. A full cycle took 40 seconds, and five full cycles were played, for a total of 200 seconds. A countdown video played in the starting position for 10 seconds before the music video began, to give observers time to orient to the stimulus. Only the 200 seconds of the music video were used for analyses. The eye tracker sampled eye position at 500 Hz. yielding 100,000 samples of eye position over 200 seconds.

Axis Orientation. The camera and monitor were securely mounted, so that 'horizontal' for the camera was the same as 'horizontal' for the monitor. Therefore, the terms 'horizontal' and 'vertical' are defined with respect to the monitor, not with respect to head-tilt. However, the head was typically aligned with the monitor, and a chinrest was used with all controls and about half of the patients, to ensure the continued alignment. The eyetracker converted changes of pupil angle into two orthogonal components which it labeled x, and y, and which in turn referred to horizontal and vertical change, due to the linked orientation of the monitor and camera. Therefore, we also refer to horizontal and vertical components as x and y respectively.

Data preprocessing. There was no spatial calibration so the units of the raw timecourses were of limited value. Therefore, for each observer, the timecourses were normalized by subtracting the mean and dividing by the standard deviation. This was done for each timecourse independently. The different timecourses were treated as distinct data sets from the same test patient or neurologically intact control.

Figure 1A:
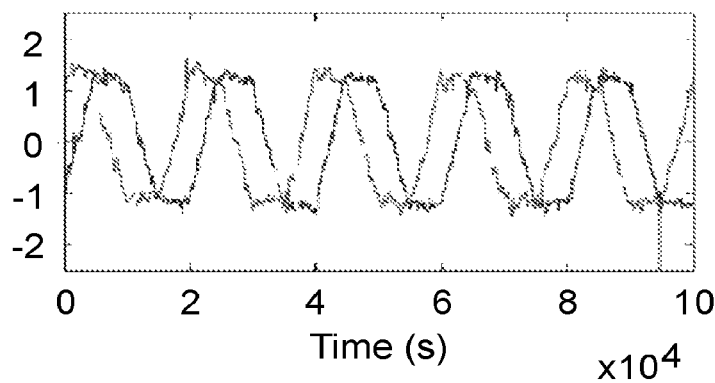
FIGS. 1A, B, and C provide timecourses of eye movements for the full run over time. Blue, horizontal (x) position. Green, vertical (y) position.

Timecourses. he normalized x- and y-timecourses were plotted across time (FIG. 1a). The clockwise movement of the visual stimulus alternated between horizontal changes and vertical changes, and the x- and y-timecourses in neurologically intact observers show the same alternation.

Figure 1D:
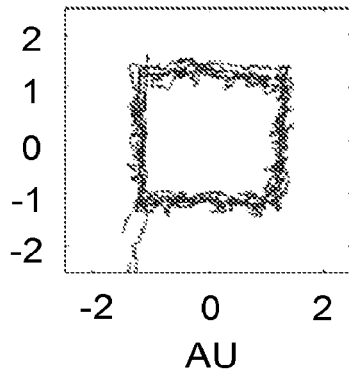
FIGS. 1D, E. and F provide scatterplots of eye position (x vs. y, in units of normalized relative distance from center).
Figure 1B:
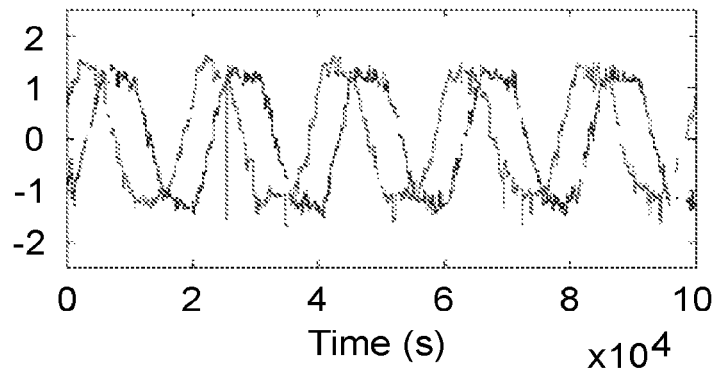
FIGS. 1B, C, E, and F are the results obtained from test patients.
Figure 1E:
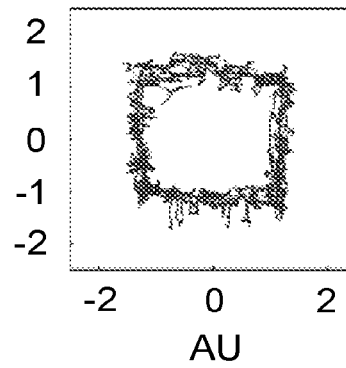
FIG. 1 (A, B, C, D, E, F) demonstrates characterizing eye movements.
Figure 1C:
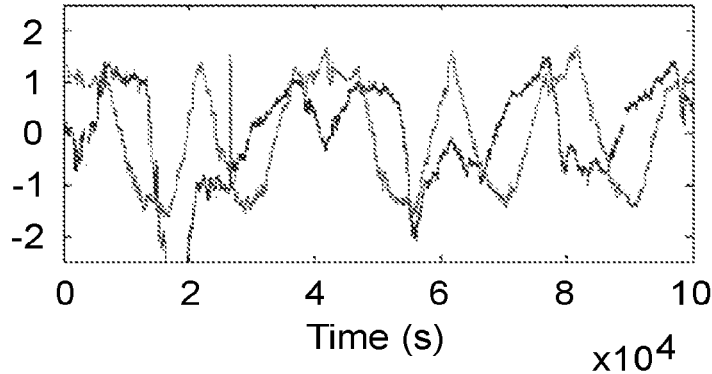
Figure 1F:
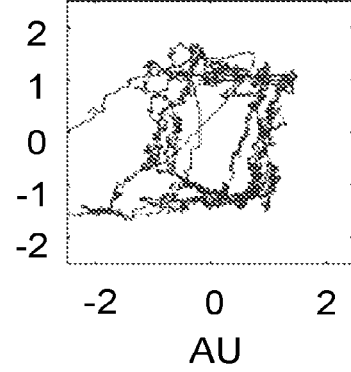

Visualization: Scatterplots. For visualization, scatterplots of the entire time series were created by plotting the 100,000 (x,y) pairs representing the two orthogonal components of the instantaneous angle of pupil reflection over 200 seconds. In neurologically intact controls, these figures look like boxes, reflecting the timing of the visual stimulus as it moved around the screen (FIG. 1d).

Quantitative data analysis and statistics. The x- and y-trajectories were fit with sinusoidal functions. The alternations in horizontal and vertical motion of the visual stimulus were thought to result in eye movement trajectories that were approximately sinusoidal with a period of 40 s, but with different phases for x and y. We further hypothesized that (1) the phase difference between x and y should be 45 degrees for neurologically intact controls, reflecting the ¼ cycle alternation of horizontal and vertical eye movements; and (2) the model would fit data from the neurologically intact control observers better than it fit data from the patient group.

Degree of correlation (r) with a sinusoid was calculated for 1 each time course. The square of this value (r2) is a measure of goodness of fit of the model to the data. The correlation values were used because they better suited for statistical analysis. Throughout the text, 'model fit' refers to the correlation values (r).

Phase was calculated as phase of the sine function that best fit the data. The 8 following complementary procedures were used to assess the statistical significance of any differences in these two measures (phase difference and model fit) as compared between the neurologically intact control observers and the test patient observers.

(i) Statistical Analysis 1: hyogthesis testing. For each measure, a statistical test was performed to determine whether the data from the test patient population could have come from the same underlying distributions as the data from the neurologically intact control population. For the phase measure, an unpaired t-test was used. For the sinusoidal fit measure, the Kruskal-Wallis analysis of variance (ANOVA) was used which is more appropriate for data that are not normally distributed.

(ii) Statistical Analysis 2: Fisher transformation. The correlation (r) values for each timecourse with the best fitting sinusoid were converted to z-scores using the Fisher transformation $((½)*\ln((1+r)/(1-r))$. This normalization enables to complete the third step of the analysis.

(iii) Statistical Analysis 3: classification. The Fisher z-scores provided an estimate of the probability of seeing a particular correlation value for a given timecourse if the underlying population of timecourses had zero mean correlation (the null hypothesis). The null hypothesis would be expected to be true for timecourses that were not fit well by sinusoids, e.g., timecourses from impaired observers. Timecourses with z-scores significantly above zero (e.g., well-matched to the stimulus trajectory) would be expected to come from unimpaired observers. A threshold of z=2 (corresponding to a significance level of alpha=0.05) was used to calculate the specificity and sensitivity of this test, as reported in the Results following.

Results

Eye movements were highly reliable and consistent across the group of neurologically intact control observers (FIG. 1 a,d; Table 1). Test patients exhibited a variety of patterns of eye movements (FIG. 1 b,c,e,f). Neurologically intact control observers exhibited consistent alternations of x and y eye movements over 5 cycles of aperture rotation (FIG. 1 a). Some test patients showed similar alternation (FIG. 1 b), while others did not (FIG. 1 c). In neurologically intact control observers (FIG. 1 d) and some test patients (FIG. 1 e), the eye movements traced out a box, reflecting the unchanging aperture trajectory across 5 cycles. Deviations from a box indicated impairment in eye movements (FIG. 1 f).

TABLE 1

Model fit and phase difference can distinguish between neurologically intact control populations and test patients.

| Measure | p-Value | Mean Value of Measure | | Standard Deviation | |
|---|---|---|---|---|---|
| | | Control | Test Patient | Control | Test Patient |
| Model Fit (r) | 0.000 | 0.98 | 0.87 | 0.01 | 0.18 |
| Phase Difference (degrees) | 0.008 | 45.8 | 41.4 | 2.2 | 27.7 |

To quantify the patterns of deviation from normal in the test patients, two measures were defined: phase difference and model fit (see Methods). Results were consistent with both hypotheses: (1) The sinusoidal model fit the data of the healthy observers better than it did the patients (p<0.001; Table 1); and (2) Healthy observers showed the hypothesized 45 degree phase difference between the horizontal and vertical trajectories, reflecting the pattern of movement of the visual stimulus; test patients did not (p<0.01; Table 1).

To test whether these eye movements might be used diagnostically, model fit was used to classify individual timecourses as coming from the group of neurologically intact controls vs. the group of test patients. Statistical thresholds were defined by converting correlation coefficients to normally-distributed z-scores, using the Fisher transformation. Each timecourse from all observers was classified based on the probability that it came from the null distribution (see Methods). The classification results exhibited 96% specificity and 52% sensitivity. Given that the test patients were a heterogeneous group selected from a neurosurgery clinic that treats patients who might have damage to either or both the peripheral and the central nervous systems, there is no reason to expect that the entire population would have problems that affected the ocular-motor system. Thus 52% sensitivity could be considered high for this test patient population.

Figure 2A:
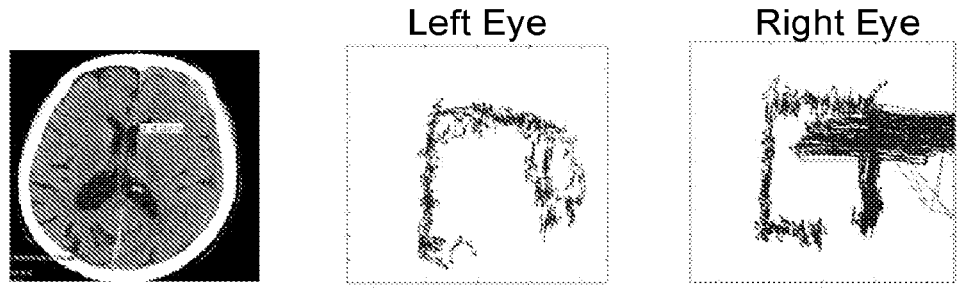
FIG. 2A is from a patient with a left subdural hematoma, first hospital visit after a fall.
Figure 2B:
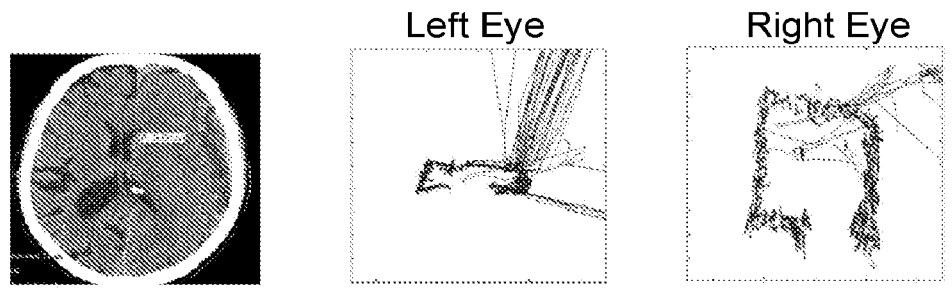
FIG. 2B is from the same patient one week later.
Figure 2C:
FIG. 2C is from the same patient two weeks later, after surgical intervention.

Several test patients were followed longitudinally, e.g., repeating the eye movement measurements before and after surgery, and/or during recovery from surgery (FIG. 2). These results suggested that eye movement traces could potentially be used as a marker of neurological impairment and recovery.

Discussion

Uncalibrated tracking may provide a quantitative measure of the ability to fixate, attend, and follow a stimulus. These date demonstrate that it is possible to collect reliable high-frequency eye movement data without first completing a spatial calibration for each observer. Many patients are not capable of calibrated eye tracking. The ability to track eye movements in these populations provides new insights about a variety of disorders that disturb the ocular-motor system, including but not limited to brain injury, stroke, and psychiatric disorders. Possible applications include clinical screening, diagnosis, monitoring the efficacy of treatment, and tracking progression of impairment and recovery.

Example 2

Materials and Methods

Subjects. Healthy subjects were recruited in a university setting in accordance with IRB approved protocols. All other subjects were recruited directly from our neurosurgical practice. Informed consent from the subject or their legal proxy was obtained for prospective data collection in all cases in accordance with IRB guidelines.

Eye Movement Tracking. The subjects' eye movements were recorded using an Eyelink 1000 monocular eye tracker (500 Hz sampling, SR Research). Healthy volunteers were seated 55 cm from the screen with their head stabilized using a chinrest. Subjects could be seated or lying down, on chairs, hospital beds, or stretchers. Stimulus was presented on average 55 cm from patient eyes, with the presentation monitor adjusted to match gaze direction. Some subjects used a chinrest, when it was comfortable for them to do so.

Innovations for tracking patients. Two innovations were provided to measure ocular motility in a patient population. The first was a paradigm, consisting of a stimulus and an analysis stream that allows interpreting raw eye position data. With few exceptions, eye movement studies analyze transformed gaze position, which involves a loss of information and excludes many patients from study. A novel algorithm for looking at pupil position directly, yielding information about ocular motility was developed. A device that can be brought to patients was provided. With few exceptions, eye movement data are collected using a fixed eye tracker at an unchanging location, which requires subjects to travel to the tracker and to use the chair and chinrest setup that goes with it. The SR Research Eyelink 1000 was adapted into a novel mobile system that allows flexibility in location and subject position, without sacrificing data quality.

Visual Stimulus. A music video that moved clockwise along the outer edge of a computer monitor starting at the upper left hand corner of the screen was provided. Spatial calibration was not performed, and the distance varied between subjects, so that the size of the stimulus in degrees may only be approximated. For a healthy subject seated 55 cm from the screen with good spatial calibration, the stimulus was presented in a square aperture with an area of approximately 16 degrees (approximately ⅛ of the size of the screen). This square aperture, within which a music video played continuously, moved across the screen at a constant speed, taking 10 s to cover each edge of the monitor. A full cycle took 40 s, and five full cycles were played, for a total of 200 s. A countdown video played in the starting position for 10 s before the music video began, to provide all subjects time to orient to the stimulus. The movie continued for an addition 10 seconds after the 200 s trial, to avoid boundary effects from contaminating the data. Only the 200 s of the music video comprising 5 cycles of 40 s each were used in all analyses. At a rate of 500 Hz, this yielded 100,000 samples of eye position over 200 seconds.

Data analysis: (1) Visualization. To create a snapshot of the data from the entire trial that provided a vivid indication of whether an individual subject's ocular motility differs from that of healthy controls, scatterplots of the entire time series were created by plotting the horizontal eye position along one axis and vertical eye position along the orthogonal axis. The 100,000 pairs of values (x,y) were plotted representing the two components of the instantaneous angle of pupil reflection (horizontal, vertical) over 200 seconds. In healthy controls, these figures look like boxes, reflecting the trajectory traveled by the aperture as it moved across the screen. (FIG. 3) These visualizations confirmed that the raw eye traces did conform to the square spatial trajectory of the stimulus, except in cases of neurological damage.

Data analysis: (2) Time vs. Space. Without spatial calibration, exact measurements of error in the spatial domain are impossible. This problem was avoided by looking at the eye movement trajectories in the time domain, rather than the spatial domain. By using a constantly changing stimulus (a continuously playing movie) with a periodic envelope (the aperture trajectory), it was possible to look at relative eye movements over time. Effectively, each subject's mean trajectory over the path of the aperture served as its own calibration.

Data analysis: (3) Statistics. In order to quantitatively assess the statistical significance of our results, the distribution of certain measurements in the control population was determined, and each subject was compared with these control distributions for each measure. The stimulus trajectory was divided into four time components: The first arm consisted of five repetitions of the first 10 seconds of each rotation cycle (e.g., seconds 1:10, 41:50, 81:90, 121:130, and 161:170). The second, third and fourth arms were defined accordingly. Two variables were evaluated: the relative variance in each arm, and the relative integrity of each arm. Relative variance was calculated as mean variance across 5 repetitions within an arm divided by variance of the whole time course. Integrity was calculated as the percent of missing values in each arm. We defined 2 tests based on these measurements, and performed the same tests in the controls and the patients. The results of these tests in the control population were used to determine the control distributions. The results of these tests for each patient were compared to the appropriate control distribution, and confidence intervals were defined as follows.

Integrity. For the integrity measure, each patient's pair of values from arms 1 (the top of the box) and 3 (the bottom of the box) was z-scored using the mean and standard deviation calculated from the control population. The resulting score indicated how different the patient values were compared with the control values, in units of standard deviations. Because 95% of all values in a normal distribution lie within two standard deviations of the mean, a z-score of 2 was used as a significance threshold. Patients with z-scores above 2 in either or both arms were thus judged to have significant disturbances of ocular motility.

Relative variance. Because relative variance is a ratio, it cannot be analyzed using z-scores, since the assumption of a normal distribution does not hold for ratios. Instead, 5,000 point distributions were generated using a bootstrapping method that took 5,000 samples from 25 values randomly chosen with replacement from the 45 control values. For each subject, the relative variance in arms 1 and 3 were compared respectively with the corresponding control distribution, and the percent of the control distribution with variance below that of the test value was determined. A p-value of 0.05 (a widely accepted measure of statistical significance) corresponds to 95% of control values falling below the test value. Thus, subjects with variance higher than 95% of the values in the control distributions were determined to have significant disturbances of ocular motility.

Units. The units of relative variance are related to size in degree of visual angle, but are not exactly identical to degrees of visual angle, because there was no spatial calibration. These may be referred to as time-degrees units.

Results

Successful tracking. Visualization of the eye movement trajectories across healthy controls and patients confirmed that the method successfully measured eye movements without recourse to traditional calibration techniques (FIG. 1).

Control distributions. As expected, the control distributions for the integrity measurements were normally distributed with a mean of 0.2 and an average standard deviation of 0.05 (5% deviation). The control distributions of relative variance peaked at 0.25 (reflecting equal variance across the four arms).

Patient measurements. The integrity measures for the 'top' vs. 'bottom' arms of the trajectory for each subject, in units of standard deviation, as compared with the control distributions as described above were calculated. Subjects with cranial nerve palsies or mass effect showed defects in integrity of eye tracing box trajectory. Subjects with relatively greater cranial nerve II palsies due to either compression or papilledema showed streaking vertical lines due to scanning vision.

Example 2

Early Detection of Transtentorial Herniation as Manifested by Cranial Nerve III Palsy and Detection of Concussion Discussion Eye movement tracking for neuropsychiatric and brain injury research (Maruta, et al. *Journal of Head Trauma Rehabilitation* (2010) 25: 293-305; Heitger, et al. *Brain* (2009) 132: 2850-2870) has traditionally been based on spatial calibration. With calibration, the eye-tracker measures the relative position of pupil and corneal reflection for a period of about 400-800 ms while the subject looks at a target or targets of known position to generate meaningful spatial coordinates during subsequent pupil movement. Calibration requires subject cooperation and precludes detection of anatomically dysfunctional ocular motility. We developed a novel technique for eye movement tracking without spatial calibration which can, theoretically, assess the function of the oculomotor nerve (cranial nerve III). Among its other functions, the oculomotor nerve innervates the superior and inferior recti muscles of the orbit, raising and lowering the pupil. Compression of the nerve while it courses through the tentorial notch medial to the temporal lobe occurs with impending transtentorial herniation, a common mechanism of death from supratentorial mass effect due to tumors, stroke, hemorrhage or trauma. (Adler, et al., *Journal of Neurosurgery* (2002) 96: 1103-1112) These data demonstrate that recording of subject eye movements during watching of a 200 second moving music video detected decreased vertical pupillary movement amplitude in patients with supratentorial mass lesions resulting in radiographic compression of the IIIrd nerve after its exit from the pontomesencephalic junction and prior to its entry into the cavernous sinus. These decreases in vertical amplitude were subclinical and not seen in control subjects or surgical patients without mass effect on the third nerve and were also reversible upon resection of their causative supratentorial lesions with concordant volumetric elimination of mass effect. These results demonstrate that non-spatially calibrated eye movement tracking may be useful for detection of transtentorial herniation in awake patients with supratentorial mass lesions.

Methods

Figure 20D:
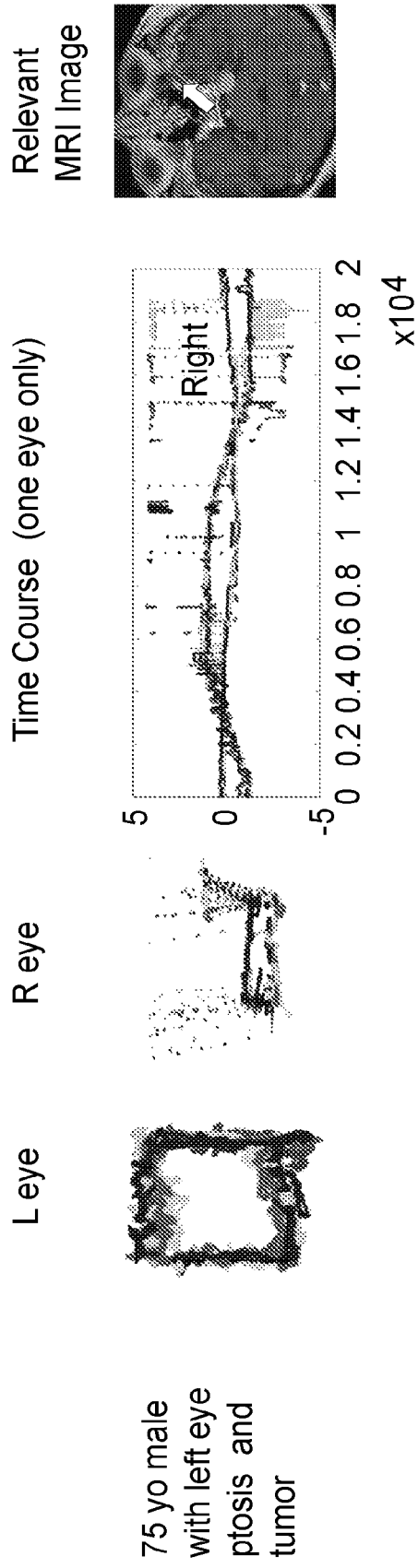
FIG. 20 (A, B, C, D, E) demonstrates tracking eye movements to detect ocular dysmotility. The box plots show each cycle as a different color, sequentially red, green, cyan, magenta and blue. The time courses plot Cartesian coordinates over time to show percent change in eye position for each of the five 40 second cycles. The top row is a normal control. Subsequent rows depict tumors compressing CN II, the cavernous sinus, and the peripontine area in a patient with ptosis, no diplopia and normal motility. The final row is a patient without evidence of any nerve palsy who sustained an inferior orbital rim fracture with transient diplopia that resolved within one year of the surgical repair.
Figure 20E:
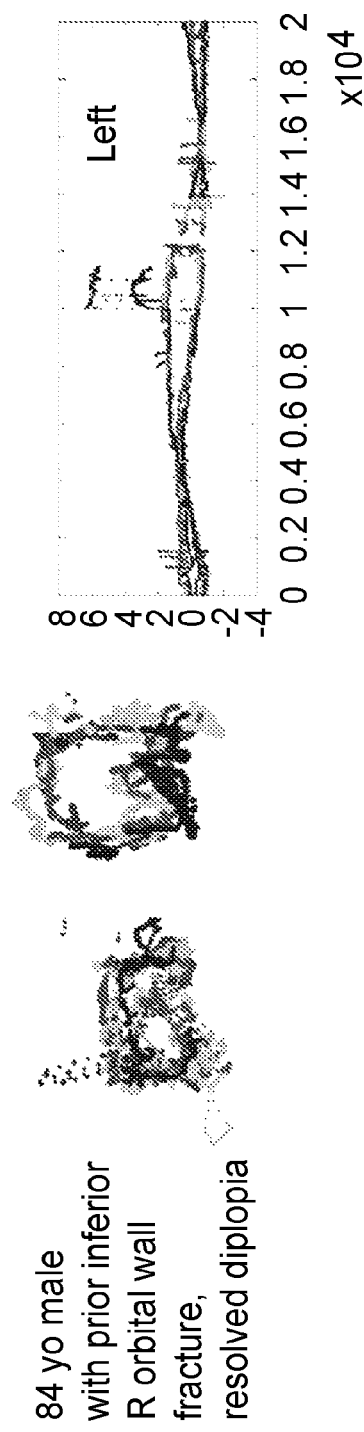

In order to overcome the constraints of spatial calibration, subjects' eye movements were recorded with an Eyelink 1000 eye tracker at a relatively fixed distance from a computer monitor over a fixed period of time. The visual stimulus provided was the Shakira music video Waka-Waka played continuously in a square aperture with an area approximately ⅛ the screen size while moving clockwise along the outer edges of the monitor for five complete cycles of 40 seconds each. The eye tracker sampled pupil position at 500 Hz, yielding 100,000 samples over 200 seconds. Scatterplots of the entire time series were created by plotting the 100,000 (x,y) pairs representing the two orthogonal components of the instantaneous angle of pupil reflection over time to create 'box trajectories' that reflected the temporal nature of the pupillary movement. In control subjects, these figures look like boxes, reflecting the timing of the aperture as it moved around the screen (FIG. 20).

Tracking of people with known lesions was compared to normal controls. A patient with a tumor compressing a unilateral optic nerve resulting in no light perception in that eye had intact bilateral tracking since the afferent from the contralateral eye was sufficient to drive ocular motility in both eyes ($2^{nd}$ row, FIG. 20). A patient with unilateral ophthalmoplegia due to a large tumor invading the cavernous sinus had decreased amplitude both vertically and horizontally ($3^{rd}$ row, FIG. 20). A patient denying diplopia with a peripontine mass and grossly intact ocular motility on slit lamp examination, but with a ptosis, also showed decreased vertical amplitude (FIG. 20). Ptosis in this patient may be a consequence of disruption of the superior division of the oculomotor nerve en route to the levator palpebrae superioris. A patient without a known IIIrd palsy, but with a history of inferior orbital wall fracture resulting in transient diplopia five years prior also had decreased vertical amplitude on eye-tracking (FIG. 20, bottom row).

In every patient that was eye-tracked with any deficit, the abnormal eye-tracking findings occurred while tracking the eye contralateral to the anatomical pathology. This has occurred consistently in the entire database of patients.

Figure 21B:
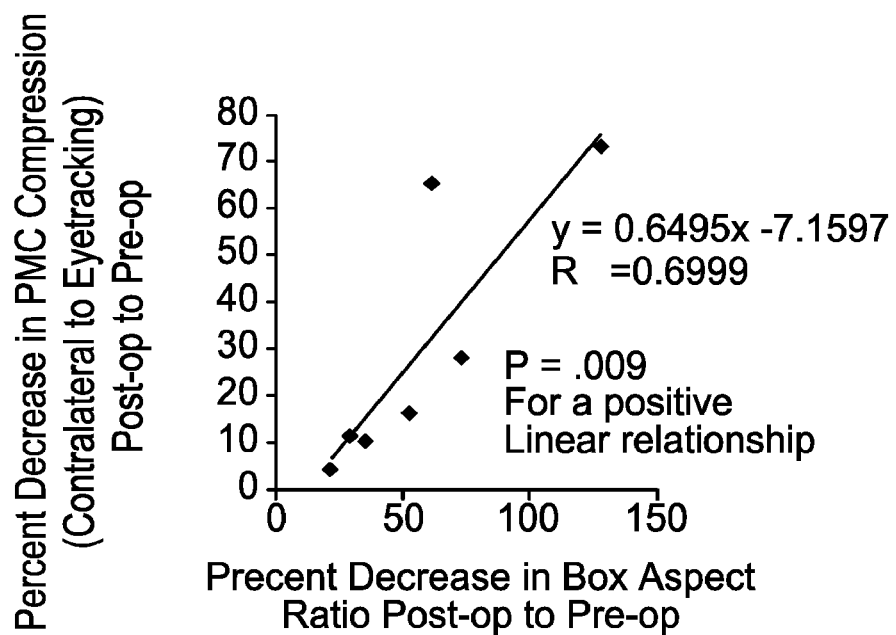
FIG. 21 (A, B) demonstrates that decreased perimesencephalic volume is associated with decreased vertical amplitude on eye movement tracking in 5 patients with supratentorial mass lesions. All five patients with decreased perimesencephalic volume were confirmed by 2 independent radiologists to have increased uncal mass effect. A. Preoperative tracking of these patients was statistically significantly associated with decreased aspect ratio (height/width) relative to themselves postoperatively (p=0.008), to 2 patients presenting with supratentorial mass lesions that did not have perimesencephalic compression volumetrically or radiographic uncal mass effect, to 5 patients with vestibular schwannomas, and to 11 ophthalmology clinic control patients. B. There was a linear relationship between percent decrease in perimesencephalic compression and percent decrease in aspect ratio from postoperative to preoperative (p=0.009).

These data represent a prospective observational study of patients with inclusion criteria of: supratentorial mass lesion apparent on radiographic imaging, clinical necessity for surgical resection, and able to consent for and engage in eye tracking. Exclusion criteria were: visual acuity worse than light perception, neurologic or hemodynamic instability, papilledema or conduction abnormality of the optic nerve, bilateral compression of optic nerves resulting in decreased visual acuity, visual field deficit, sellar lesion, and cavernous sinus invasion and dementia. Five of seven patients with supratentorial mass lesions had reduced perimesencephalic volume radiographically and demonstrated reduced vertical pupillary amplitude on eye-tracking relative to themselves postoperatively and relative to the two of seven patients with supratentorial lesions with unchanged perimesencephalic cistern volumes (FIG. 21, left panel). Since the actual space around the third nerve as it travels from the interpeduncular cistern at the pontomesencephalic junction to the cavernous sinus is difficult to quantify with great accuracy, we assessed patient films for reduction in perimesencephalic cistern volume relative to the maximal volume postoperative scan as measured by algorithmic volumetric analysis of CT scans using established methodology (Yang, et al. *Brain Inj* (2012) originally adapted from MRI analysis. (Mikheev, et A, *J Magn Reson Imaging* 2008; 27:1235-1241). Surgical control patients were those with supratentorial mass lesions not resulting in decreased perimesencephalic cistern volume (n=2) and those undergoing resection of cerebellopontine angle tumors (n=5). Non-surgical control patients were approximately age-equivalent volunteer subjects without significant neurologic disease documented to have intact ocular motility, pupillary reaction and optic nerve function upon evaluation in ophthalmology clinic (n=11). Decompression of the perimesencephalic cistern was associated with improvement in the aspect ratio (height/width of the eye tracking trajectory; FIG. 21, right panel, and FIG. 30).

To confirm that the volumetric analysis was consistent with radiographic findings two experienced neuroradiologists blinded to the eye-tracking results evaluated the patients' preoperative CT scans for evidence of IIIrd nerve compression (supplementary information). Both radiologists were in accord that the two patients with supratentorial lesions without compression via volumetric analysis also did not have compression on direct review of the imaging.

Patients undergoing resection of supratentorial mass lesions without any evidence of preoperative perimesencephalic cistern compression or uncal herniation trended slightly towards a more decreased aspect ratio than their postoperative selves or the ophthalmology controls. It may be that multiple factors other than direct compression of the oculomotor nerve are impacting ocular motility in these patients. Elevated intracranial pressure delays axoplasmic transport along cranial nerve II in experimental studies. (Balaratnasingam, et al., *Brain Research* 2011; 1417: 67-76) Mass effect from the lesions may be causing sufficient elevation in intracranial pressure to delay axoplasmic transport along cranial nerves impacting ocular motility.

Figure 22C:
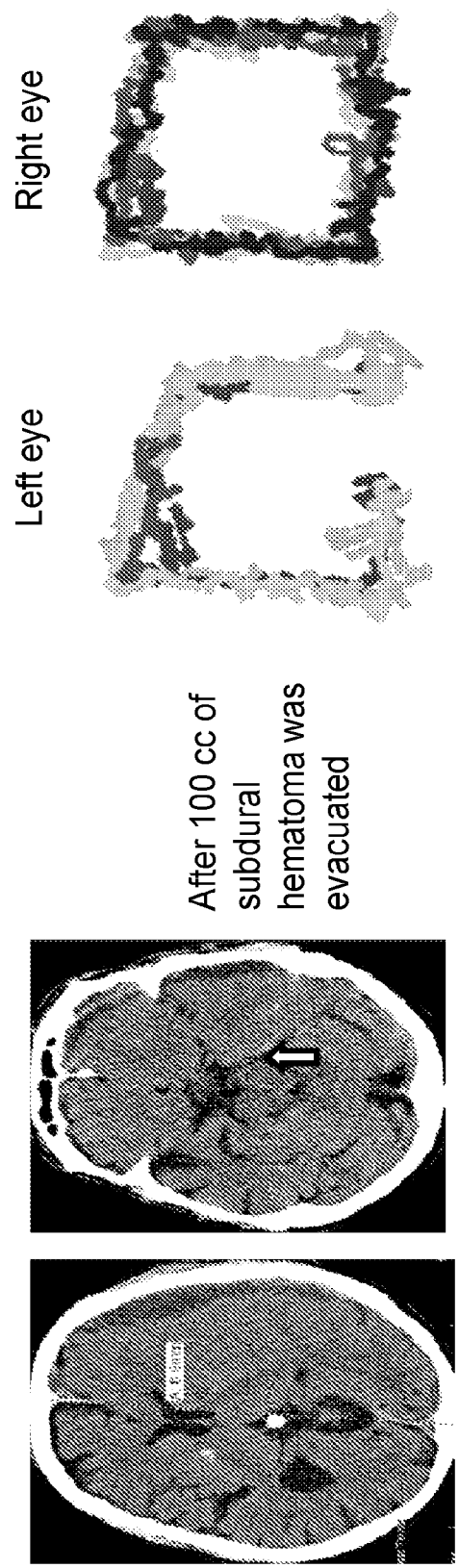
FIG. 22 (A, B, C) shows exacerbation and reversibility of pupillary vertical amplitude in a patient with subdural hematoma. A. An 86 year old male with a history of cataracts presented with headache several weeks after a fall. Initial axial CT showed a small subdural hematoma (top row, left) with an open perimesencephalic cistern (red arrow). B. Eight days later his headache became exacerbated, and repeat imaging demonstrated that the subdural hematoma had expanded, creating mass effect on the brain and pushing the medial aspect of the temporal lobe into the perimesencephalic cistern (middle row, red arrow). C. A twist-drill drain was placed and 100 cc of subdural fluid were evacuated resulting in resolution of the mass effect on the perimesencephalic cistern (bottom row, red arrow).

One patient in the series deteriorated clinically after initial presentation to the clinic. Serial eye movement tracking of this patient with a left chronic subdural hematoma from presentation, to exacerbation of mass effect, through surgical evacuation was performed. Impingement on the third nerve by the medial aspect of the temporal lobe resulted in decreased vertical amplitude, which occurred more frequently with exacerbation of the mass effect from the subdural hematoma and resolved with its treatment (FIG. 22). Note that on presentation only one of the five visual stimulus cycles demonstrated a compression suggestive of a IIIrd nerve palsy. It may be that transient waves of increased pressure in the cistern impact the function of the IIIrd nerve immediately and temporarily.

The patient with the greatest quantitative difference in perimesencephalic volume between the pre and postoperative CT scan had bilateral decreases in pupillary vertical amplitude on eye-tracking. This patient presented with a fall resulting in a right frontoparietal skull fracture and small epidural hematoma causing almost nil subfalcine herniation (FIG. 23, top CT image) but reduction in perimesencephalic cistern volume to 27% of postoperative on the right side and 35% of postoperative volume on the left (bottom CT image).

None of the patients with supratentorial lesions found to have restricted vertical amplitude on eye tracking reported diplopia or other symptoms of disconjugate gaze. All of the patients were reported to have normal ocular motility on examination by a neurosurgeon or by ophthalmologic slit lamp, which suggests that the palsies are subclinical.

These data demonstrate that the methods described herein provide an algorithm for detecting subclinical third nerve palsy that may be clinically useful for the detection of transtentorial herniation. Since the IIIrd nerve innervates the medial rectus, and there is normal width of the eye box trajectory in patients with radiographic perimesencephalic compression, it may be that the IVth nerve is sufficient for medial rotation of the pupil. Additional evidence that the third nerve is responsible for the noted eye tracking changes will be obtained in the future by evaluating stationary pupil size data.

The methods described herein differ from a report of uncalibrated tracking using static stimuli for on-target and off-target fixations in a population of minimally conscious and persistently vegetative patients that have open eyes. (Trojano, et al. *J. Neurol*, (2012)) The moving images shown within an aperture that moves periodically allows assessing both coarse and fine eye movement characteristics in both controls and neurologically impaired subjects. Unlike other studies (Maruta, et al. *Journal of Head Trauma Rehabilitation* 2010; 25: 293-305; Trojano, et al. *J. Neurol*, 2012; Contreras, et al., *Brain Research* 2011; 1398: 55-63; Contreras, et al. *Journal of Biological Physics* 2008; 34: 381-392) the presently described methods did not use saccade count or spatial accuracy which requires transformation of raw data by a series of scaling and rotating processes whose effectiveness depends on the ability of their subjects to follow precise commands reliably. The methods described herein also differ from gaze estimation, which requires either a fixed head position or multiple light sources and cameras to localize the pupil. (Guestrin, et al., *IEEE Transactions on Bio-Medical Engineering* 2006; 53: 1124-1133).

Because so many different cortical functions are required for watching a video, any process impeding global cranial function or specific cranial nerve function will likely be revealed by the technique. Tracking may be confounded in patients with a history of prior brain insult, who are intoxicated, or are under the influence of pharmacologic agents. Patients' cognitive abilities, attention span and distractibility may impact the quality of ocular motility data. Given the diverse baseline ocular pathology of hydrocephalic patients (Dennis, M. et al. *Archives of Neurology* 1981; 38: 607-615; Zeiner, et al., *Childs Nerv Syst* 1985; 1: 115-122; Altintas, et al., *Graefe's archive for clinical and experimental ophthalmology=Albrecht von Graefes Archiv fur klinische und experimentelle Ophthalmologie* 2005; 243: 1213-1217), tracking results may be compared to each patient's own normative data. Younger infants who cannot yet track may not be candidates for eye movement tracking based assessment.

The methods described herein assess physiologic functioning of the central nervous system and thus are different from imaging technologies enabling visualization of brain anatomy. Uncalibrated ocular motility tracking assessment does not require that the subject explicitly consent to being tracked prior to assessment of their central nervous system functioning, and thus raises ethical considerations. Dementia, schizophrenia, amyotrophic lateral sclerosis, autism and Fragile X are among the numerous diseases with characteristic anomalies detectable using eye movement tracking technology (Sharma, et al. *Archives of Neurology* (2011) 68: 857-861; Pelak, *Current Neurology and Neuroscience Reports* 2010; 10: 440-447; Hicks, et al., *Progress in Brain Research* 2008; 171: 555-558; Kennedy, et al., *Neuropsychologia* 2010; 48: 3392-3398; Levy, et al., *Current Topics in Behavioral Neurosciences* 2010; 4: 311-347)

Aspect Ratio. Elapsed time quantitation enables localization of the video aperture during measurement of eye position. Box height=median top value−median bottom value while the video traverses top and bottom. Similarly the width of the box is calculated based on where the pupil is when the video aperture is on the right and left sides. Aspect ratio=height/width. (FIG. 28).

Perimesencephalic cistern volume. To correct for variable angulation with respect to axial, coronal and sagittal planes that could be introduced by misalignment of the head between scans, each CT volume was realigned and resampled to a standard (template) coordinate system by marking in 3D space the left eye lens (LE), right eye lens (RE) and the junction of the superior colliculi (C). In the template space these three corresponding structures LE' RE' C' were positioned symmetrically such that the principal axis of the brain stem was in the z direction (across plane). The rigid body (volume-preserving) transformation T that best mapped the triangle <LE RE C> onto the triangle <LE' RE' C'> was then computed. The transformation T was used to resample the CT volume to the template space. The cistern was segmented into the template space by placing a cylinder of radius 20 pixels centered on the center of the brain stem extending from pineal gland to tuberculum sella. For each voxel within the cylinder we computed the voxel's partial volume Pv of CSF according to its attenuation A measured in Hounsefield units (Hu): Pv=(A_brain −A)/(A_brain −A_water). Here A_brain=48 Hu, A_water=0 Hu. Pv was constrained to [0-1]. The cistern volume was computed as the sum of Pv values within the cylinder multiplied by voxel volume excluding the suprasellar cistern.

Patient case details and radiologist interpretations. For the purposes of this study, the radiologists were asked to look at the preoperative CT images and comment on whether or not there was mass effect upon the IIIrd nerve.

Statistical Analyses

Aspect ratio was calculated as described in the methods summary above using MATLAB programming for management of the 100,000 data points per eye movement trajectory. Ratios were compared using a two-tailed student t-test, paired, two-sample for pre vs post-operative data comparisons and unpaired t-tests for comparison between the unequal n groups of surgical patients versus ophthalmologic clinic controls.

Mean pupil size was calculated by obtaining the mean of the 100,000 data points per eye tracking trajectory using MATLAB programming. Means were compared using paired two-tailed t-tests for comparison between pre and postoperative data.

Supratentorial Cases with Perimesencephalic Compression.

Case 1: (FIG. 22) The patient is an 86 year old right handed male with a medical history of hypertension, hyperlipidemia mild chronic renal insufficiency and an ophthalmologic history of bilateral cataract surgery (2 years and 8 years prior), pseudophakia and scleral buckling. He had a baseline visual acuity of 20/25 (right eye) and 20/30 (left eye). The patient took 81 mg of aspirin per day prophylactically. The patient fell and presented several weeks later with headache but was otherwise neurologically well. A head CT was performed and demonstrated a small left sided subdural hematoma. Aspirin was discontinued and platelets were transfused. The headache resolved spontaneously, and the patient elected to observe this lesion. Eight days later the headache became exacerbated, and a repeat CT scan demonstrated enlargement of the hematoma. The patient continued to remain intact on neurologic examination, exhibiting neither neglect nor pronator drift. He had surgical pupils which remained symmetric. The patient underwent subdural hematoma drainage, during which 100 cc of fluid was extracted using a closed twist-drill drainage system. His headaches resolved and he became asymptomatic. The patient was discharged to home after participating in physical therapy.

Perimesencephalic cistern compression (on immediate preoperative CT scan): Right cistern 80% of baseline, left cistern 61% of baseline.

Radiologist #1: "The brainstem is shifted right, there is medialization of the uncus and it may barely touch cisternal CN III. Separately there is mass effect on the left cavernous sinus by the uncus (loss of CSF cleft)"

Radiologist #2: "The patient has a full uncus with medial displacement. There is mass effect on the cistern, but no overt compression of CN III."

Figure 24A:
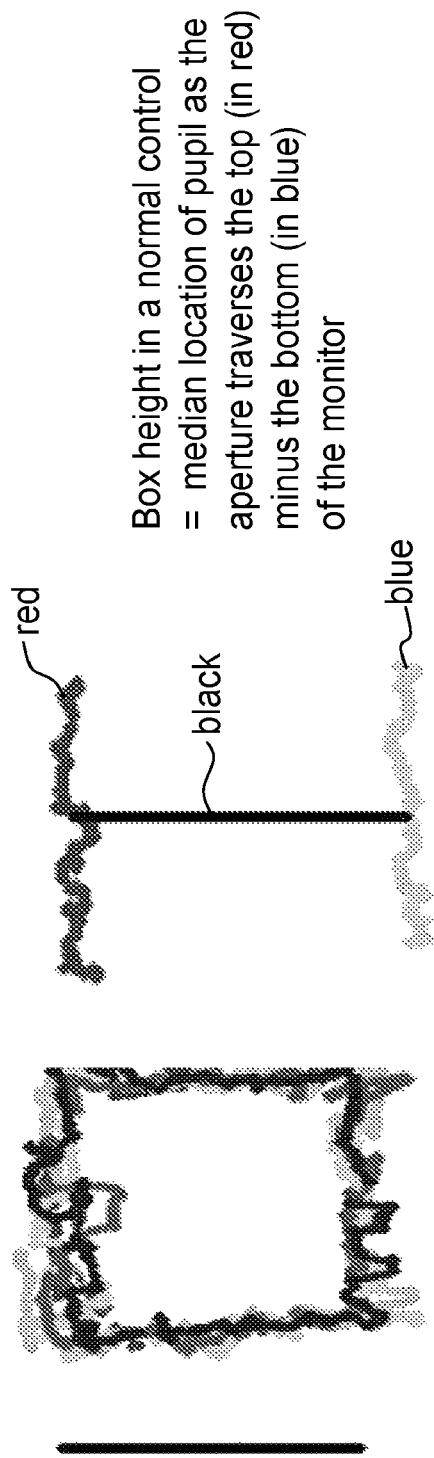
FIG. 24 (A, B) also represents the eye movement tracking of a 62 year old patient with an acute epidural hematoma and bilateral perimesencephalic compression after a fall. A.
Figure 24B:
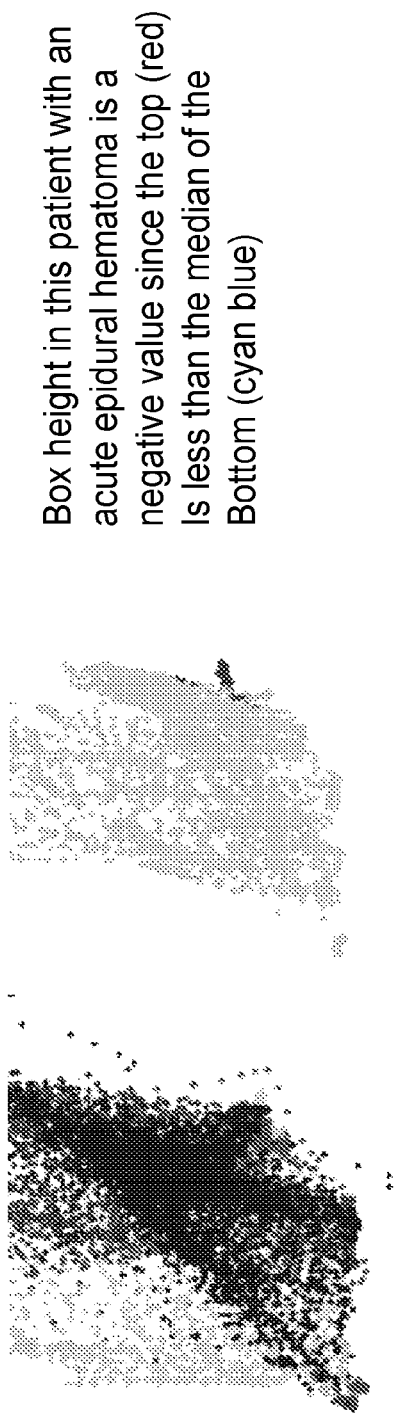

Case 2: (FIG. 23 and FIG. 24) The patient is a 62 year old right handed male with a past medical history of goiter/iatrogenic hypothyroidism, hypertension and hyperlipidemia and an ophthalmologic history of glaucoma controlled with latonoprost drops. He had 20/20 vision bilaterally. He presented with a fall and loss of consciousness persisting a few minutes. At presentation he was awake, alert, and had fluent speech. His pupils were equal and extra-ocular movements remained intact. His head CT showed a small frontoparietal epidural hematoma underlying a stellate skull fracture. Eye movement tracking was performed. Five hours later his examination deteriorated and he developed drowsiness, dysarthria, left sided neglect and a left pronator drift. His pupils remained equal and extraocular movements remained intact by examination. He was taken to the operating room for craniotomy and evacuation of epidural hematoma and cranial plating of the skull fracture. Postoperatively his left sided neglect and pronator drift resolved over the subsequent 48 hours. He scored 13/50 on the Executive Interview 25 Assessment Test (EXIT) on postoperative day four. Eye tracking was repeated on postoperative day 7. He was discharged to home after one week of inpatient rehabilitation.

Perimesencephalic cistern compression (on preoperative CT scan): Right cistern 27% of baseline, left cistern 35% of baseline.

Radiologist #1: "There is contact with CN III on the right side."

Radiologist #2: "There is no evidence of overt CN III compression."

Case 3: (FIG. 25) 74 year old diabetic hypertensive male with renal insufficiency, bilateral cataracts and 20/25 vision bilaterally, presented with impaired mobility due to right lower extremity weakness. He denied head trauma but reported having fallen three months prior without hitting his head. On examination he was awake and alert with a right pronator drift and 4/5 right sided hemiparesis of the upper and lower extremities. His left side was intact. His pupils appeared equal and he had intact extraocular motility on examination. Eye movement tracking was performed. Twist-drill drainage of the subdural hematoma was performed and 130 cc of fluid was extracted. He was discharged to home after inpatient rehabilitation.

Perimesencephalic cistern compression (on immediate preoperative CT scan): Right cistern 86% of baseline, left cistern 70% of baseline.

Radiologist #1: "The left uncus is shifted slightly medially and may contact CNIII."

Radiologist #2: "The uncus is medially deviated; there is no overt compression."

Case 4 (FIG. 26) 63 year old 100 pack-year smoking male who had declined to see a physician for the duration of his adult life, and thus reported no relevant medical or ophthalmologic history, presented to the emergency room with a cough and flu-like illness. On examination he was noted to be disoriented and have a mild L hemiparesis. Pupils were equal and reactive, extraocular movements appeared intact. Head CT demonstrated a right frontal mass, and chest radiograph showed a large left upper lobe chest mass. The patient was administered decadron 10 mg po q6 hours and a CT chest/abdomen/pelvis and brain MRI (shown) was obtained. Eye movement tracking was performed 48 hours after admission, directly prior to right frontal craniotomy for resection of a moderately well-differentiated squamous cell carcinoma metastasis. A radiographic gross total resection was performed. The patient went home one week after his craniotomy and ultimately underwent radiation therapy to his whole brain. He declined treatment for the lung mass and expired 7 months after his initial diagnosis.

Perimesencephalic cistern compression (on immediate preoperative CT scan): Right cistern 77% of baseline, left cistern 73% of baseline.

Radiologist #1: "There is subtle shift of the uncus towards the midline. It likely does not contact cisternal CNIII, but may press on the ipsilateral cavernous sinus, since the CSF cleft adjacent to the sinus is gone."

Radiologist #2: "The uncus is medially deviated; there is no overt compression on CN III."

Case 5 (FIG. 27) The patient is a 63 year old male with diabetes, hypertension, hypercholesterolemia, atrial fibrillation on coumadin, congestive heart failure, post-traumatic stress disorder, renal failure on dialysis, chronic obstructive pulmonary disease and coronary artery disease. He presented with confusion while receiving hemodialysis for his renal failure. Ophthalmic history was significant for proliferative retinopathy. He had visual acuity of 20/25 in the right eye and 20/40 in the left eye. On physical examination at presentation he was neurologically well, without neglect or pronator drift. Extraocular movements were intact, pupils were equal. Head CT demonstrated a right sided mixed-density subdural hemorrhage. Eye tracking was performed. Coumadin was stopped and fresh frozen plasma administered. Two days after presentation twist-drill drainage was performed and 176 cc of subdural fluid was evacuated. The patient remained neurologically well and returned to his assisted living residence two days later.

Perimesencephalic cistern compression (on immediate preoperative CT scan): Right cistern 36% of baseline, left cistern 29% of baseline.

Radiologist #1: "The right uncus is shifted and impacts the cisternal portion of CN III before it passes under the petroclival ligament."

Radiologist #2: "The uncus is medially deviated and full."

Supratentorial Cases without Perimesencephalic Compression by Volumetric Analysis.

Case 6 (FIG. 28) 67 year old male with a past medical history of prostate cancer, hypertension, hyperlipidemia, alcoholism in remission, and gunshot wound to the left shoulder with retained missile fragment. His ophthalmic baseline was 20/40 vision in the right eye and 20/50 in the left eye. He presented with 2 months of stuttering and right arm and hand weakness. He had a witnessed seizure on the day of presentation that began with shaking of the right upper extremity and progressed to generalized tonic-clonic activity. On examination he had intact pupils and extraocular movements. His speech was slow with paraphasic errors and difficulty with repetition and naming. Head CT with contrast revealed a left fronto-temporal cystic mass. The patient underwent awake stereotactic drainage of the cyst, which revealed necrotic cells and was non-diagnostic for malignancy, followed by awake stereotactic craniotomy with speech mapping for resection of a glioblastoma multiforme. Gross total resection was achieved radiographically. The patient had preserved speech but mild hemiparesis postoperatively and participated in rehabilitation prior to discharge home. He received temodar and radiation therapies as an outpatient and remained independent in activities of daily living with no tumor recurrence at four months postoperatively.

Radiologist #1: "Cisterns patent. No uncal shift. No contact with CN III."

Radiologist #2: "No evidence of CN III compression."

Case 7 (FIG. 29) 65 year old male with a past medical history of hypertension, hyperlipidemia, coronary artery disease and post-traumatic stress disorder, with no known ophthalmic disorders and visual acuity of 20/20 bilaterally presented 2 weeks after left parietal craniotomy for a esophageal junction metastasis by an outside surgeon with worsening right hand coordination and ataxia. On examination the patient had right pronator drift and hemineglect. CT revealed edema at the surgical site and MRI revealed a peripherally enhancing collection in the previous tumor cavity. Eye tracking was performed, and then the patient was taken to the operating room for re-exploration craniotomy and evacuation of an abscess deep to the dura. He was treated with antibiotics for 12 weeks postoperatively.

Radiologist #1: "Cisterns patent. No uncal shift. No contact with CN III."

Radiologist #2: "No evidence of CN III compression."

Vestibular Schwannoma Surgical Control Cases (FIG. 36)

Three patients underwent resection, and one had gamma knife radiation for vestibular schwannoma tumors. A fifth patient opted for serial observation.

Ophthalmology Clinic Control Cases:

Eleven patients ranging in age from 56 to 87 years old were evaluated in ophthalmology or neuro-ophthalmology clinic. These patients were selected as non-surgical controls.

Example 3

Quantitation of Disease Severity for Normal Pressure Hydrocephalus and Diagnosis of Shunt Malfunction/Optimization of Valve Pressure for the Treatment of Normal Pressure Hydrocephalus Dementia is a disease with numerous etiologies and devastating consequences. Spatially calibrated eye movement tracking of demented subjects reveals impaired smooth pursuit function. We developed a novel technique for eye movement tracking during watching of a moving video that does not rely on spatial calibration. Here we show that subjects with normal pressure hydrocephalus demonstrated decreased tracking variability after cerebrospinal fluid diversion relative to their preoperative state. This decrease in variability correlated with improvements in gait and was not seen in surgical patients without normal pressure hydrocephalus or serially tracked control subjects. Our results suggest that cerebrospinal fluid diversion improves the ability of normal pressure hydrocephalics to perform less variable non-spatially calibrated eye movement tracking, and that eye tracking while watching a movie or television can be used to assess shunt function.

Impaired smooth pursuit eye movement tracking is seen in demented patients versus normal elderly controls (Hutton, et al., *Neurology* (1984) 34: 99-102) and has been shown to be an early indicator of presenile and Alzheimer's dementia (Muller, et al., *Int J Psychophysiol* (1991) 11: 167-177; Muller, et al., *European archives of psychiatry and clinical neuroscience* (1991) 241: 46-48) Demented patients also have impaired eye-hand visuomotor coordination (Verheij, et al., *J Alzheimers Dis* (2012) 30: 131-143) and impaired visual memory (Lagun, et al., *Journal of neuroscience methods* (2011) 201: 196-203).

Normal pressure hydrocephalus (NPH) often has an unknown etiology and is generally characterized by progressive onset of gait disturbance, dementia and incontinence (Bret, et al., *Journal of neurology, neurosurgery, and psychiatry* (2002) 73: 9-12). It is a heterogeneous disorder with noted overlap with Alzheimer's as evidenced by cortical biopsy specimens obtained at the time of CSF diversion for NPH revealing $A\beta$ and $\gamma$ proteins (Leinonen, et al. *Neurodegenerative diseases* 2012; 10: 166-169). Eye movement tracking findings in patients with NPH have not previously been reported.

Since impaired smooth pursuit eye movement tracking is noted in demented patients with Alzheimer's disease, we hypothesized that impaired tracking would also be noted in patients with NPH dementia, and that tracking would be improved after CSF diversion. Because some demented patients are unwilling or unable to follow instructions briskly and consistently enough to participate in the spatial calibration process necessary for eye movement tracking, we developed a technique for non-spatially calibrated tracking that can be performed while the subject watches television or its video equivalent.

We performed this non-spatially calibrated tracking pre and postoperatively in patients undergoing CSF diversion for NPH. In order to demonstrate that a learning effect from serial tracking was not responsible for the improvements in tracking in the NPH population, we also serially eye tracked control patients undergoing unrelated surgeries or no surgery at all.

Methods

With calibration, the eye-tracker measures the relative position of pupil and corneal reflection for a period of about 400-800 ms while the subject looks at a target or targets of known position to generate meaningful spatial coordinates during subsequent pupil movement. In order to overcome the constraints of spatial calibration, we recorded subjects' eye movements with an EyeLink eyetracking camera at a relatively fixed distance from a computer monitor over a fixed period of time. The visual stimulus was the Shakira World Cup soccer music video Waka-Waka played continuously in a square aperture with an area approximately ⅛ the screen size while moving clockwise along the outer edges of the monitor for five complete cycles of 40 seconds each. The eye tracker sampled pupil position at 500 Hz, yielding 100,000 samples over 200 seconds.

Figure 3:
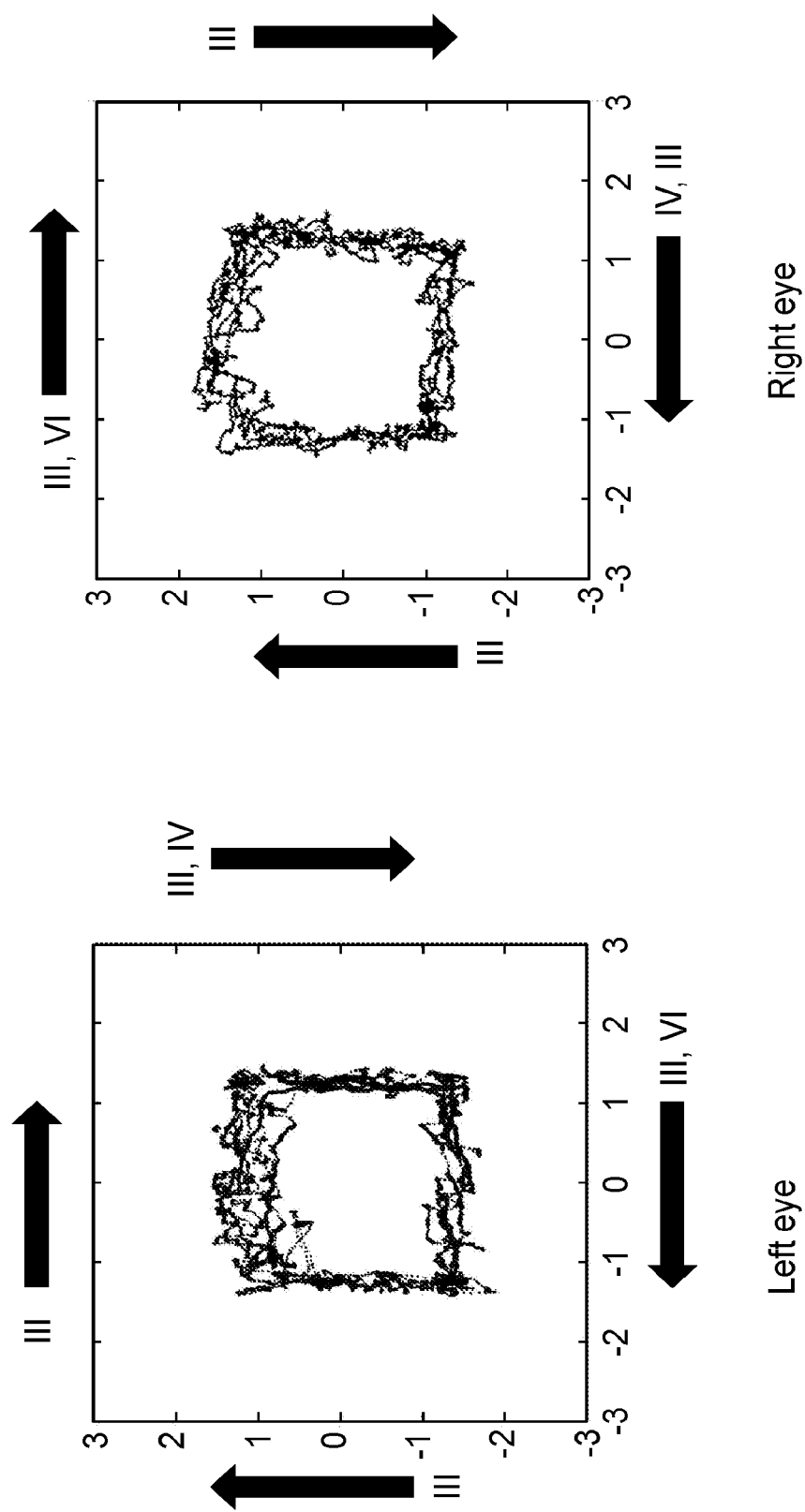
FIG. 3 demonstrates that cranial nerves III, IV and VI effectively move the eyes in a square so that eye motion may be analyzed with reference to particular fields and with reference to control by particular cranial nerves.
Figure 4:
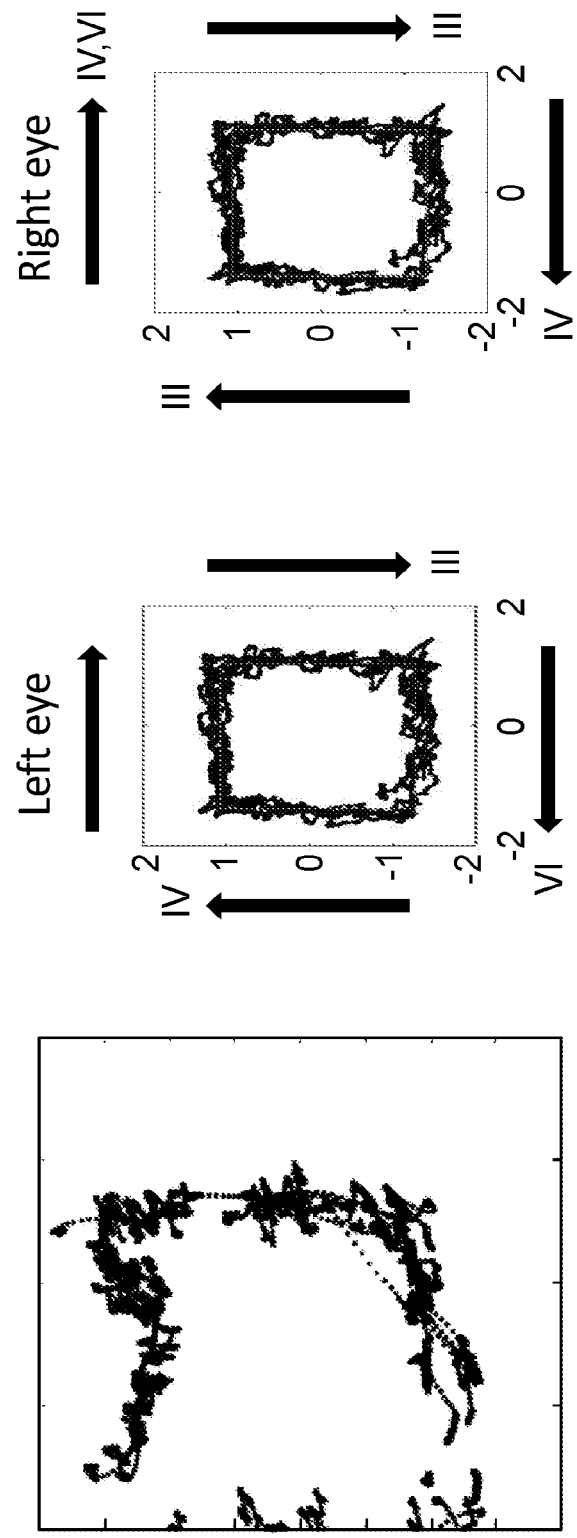
FIG. 4 demonstrates the eye movement tracking of the left eye in a patient with a right VIth nerve palsy from remote trauma with no elevated intracranial pressure.
Figure 5:
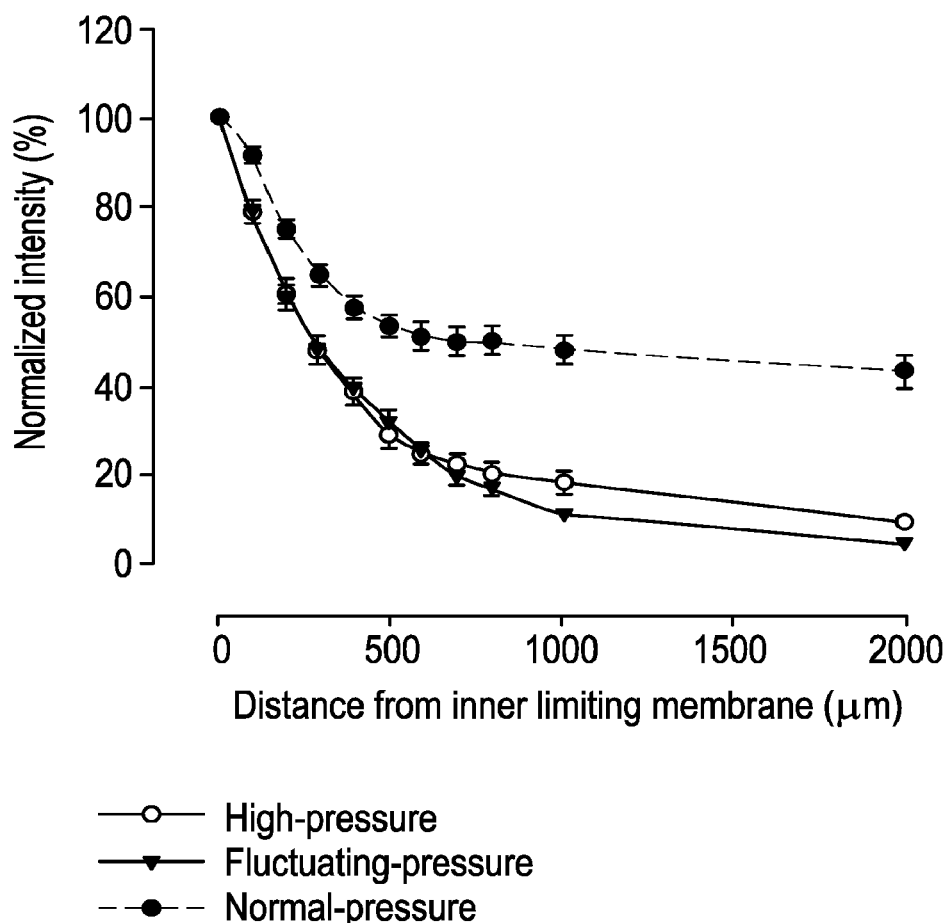
FIG. 5 provides a comparison of fluctuating and sustained neural pressure perturbations on axonal transport processes in the optic nerve Balaratnasingam[aa] et al. *Brain Research*, 2011; 1417:67-76.
Figure 6:
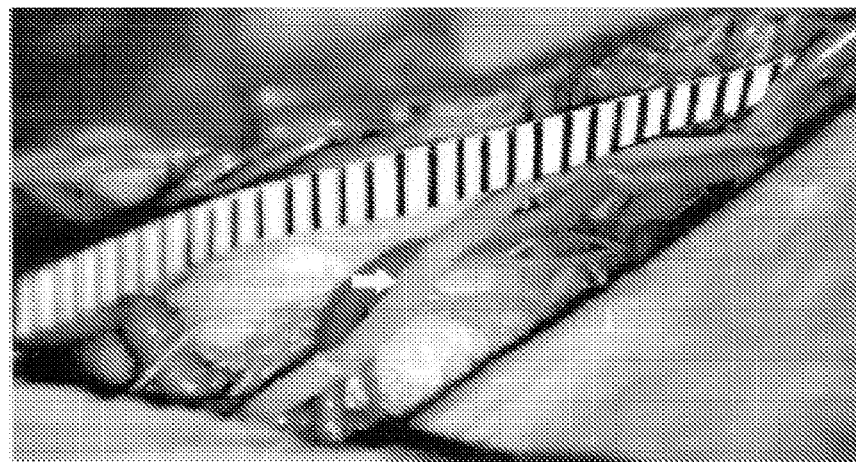
FIG. 6 illustrates the IV cranial nerve exposed in the subarachnoid space.
Figure 11:
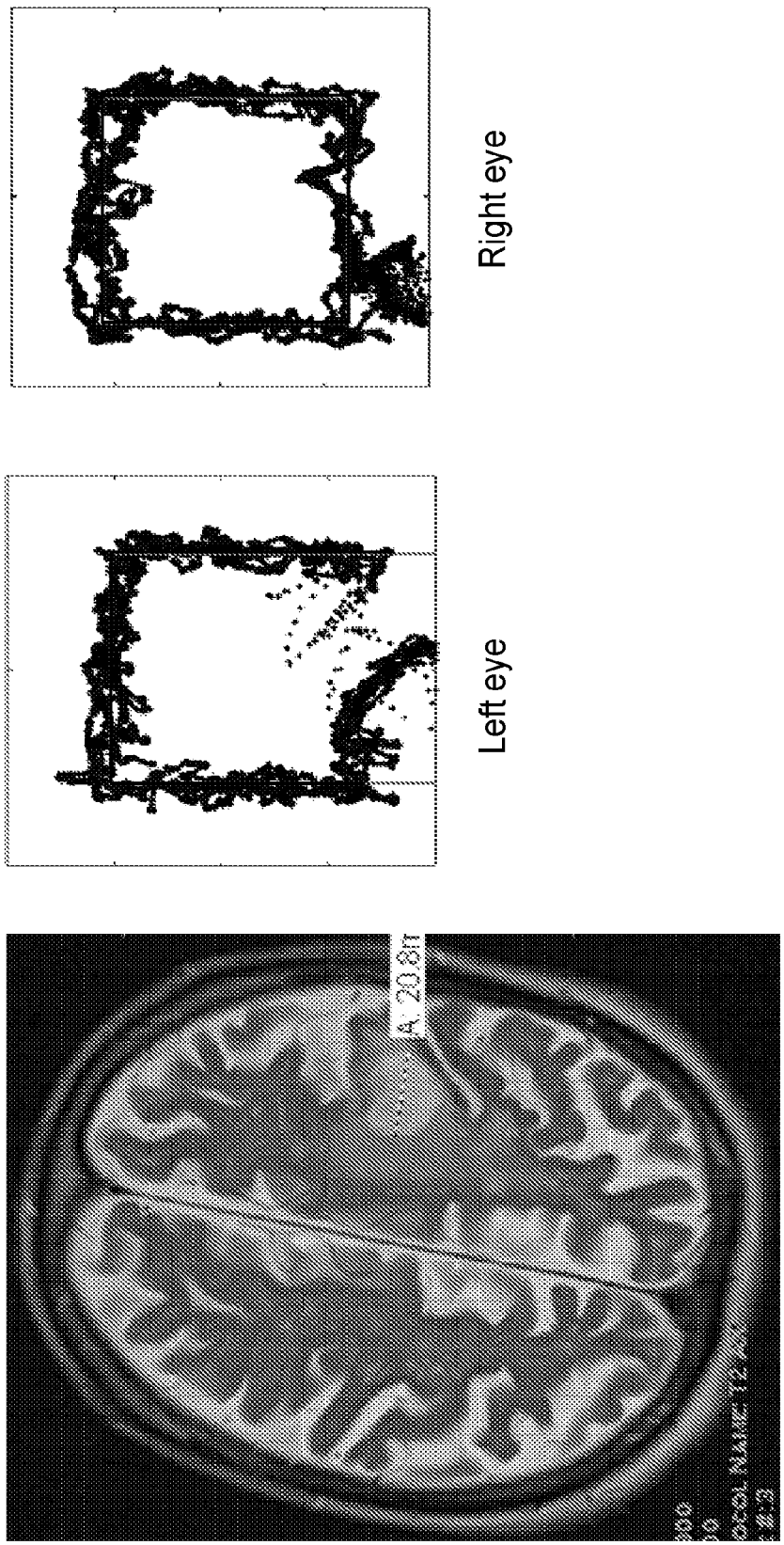
FIG. 11 demonstrates the eye movement tracking of an 86 year old male who presented with speech difficulty. There is a cortical lesion producing mass effect that decreases the integrity of the inferior box wall on eye tracking.
Figure 12:
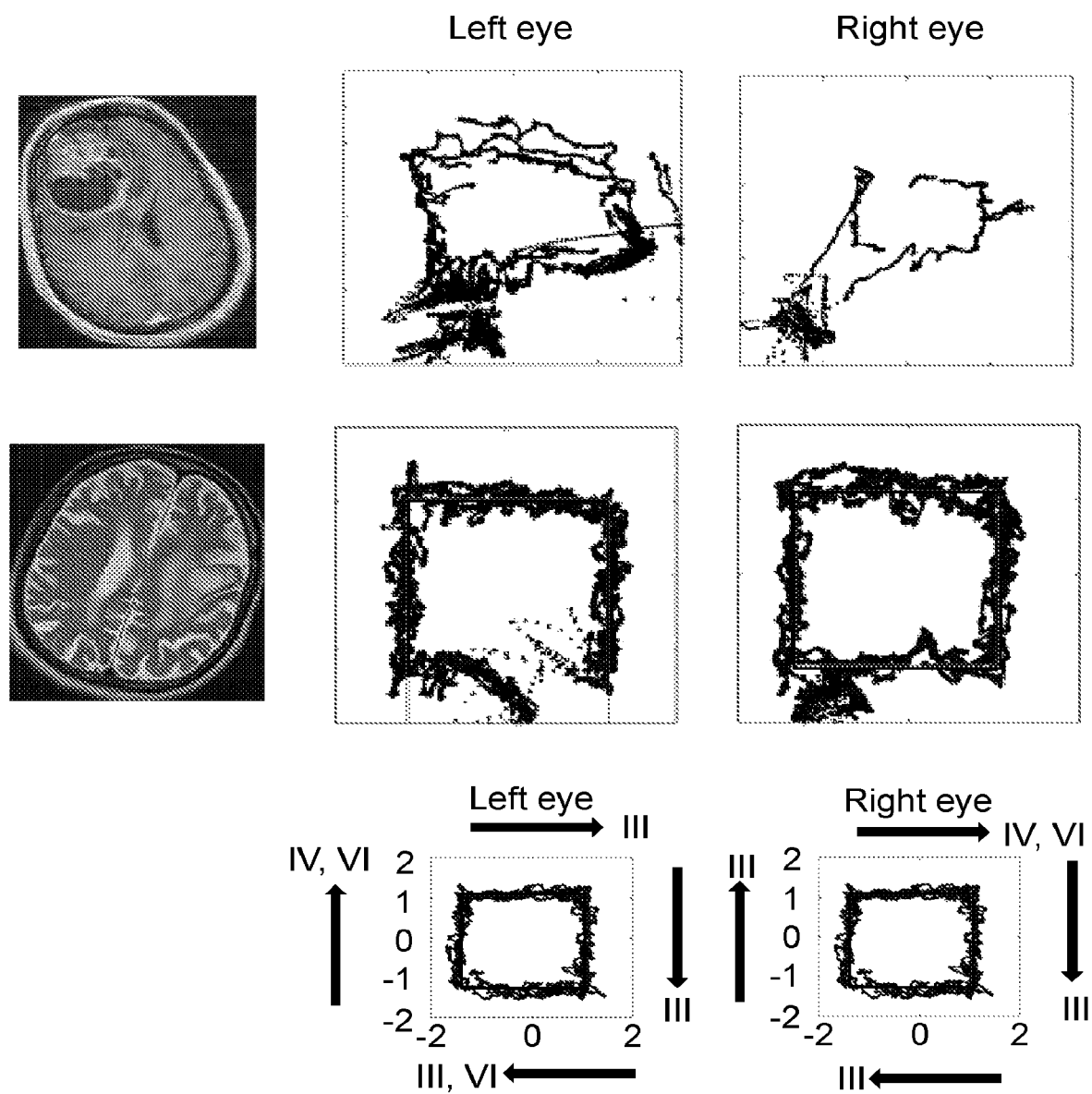
FIG. 12 demonstrates the eye movement tracking of a patient with an intracranial lesion demonstrating elevated Intracranial Pressure may be used localize the lesion.
Figure 13:
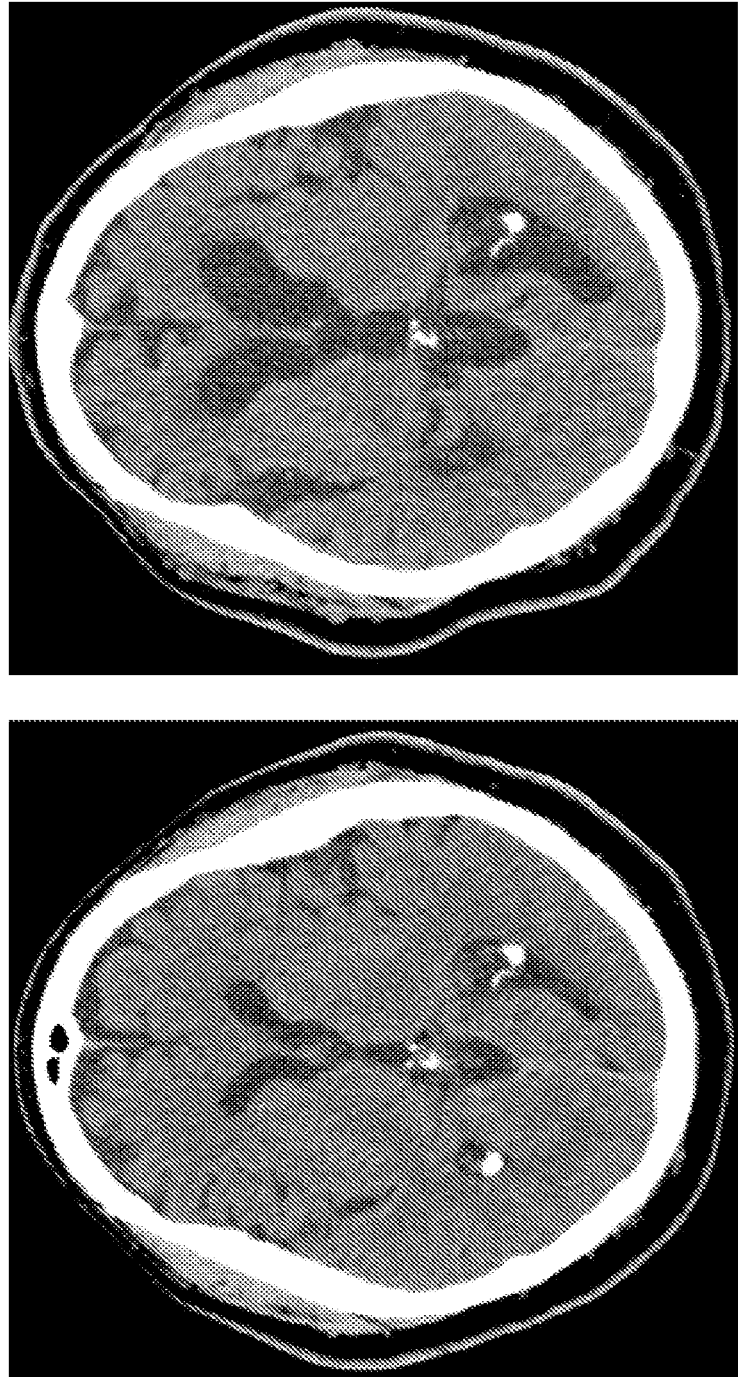
FIG. 13 provides the head CT scans of a hydrocephalic patient, a 62 y.o. male s/p resection, chemo and XRT of a thoracic ependymoma in 2002 at an OSH; resultant paraplegia, with recurrence in 2010; declined surgical intervention until developing worsening UE function and decreased spontaneous speech in December 2011.
Figure 14:
FIG. 14 provides the CT scans of the patient described in FIG. 13. The patient underwent re-resection of ependymoma, and placement of ventriculostomy, mental status returned to baseline, and the ventriculostomy was weaned. The patient re-presented with paucity of spontaneous speech; hydrocephalus necessitating a shunt.
Figure 15:
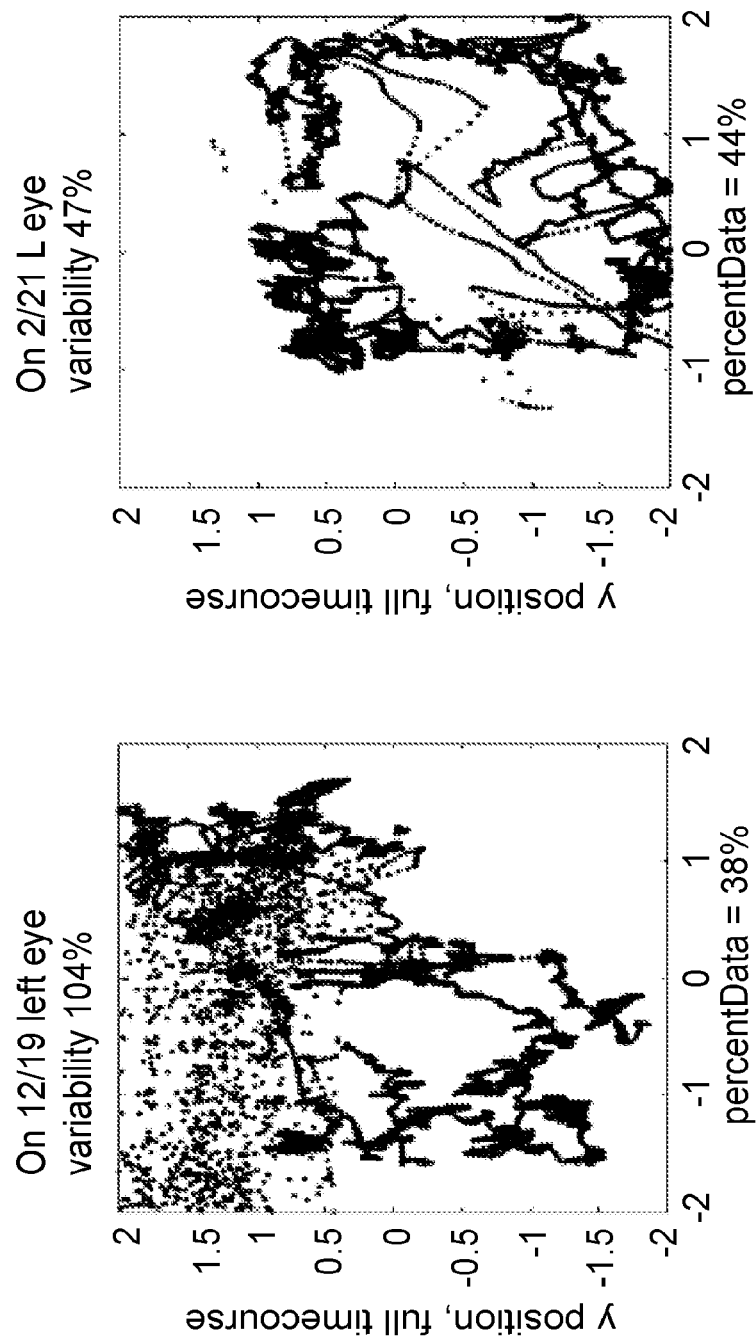
FIG. 15 demonstrates the eye movement tracking of a patient recovering from aphasia and coma suggesting that eye movement tracking can be used as a quantitative outcome measure for recovery from aphasia and minimally conscious states FIG. 16 demonstrates the eye movement tracking of an aphasic patient demonstrating that eye movement tracking can be performed in a patient who does not follow instructions.
Figure 16:
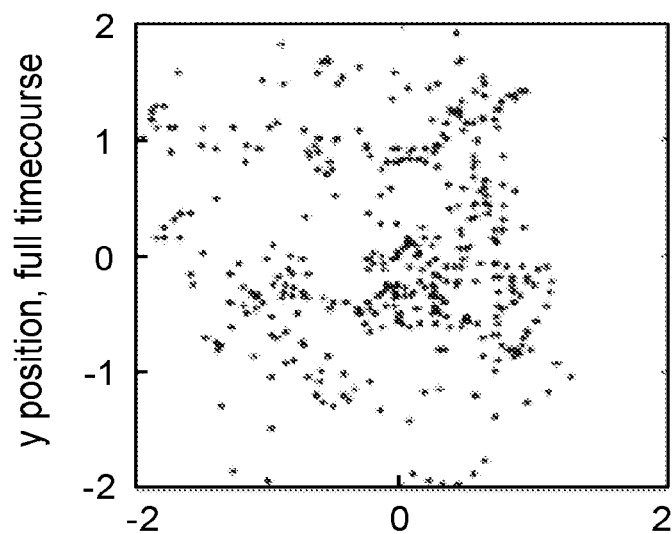

We created scatterplots of the entire time series by plotting the 100,000 (x,y) pairs representing the two orthogonal components of the instantaneous angle of pupil reflection over time to create 'box trajectories' that reflected the temporal nature of the pupillary movement. In control subjects, these figures look like boxes, reflecting the timing of the aperture as it moved around the screen (FIG. 3).

Results

We tracked normal volunteer subjects including a neurosurgical chief resident, aged 36, without known cognitive deficit, and an 87 year old male with multiple medical and ocular problems and no known cognitive deficit. Both normal volunteers had similar variability on tracking.

We then tracked 3 subjects being treated for normal pressure hydrocephalus.

Case 1 (FIG. 31): 68 year old male with a past medical history of HIV infection, diabetes, hypertension, and stroke presented after 2 falls to his neurologist. A large volume lumbar puncture was performed. The opening pressure was 3 cm. The patient's gait was dramatically improved by the tap. A Codman shunt with Certas programmable valve set to 4 was placed and the patient continued to demonstrate progressive improvement clinically. Serial tracking was performed and paralleled the clinical improvement in gait (FIG. 29).

Case 2 (FIG. 32): A 57 year old construction worker with presented with increasing gait disturbance and memory problems progressive over 5 years. He was fired from his job as a construction worker after falling at work. His mini mental status exam improved by 3 points, as did his gait after a large volume lumbar puncture. A Codman shunt with Certas programmable valve set to 5 was placed and the patient continued to demonstrate progressive improvement clinically. Serial tracking was performed and paralleled the clinical improvement in gait (FIG. 3).

Case 3 (FIG. 33): An 87 year old male World War II veteran with a past medical history of asthma, hypertension, posttraumatic stress disorder and benign prostatic hypertrophy had undergone shunting for normal pressure hydrocephalus at the age of 73 for a gait apraxia. A medium pressure PS medical valve was placed at that time. He underwent three subsequent distal shunt revisions without changing of the valve. He now presented again with progressive gait apraxia and shuntogram demonstrating distal malfunction. Since he had already failed three intraperitoneal shunts, the shunt was now revised and placed in the pleural space. Neither the valve, nor the shunt tubing was changed. The patient demonstrated improvement in his gait which paralleled the improvement in tracking (FIG. 31).

We thus have three demonstrated cases of improvement in tracking after shunting for NPH. While it is conceivable that the patients' tracking improved only because they were serially tracked and they demonstrated a 'learning effect' at watching the video, serial tracking of a 57 year old male with multiple sclerosis and bilateral optic neuropathy demonstrated no such serial improvement (FIG. 32).

Discussion

These results indicate that increased variability is not dependent on the age of the subject. Increased variability on tracking correlates with increased gait disturbance due to normal pressure hydrocephalus. While the concept of eye movement tracking to assess dementia is not new, the use of eye tracking to assess shunt malfunction that does not measurably impact cognitive functioning is novel. The performance of tracking while watching television, and without requiring the cooperation of the subject being tracked also represents a significant development. Our methodology assesses physiologic functioning of the central nervous system and thus is different from imaging technologies enabling visualization of brain anatomy. Imaging of the brain may or may not be diagnostic of shunt malfunction with NPH. Uncalibrated ocular motility tracking assessment does not require that the subject explicitly consent to being tracked prior to assessment of their central nervous system functioning, and thus raises ethical considerations. Dementia, schizophrenia, amyotrophic lateral sclerosis, autism and Fragile X are among the numerous diseases with characteristic anomalies detectable using eye movement tracking technology (Sharma, et al. *Archives of neurology* (2011) 68: 857-861; Pelak, *Current neurology and neuroscience reports* (2010) 10: 440-447; Hicks, et al., *Progress in brain research* (2008) 171: 555-558; Kennedy, et al., *Neuropsychologia* (2010) 48: 3392-3398 and Levy, et al., *Current topics in behavioral neurosciences* (2010) 4: 311-347).

Example 4

Evaluation of Posterior Fossa Mass Effect as Manifested by Cranial Nerve VI Palsy Background Cranial nerve VI is considered highly susceptible to neuropathy due to its anatomical vulnerability (Hanson et al., *Neurology* 2004; 62(1):33-36). The abducens nerve (VI) exits the brainstem from its tethering at the medullopontine junction and courses intracranially before entering Dorello's canal, where it is again tethered by fibrous and osseous structures. Posterior fossa lesions pushing the cerebellum and brainstem forward may directly compress the VIth nerve against the clivus (Hanson et al., *Neurology* 2004; 62(1): 33-36).

Methods

Subjects' eye movements were recorded with an Eyelink 1000 eye tracker at a relatively fixed distance from a computer monitor over a fixed period of time. The visual stimulus provided was the Shakira music video Waka-Waka played continuously in a square aperture with an area approximately ⅛ the screen size while moving clockwise along the outer edges of the monitor for five complete cycles of 40 seconds each. The eye tracker sampled pupil position at 500 Hz, yielding 100,000 samples over 200 seconds. Scatterplots of the entire time series were created by plotting the 100,000 (x,y) pairs representing the two orthogonal components of the instantaneous angle of pupil reflection over time to create 'box trajectories' that reflected the temporal nature of the pupillary movement. In control subjects, these figures look like boxes, reflecting the timing of the aperture as it moved around the screen (FIG. 20).

Aspect Ratio. Elapsed time quantitation enables localization of the video aperture during measurement of eye position. Box height=median top value−median bottom value while the video traverses top and bottom. Similarly the width of the box is calculated based on where the pupil is when the video aperture is on the right and left sides. Aspect ratio=height/width. (calculation shown FIG. 24).

Individuals

Tracking of a person with a known VIth nerve palsy resulting in diplopia and detected by an ophthalmologist was compared to normal controls. Although the box trajectory appeared flattened (FIG. 35 left), calculation of the aspect ratio revealed that it was indeed taller and narrower than a control trajectory (FIG. 35 right).

Two patients presented with posterior fossa lesions that partially obliterated the fourth ventricle. The first was a 54 yo male with poorly differentiated papillary carcinoma who presented with a tender mass on the back of his head and a progressive headache. He did not have papilledema on clinical examination. Imaging revealed a calvarial based metastasis nearly obliterating the fourth ventricle (FIG. 36). Note that there was no transependymal flow on MRI to suggest hydrocephalus (FIG. 36 right). Eye tracking demonstrated a box narrower than it was wide (increased aspect ratio) consistent with CN VI palsy.

The mass was resected. Repeat imaging on postoperative day one (FIG. 35) showed that the boxes had returned to having a normal aspect ratio (FIG. 35).

The second patient was a 56 year old male who presented with a lung mass and headaches. He did not have papilledema on clinical examination. MRI revealed a large intraxial mass near the cerebellopontine angle, but interestingly, pushing the left side of brainstem up against the clivus rather than the right. Note that there was no transependymal flow on MRI to suggest hydrocephalus (FIG. 37 right). Eye tracking of the right eye demonstrated a box narrower than it was wide (increased aspect ratio) consistent with CN VI palsy. Postoperatively his aspect ratio returned to normal (FIG. 38)

A 59 year old woman presenting with dizziness and headaches was found to have hydrocephalus with no papilledema, but transependymal flow on MRI scan (FIG. 38). She was being evaluated by neurology for sarcoidosis, which is commonly known to cause VIth nerve palsy. She was also noted to have a box with an increased aspect ratio. She was shunted and her aspect ratio returned to normal postoperatively (FIG. 40 bottom).

Example 5

Evaluation of Disorders Impeding Conductance Through the Optic Disc and Nerve

Tracking of patients with lesions compressing the optic nerve and resulting in visual field cuts did not result in detectable changes in ocular motility, as long as the subject still had minimal vision in at least one eye.

Lesions resulting in slowed conduction within the optic nerve however, resulted in a pattern with increased vertical range, and left the box trajectory with no roof or floor, causing a statistically significant in y-variability with relative preservation of x-variability compared to both healthy control patients and the larger group of patients with neuro or ophthalmic deficits.

Individuals:

A patient with ocular histoplasmosis resulting in central optic nerve atrophy (FIG. 41) showed extensive y-variability. A 25 year old female patient being evaluated for optic neuritis also had increased y-variability (FIG. 42). A patient with disconjugate due to multiple sclerosis demonstrated multiple cranial neuropathies (FIG. 43). This pattern was not seen in the healthy control subjects nor in other patients including several with tumors impinging on the optic nerve, chiasm or tract or with poor visual acuity due to known ocular non-neuronal pathology.

Papilledema, or swelling of the optic disc, is caused by elevated intracranial pressure due to large brain tumors as well as other pathologies. It is thought to indicate delayed axoplasmic transport along the optic nerve. Eye movement tracking of the left eye of a patient with a large right frontal brain tumor presenting with an examination consistent with papilledema demonstrated an increased vertical range box trajectory with no roof or floor similar to those seen in the central optic nerve atrophy and ocular histoplasmosis patients (FIG. 44). This statistically significant deviation in y-variability resolved with steroids over 24 hours (FIG. 45). The height of the patient's box trajectory remained decreased after the steroids and before resection, suggesting a component of IIIrd nerve palsy. The eye tracking trajectory returned to normal by one week after resection (FIG. 46).

The invention claimed is:

1. A system comprising:
   an eye tracker having a camera, the eye tracker being configured and arranged to track an eye movement of a subject along a box trajectory having a top arm, a bottom arm and two side arms to obtain at least 100,000 samples of eye position over a period of 30 to 500 seconds;
   a display configured to present a stimulus to the subject; and
   a processor in communication with the eye tracker, the processor being configured and arranged to:
      create a dataset of the eye movement as the subject responds to the stimulus;
      generate a plot of the dataset corresponding to at least one of the top arm and the bottom arm, the plot reflecting a timecourse of eye position versus time; and
      identify the presence of scanning vision by detecting one or more streaking vertical lines in the plot to indicate a deficit in a cranial nerve function.

2. The system according to claim 1, wherein the eye movement is tracked in response to a visual stimulus presented on a display.

3. A system of screening for multiple sclerosis in a subject, comprising:
   an eye tracker having a camera, the eye tracker being configured and arranged to track an eye movement of a subject along a box trajectory having a top arm, a bottom arm and two side arms to obtain at least 100,000 samples of eye position over a period of 30 to 500 seconds;
   a display configured to present a stimulus to the subject; and
   a processor in communication with the eye tracker, the processor being configured and arranged to:
      create a dataset of the eye movement as the subject responds to the stimulus;
      plot a timecourse of eye position versus time corresponding to at least one of the top arm and the bottom arm; and
      identify one or more features in the plot to indicate a deficit in a cranial nerve function wherein the processor is configured and arranged to confirm the presence of scanning vision by monitoring for one or more streaking vertical lines.

4. The system according to claim 3, wherein the eye movement is tracked in response to a visual stimulus presented on a display.

* * * * *